(12) United States Patent
Conradie et al.

(10) Patent No.: US 10,988,783 B2
(45) Date of Patent: Apr. 27, 2021

(54) METHODS AND MATERIALS FOR PRODUCING 7-CARBON MONOMERS

(71) Applicant: INV NYLON CHEMICALS AMERICAS, LLC, Wilmington, DE (US)

(72) Inventors: Alex Van Eck Conradie, Eaglescliffe (GB); Adriana Leonora Botes, Rosedale East (GB); Jonathan Kennedy, Stokesley-Middlesbrough (GB); Nadia Fatma Kadi, Middlesbrough (GB)

(73) Assignee: INV NYLON CHEMICALS AMERICAS, LLC, Wilmington, DE (US)

( * ) Notice: Subject to any disclaimer, the term of this patent is extended or adjusted under 35 U.S.C. 154(b) by 0 days.

(21) Appl. No.: 16/565,968

(22) Filed: Sep. 10, 2019

(65) Prior Publication Data
US 2020/0248210 A1    Aug. 6, 2020

Related U.S. Application Data

(63) Continuation of application No. 16/262,184, filed on Jan. 30, 2019, now abandoned, which is a continuation of application No. 15/368,419, filed on Dec. 2, 2016, now abandoned.

(60) Provisional application No. 62/263,317, filed on Dec. 4, 2015.

(51) Int. Cl.
| | |
|---|---|
| *C08G 69/02* | (2006.01) |
| *C12N 9/08* | (2006.01) |
| *C12P 11/00* | (2006.01) |
| *C12P 7/26* | (2006.01) |
| *C12P 21/00* | (2006.01) |
| *C12P 13/00* | (2006.01) |
| *C12P 19/32* | (2006.01) |
| *C12N 9/04* | (2006.01) |
| *C12N 9/02* | (2006.01) |
| *C12N 9/10* | (2006.01) |
| *C12N 9/88* | (2006.01) |

(52) U.S. Cl.
CPC .......... *C12P 7/26* (2013.01); *C12N 9/001* (2013.01); *C12N 9/0006* (2013.01); *C12N 9/1029* (2013.01); *C12N 9/13* (2013.01); *C12N 9/88* (2013.01); *C12P 11/00* (2013.01); *C12P 13/00* (2013.01); *C12P 19/32* (2013.01); *C12P 21/00* (2013.01); *C12Y 101/011* (2013.01); *C12Y 101/01035* (2013.01); *C12Y 103/01009* (2013.01); *C12Y 103/01038* (2013.01); *C12Y 203/01016* (2013.01); *C12Y 203/0118* (2013.01); *C12Y 203/01041* (2013.01); *C12Y 203/01174* (2013.01); *C12Y 203/01179* (2013.01); *C12Y 208/03* (2013.01); *C12Y 402/01017* (2013.01)

(58) Field of Classification Search
None
See application file for complete search history.

(56) References Cited

U.S. PATENT DOCUMENTS

| | | |
|---|---|---|
| 2014/0186904 A1 | 7/2014 | Botes et al. |
| 2015/0291987 A1 | 10/2015 | Lau |
| 2016/0201097 A1 | 7/2016 | Botes et al. |
| 2017/0159092 A1 | 6/2017 | Conradie et al. |

FOREIGN PATENT DOCUMENTS

| | | |
|---|---|---|
| WO | WO 2016/007258 A1 | 1/2016 |
| WO | WO 2017/096260 A1 | 6/2017 |
| WO | WO 2017/096310 A1 | 6/2017 |
| WO | WO 2017/096260 A8 | 4/2018 |

OTHER PUBLICATIONS

Barker, et al., "Enzymatic Reactions in the Degradation of 5-Aminovalerate by Clostridium Aminovalericum," *The Journal of Biological Chemistry*, vol. 262, No. 19, 1987, pp. 8994-9003.
Becker, et al., "Metabolic Flux Engineering of L-Lysine Production in Corynebacterium Glutamicum—Over Expression and Modification of G6P Dehydrogenase," *Journal of Biotechnology*, vol. 132, 2007, pp. 99-109.
Bellmann, et al., "Expression Control and Specificity of the Basic Amino Acid Exporter LysE of Corynebacterium Glutamicum," *Microbiology*, vol. 147, 2001, pp. 1765-1774.
Bond-Watts, et al., "Biochemical and Structural Characterization of the Trans-Enoyl-CoA Reductase from Treponema Denticola," *Biochemistry*, vol. 51, 2012, pp. 6827-6837.
Brigham, et al., "Engineering Ralstonia Eutropha for Production of Isobutanol from CO2, H2, and O2," *Advanced Biofuels and Bioproducts*, Springer New York, Chapter 39, 2013, pp. 1065-1090.
Budde et al., "Roles of Multiple Acetoacetyl Coenzyme A Reductases in Polyhydroxybutyrate Biosynthesis in Ralstonia Eutropha H16," *Journal of Bacterialolgy*, vol. 192, No. 20, Oct. 2010, pp. 5319-5328.
Bugg, et al., "The Emerging Role for Bacteria in Lignin Degradation and Bio-Product Formation," *Current Opinion in Biotechnology*, vol. 22, 2011, pp. 394-400.
Cantu, et al., "Thioesterases: A New Perspective Based on their Primary and Tertiary Structures," *Protein Science*, vol. 19, 2010, pp. 1281-1295.

(Continued)

Primary Examiner — Kagnew H Gebreyesus

(57) ABSTRACT

This document describes biochemical pathways for producing 7-aminoheptanoic acid using a β-ketoacyl synthase or a β-ketothiolase to form either a 5-amino-3-oxopentanoyl-[ACP] or 5-amino-3-oxopentanoyl-CoA intermediate. 7-aminoheptanoic acid can be enzymatically converted to pimelic acid, 7-hydroxyheptanoic acid, heptamethylenediamine or 1,7-heptanediol or the corresponding salts thereof. This document also describes recombinant microorganisms producing 7-aminoheptanoic acid as well as pimelic acid, 7-hydroxyheptanoic acid, heptamethylenediamine and 1,7-heptanediol or the corresponding salts thereof.

31 Claims, 31 Drawing Sheets

Specification includes a Sequence Listing.

(56) References Cited

OTHER PUBLICATIONS

Cheon et al., (2016) "Recent Trends in Metabolic Engineering of Microorganisms for the Production of Advanced Biofuels," *Current Opinion in Chemical Biology*, 35:10-21.

Elkins, et al., "Substrate Specificity of the RND-Type Multidrug Efflux Pumps AcrB and AcrD of *Escherichia coli* is Determined Predominately by Two Large Periplasmic Loops," *Journal of Bacteriology*, vol. 184, No. 23, 2002, pp. 6490-6498.

Gloerich, et al., "Peroxisomal Trans-2-Enoyl-CoA Reductase is Involved in Phytol Degradation," *FEBS Letters*, vol. 580, 2006, pp. 2092-2096.

Guerrillot, et al., "Purification and Characterization of Two Aldehyde Dehydrogenases from Pseudomonas Aeruginosa," *European Journal of Biochemistry*, vol. 81, 1977, pp. 185-192.

Hermann, Thomas, "Industrial Production of Amino Acids by Coryneform Bacteria," *Journal of Biotechnology*, vol. 104, 2003, pp. 155-172.

Huhn, et al., "Identification of the Membrane Protein SucE and its Role in Succinate Transport in Corynebacterium Glutamicum," *Applied Microbiology and Biotechnology*, vol. 89, 2011, pp. 327-335.

Inui, et al., "Fatty Acids Synthesis in Mitochrondria of Euglena Gracilis," *European Journal of Biochemistry*, vol. 142, 1984, pp. 121-126.

Iwaki, et al., "Identification of a Transcriptional Activator (ChnR) and A 6-Oxohexanoate Dehydrogenase (ChnE) in the Cyclohexanol Catabolic Pathway in *Acinetobacter* sp. Strain NCIMB 9871 and Localization of the Genes That Encode Them," *Applied and Environmental Microbiology*, vol. 65, No. 11, 1999, pp. 5158-5162.

Jarboe, Laura R., "YqhD: A Broad-Substrate Range Aldehyde Reductase with Various Applications in Production of Biorenewable Fuels and Chemicals," *Applied Microbiology and Biotechnology*, vol. 89, No. 2, 2011, pp. 249-257.

Jaremko et al., "The Initial Metabolic Conversion of Levulinic Acid in Cupriavidus Necator," *Journal of Biotechnology*, vol. 155, 2011, pp. 293-298.

Kaulmann, et al., "Substrate Spectrum of ω-Transaminase from Chromobacterium Violaceum DSM30191 and its Potential for Biocatalysis," *Enzyme and Microbial Technology*, vol. 41, 2007, pp. 628-637.

Kim, Ki-Han, "Purification and Properties of a Mine α-Ketoglutarate Transaminase from *Escherichia coli,*" *Journal of Biological Chemistry*, vol. 239, No. 3, 1964, pp. 783-786.

Köpke, et al., "2, 3-Butanediol Production by Acetogenic Bacteria, An Alternative Route to Chemical Synthesis, Using Industrial Waste Gas," *Applied and Environmental Microbiology*, vol. 77, No. 15, 2011, pp. 5467-5475.

Larroy, et al., "Characterization of the *Saccharomyces cerevisiae* YMR318C (ADH6) Gene Product as a Broad Specificity NADPH-Dependent Alcohol Dehydrogenase: Relevance in Aldehyde Reduction," *Biochemical Journal*, vol. 361, No. 1, 2002, 163-172.

Lee, et al., "Synthesis of Pure Meso-2, 3-Butanediol from Crude Glycerol Using an Engineered Metabolic Pathway in *Escherichia coli*," *Applied Biochemistry and Biotechnology*, vol. 166, No. 7, 2012, pp. 1801-1813.

Lee, et al.,"Metabolic Engineering of Pentose Phosphate Pathway in Ralstonia Eutropha for Enhanced Biosynthesis of Poly-β-Hydroxybutyrate," *Biotechnology Process*, vol. 19, No. 5, 2003, pp. 1444-1449.

Li, et al., "Cupriavidus Necator JMP134 Rapidly Reduces Furfural With a Zn-Dependent Alcohol Dehydrogenase," *Biodegradation*, vol. 22, No. 6, 2011, pp. 1215-1225.

Lim, et al., "Amplification of the NADPH-Related Genes zwf and gnd for the Oddball Biosynthesis of PHB in an *E. coli* Transformant Harboring a Cloned phbCAB Operon," *Journal of Bioscience and Bioengineering*, vol. 93, No. 6, 2002, pp. 543-549.

Liu, et al.,"Two Novel Metal-Independent Long-Chain Alkyl Alcohol Dehydrogenases from Geobacillus Thermodenitrificans NG80-2," *Microbiology*, vol. 155, No. 6, 2009, pp. 2078-2085.

Lopez-Sánchez, et al., "Tetralin-Induced and ThnR-Regulated Aldehyde Dehydrogenase and β-Oxidation Genes in Sphingomonas Macrogolitabida Strain TFA," *Applied and Environmental Microbiology*, vol. 76, No. 1, 2010, pp. 110-118.

Martin, et al., "High-Titer Production of Monomeric Hydroxyvalerates from Levulinic Acid in Pseudomanas Putida," *Journal of Biotechnology*, vol. 139, No. 1, 2009, pp. 61-67.

Meijnen, et al., "Improved p-Hydroxybenzoate Production by Engineered Pseudomonas Putida S12 by Using a Mixed-Substrate Feeding Strategy," *Applied Microbiology and Biotechnology*, vol. 90, No. 3, 2011, pp. 885-893.

Naggert, et al., "Cloning, Sequencing, and Characterization of *Escherichia coli* Thioesterase II," *The Journal of Biological Chemistry*, vol. 266, No. 17, 1991, pp. 11044-11050.

Neyfakh, Alexander A., et al., "The Multidrug Efflux Transporter of Bacillus Subtillis is a Structural and Functional Homolog of the *Staphylococcus* NorA Protein," *Antimcrobial Agents and Chemotherapy*, vol. 36, No. 2, 1992, pp. 484-485.

NG, et al., "Quinolone Resistance Mediated by NorA: Physiologic Characterization and Relationship to flqB, A Quinolone Resistance Locus on the *Staphyloccus aureus* Chromosome," *Antimicrobial Agents and Chemotherapy*, vol. 38, No. 6, 1994, pp. 1345-1355.

Nishimaki, et al., "Studies on the Metabolism of Unsaturated Fatty Acids XIV, Purification and Properties of NADPH-Dependent Trans-2-Enoyl-CoA Reductase of *Escherichia coli* K-12," *The Journal of Biochemistry*, vol. 95, No. 5, 1984, pp. 1315-1321.

Nomura et al., "Expression of 3-Ketoacyl-Acyl Carrier Protein Reductase (fabG) Genese Enhances Production of Polyhydroxyalkanoate Copolymer from Glucose in Recominant *Eschericia coli* JM109," *Applied and Environmental Microbiology*, vol. 71, No. 8, Aug. 2005, pp. 4297-4306.

Ohashi, et al., "Continuous Production of Lactic Acid from Molasses by Perfusion Culture of Lactococcus Lactis Using a Stirred Ceramic Membrane Reactor," *Journal of Bioscience and Bioengineering*, vol. 87, No. 5, 1999, pp. 647-654.

Papanikolaou, et al., "Citric Acid Production by Yarrowia Lipolytica Cultivated on Olive-Mill Wastewater-Based Media," *Bioresource Technology*, vol. 99, 2008, pp. 2419-2428.

PCT International Preliminary Report on Patentability issued in PCT/US2016/064833, dated Jun. 5, 2017, 10 pages.

PCT International Search Report issued in PCT/US2016/064833, dated Jun. 8, 2017, 5 pages.

PCT Written Opinion of the International Searching Authority issued in PCT/US2016/064833, dated Jun. 8, 2017, 9 pages.

Perez-Pantoja, et al., "Metabolic Reconstruction of Aromatic Compounds Degradation from the Genome of the Amazing Pollutant-Degrading Bacterium Cupriavidus Necator JMP134," *FEMS Microbiology Reviews*, vol. 32, 2008, pp. 736-794.

Przbylski, et al., "Third-Generation Feed Stocks for the Clean and Sustainable Biotechnological Production of Bulk Chemicals: Synthesis of 2-Hydroxyisobutric Acid," *Energy, Sustainability and Society*, vol. 2, No. 11, 2012, pp. 1-9.

Ramsay, et al., "Use of a Nylon Manufacturing Waste as an Industrial Fermentation Substrate," *Applied and Environmental Microbiology*, vol. 52, No. 1, 1986, pp. 152-156.

Samsonova, et al., "Molecular Cloning and Characterization of *Escherichia coli* K12 ygjG Gene," *BMC Microbiology*, vol. 3, No. 2, 2003, pp. 1-10.

Satoh, et al., "Enzyme-Catalyzed Poly (3-Hydroxybutyrate) Synthesis from Acetate with CoA Recycling and NADPH Regeneration in Vitro," *Journal of Bioscience and Bioengineering*, vol. 95, No. 4, 2003, pp. 335-341.

Scheller, et al., "Generation of the Soluble and Functional Cytosolic Domain of Microsomal Cytochrome P450 52A3," *Journal of Biological Chemistry*, vol. 269, No. 17, 1994, pp. 12779-12783.

Seedorf, et al., "The Genome of Clostridium Kluyveri, a Strict Anaerobe with Unique Metabolic Features," *Proceedings of the National Academy of Sciences*, vol. 105, No. 6, 2008, pp. 2128-2133.

Shen, et al., "Driving Forces Enable High-Titer Anaerobic 1-Butanol Synthesis in *Escherichia coli*," *Applied and Environmental Microbiology*, vol. 77, No. 9, 2011, pp. 2905-2915.

(56) References Cited

OTHER PUBLICATIONS

Suzuki et al., "Acetylputrescine Deacetylase from Micrococcus Luteus K-11," *Biochimica et Biophysica Acta (BBA)—General Subjects*, vol. 882, Issue 1, Jun. 1986, pp. 140-142.

Suzuki, et al., "GriC and GriD Constitute a Carboxylic Acid Reductase Involved in Grixazone Biosynthesis in Streptomyces Griseus," *Journal of Antibiotics*, vol. 60, No. 6, 2007, pp. 380-387.

Venkitasubramanian, et al., "Aldehyde Oxidoreductase as a Biocatalyst: Reduction of Vanillic Acid," *Enzyme and Microbial Technology*, vol. 42, No. 2, 2008, pp. 130-137.

Wee, et al., "Biotechnological Production of Lactic Acid and its Recent Applications," *Food Technology and Biotechnology*, vol. 44, No. 2, 2006, pp. 163-172.

Woolridge, et al., "Efflux of the Natural Polyamine Spermidine Facilitated by the Bacillus Subtillis Multidrug Transporter Blt," *Journal of Biological Chemistry*, vol. 272, No. 14, 1997, pp. 8864-8866.

Yang, et al., "Value-Added Uses for Crude Glycerol—A Byproduct of Biodiesel Production," *Biotechnology for Biofuels*, vol. 5, No. 13, 2012, pp. 1-10.

Yonaha, et al., "4-Aminobutyrate: 2-Oxoglutarate Aminotransferase of Streptomyces Griseus," *European Journal of Biochemistry*, vol. 146, 1985, pp. 101-106.

Zhuang, et al., "Divergence of Function in the Hot Dog Fold Enzyme Superfamily: the Bacterial Thioesterase YciA," *Biochemistry*, vol. 47, No. 9, 2008, pp. 2789-2796.

Chibata et al., "[58] ε-Lysine Acylase from Achromobacter pestifer", Methods in Enzymology, vol. 19, 1970, pp. 756-762.

Demain et al., "Scale-up of Microbial processes ", in Manual of Industrial Microbiology and Biotechnology 2nd Edition, SM Press, 1999, Title page and pp. 236-239.

Fage et al., "Coenzyme A-free activity, crystal structure, and rational engineering of a promiscuous ß-ketoacyl thiolase from *Ralstonia eutropha*", Journal of Molecular Catalysis B Enzymatic, vol. 121, Aug. 17, 2015, pp. 113-121.

International Preliminary Report on Patentability received for PCT Application No. PCT/US2016/064765, dated Jun. 5, 2018, 11 pages.

International Search Report received for PCT Application No. PCT/US2016/064765, dated Mar. 13, 2017, 4 pages.

Written Opinion of the International Searching Authority for PCT Application No. PCT/US2016/064765, dated Jun. 8, 2017, 10 pages.

Fig 6
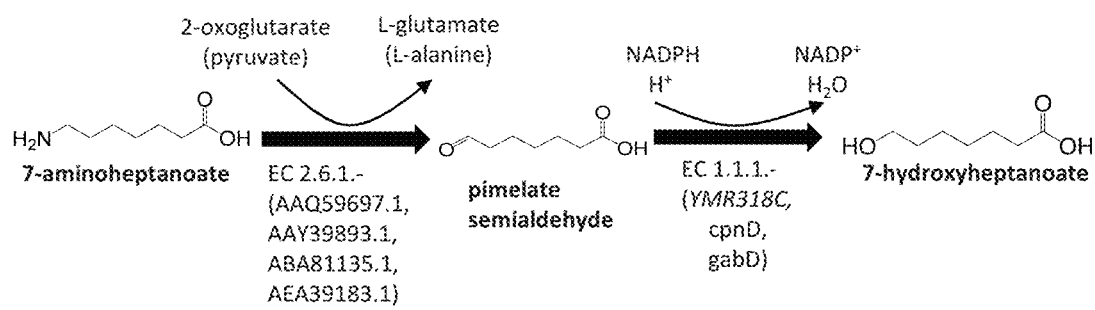
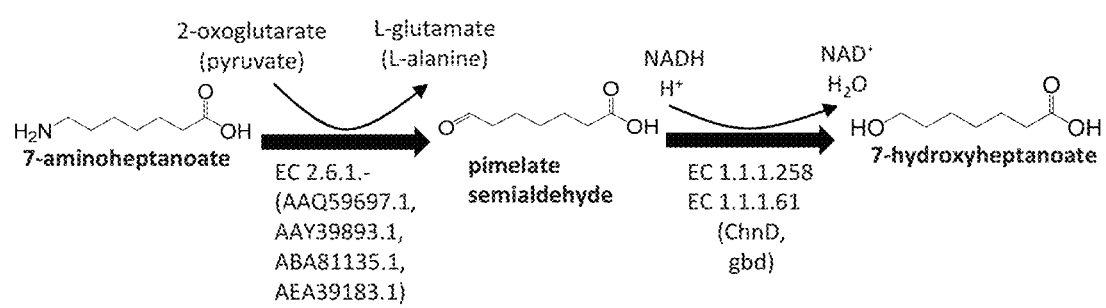

Fig 8A

| SEQ ID NO | Organism | GENBANK reference | Amino acid sequence |
|---|---|---|---|
| 1 | Cupriavidus necator | AAC38322.1 | MTREVVVVSGVRTAIGTFGGSLKDVAPAELGALVVREALARAQVSGD VGHVVFGNVIQTEPRDMYLGRVAAVNGGVTINAPALTVNRLCGSGLQ AIVSAAQTILLGDTDVAIGGGAESMSRAPYLAPAARWGARMGDAGLV DMMLGALHDPFHRIHMGVTAENVAKEYDISRAQQDEAALESHRRASA AIKAGYFKDQIVPVVSKGRKGDVTFDTDEHVRHDATIDDMTKLRPVF VKENGTVTAGNASGLNDAAAAVVMMERAEAERRGLKPLARLVSYGH AGVDPKAMGIPVPATKIALERAGLQVSDLDVIEANEAFAAQACAVT KALGLDPAKVNPNGSGISLGHPIGATGALITVKALHELNRVQGRYALV TMCIGGGQGIAAIFERI |
| 2 | Mycobacterium marinum | ACC40567.1 | MSPITREERLERRIQDLYANDPQFAAAKPATAITAAIERPGLPLPQHETM TGYADRPALAQRSVEFVTDAGTGHTTLRLLPHFETISYGELWDRISALA DVLSTEQTVKPGDRVCLLGFNSVDYATIDMTLARLGAVAVPLQTSAAI TQLQPIVAETQPTMIAASVDALADATELALSGQTATRVLVFDHHRQVD AHRAAVESARERLAGSAVVETLAEAIARGDVPRGASAGSAPGTDVSD DSLALLIYTSGSTGAPKGAMYEPRRNVATFWRKRTWFEGGYEPSITLNF MPMSHVMGRQILYGTLCNGGTAYFVAKSDLSTLFEDLALVRPTELTFV PRVWDMVFDEFQSEVDRRLVDGADRVALEAQVKAEIRNDVLGGRYT SALTGSAPISDEMKAWVEELLDMHLVEGYGSTEAGMILDGAIRRPAV LDYKLVDVPDLGYFLTDRPHPRGELLVKTDSLFPGYYQRAEVTADVF DADGFYRTGDIMAEVGPEQFVYLDRRNNVLKLSQGEFVTVSKLEAVF GDSPLVRQIYIYGNSARAYLLAVIVPTQEALDAVPVEELKARLGDSLQE VAKAAGLQSYEIPRDFIIETTPWTLENGLLTGIRKLARPQLKKHYGELL EQIYTDLAHGQADELRSLRQSGADAPVLVTVCRAAAALLGGSASDVQ PDAHFTDLGGDSLSALSFTNLLHEIFDIEVPVGVIVSPANDLQALADYV EAARKPGSSRPTFASVHGASNGQVTEVHAGDLSLDKFIDAATLAEAPR LPAANTQVRTVLLTGATGFLGRYLALEWLERMDLVDGKLICLVRAKS DTEARARLDKTFDSGDPELLAHYRALAGDHLEVLAGDKGEADLGLDR QTWQRLADTVDLIVDPAALVNHVLPYSQLFGPNALGTAELLRLALTSK IKPYSYTSTIGVADQIPPSAFTEDADIRVISATRAVDDSYANGYSNSKW AGEVLLREAHDLCGLPVAVFRCDMILADTTWAGQLNVPDMFTRMILS LAATGIAPGSFYELAADGARQRAHYDGLPVEFIAEAISTLGAQSQDGFH TYHVMNPYDDGIGLDEFVDWLNESGCPIQRIADYGDWLQRFETALRA LPDRQRHSSLLPLLHNYRQPERPVRGSIAPTDRFRAAVQEAKIGPDKDI PHVGAPHVKYVSDLRLLGLL |
| 3 | Mycobacterium smegmatis | ABK71854.1 | MTSDVHDATDGVTETALDDEQSTRRIAELYATDPEFAAAAPLPAVVD AAHKPGLRLAEILQTLFTGYGDRPALGYRARELATDEGGRTVTRLLPR FDTLTYAQVWSRVQAVAAALRHNFAQPIYPGDAVATIGFASPDYLTLD LVCAYLGLVSVPLQHNAPVSRLAPILAEVEPRILTVSAEYLDLAVESVR DVNSVSQLVVFDHHPEVDDHRDALARAREQLAGKGIAVTTLDAIADE GAGLPAEPIYTADHDQRLAMILYTSGSTGAPKGAMYTEAMVARLWT MSFITGDPTPVINVNFMPLNHLGGRIPISTAVQNGGTSYFVPESDMSTLF EDLALVRPTELGLPRVADMLYQHHLATVDRLVTQGADELTAEKQAA GAELREQVLGGRVITGFVSTAPLAAEMRAFLDJTLGAHIVDGYGLTET GAVTRDGVIVRPPVIDYKLIDVPELGYFSTDKPYRGELLVRSQTLTPG YYKRPEVTASVFDRDGYYHTGDVMAETAPDHLVYVDRRNNVLKLAQ GEFVAVANLEAVFSGAALVRQIFVYGNSERSFLLAVVVPTPEALEQYD PAALKAALADSLQRTARDAELQSYEVPADFIVETEPFSAANGLLSGVG KLLRPNLKDRYGQRLEQMYADIAATQANQLRELRRAAATQPVIDTLT QAAAATILGTGSEVASDAHFTDLGGDSLSALTLSNLLSDFFGFEVPVGTI VNPATNLAQLAQHIEAQRTAGDRRPSPTTVHGADATEIRASELTLDKFI DAETLRAAPGLPKVTTEPRTVLLSGANGWLGRFLTLQWLERLAPVGG TLITIVRGRDDAAARARLTQAYDTDPELSRRFAELADRHLRVVAGDIG DPNLGLTPEIWHRLAAEVDLVVHPAALVNHVLPYRQLFGPNVVGTAE VIKLALTERIKPVTYLSTVSVAMGIPDFEEDGDIRTVSPVRPLDGGYAN GYGNSKWAGEVLLREAHDLCGLPVATFRSDMILAHPRYRGQVNVPD MFTRLLLSLLITGVAPRSFYIGDGERPRAHYPGLTVDFVAEAVTTLGAQ QREGYVSYDVMNPHDDGISLDVFVDWLIRAGHPIDRVDDYDDWVRRF ETALTALPEKRRAQTVLPLLHAFRAPQAPLRGAPEPTEVFHAAVRTAK VGPGDIPHLDEALIDKYIRDLREFGLI |

Fig 8B

| SEQ ID NO | Organism | GENBANK reference | Amino acid sequence |
|---|---|---|---|
| 4 | *Segniliparus rugosus* | EFV11917.1 | MGDGEERAKRFFQRIGELSATDPQFAAAAPDPAVVEAVSDPSLSFTRY LDTLMRGYAERPALAHRVGAGYETISYGELWARVGAIAAAWQADGL APGDFVATVGFTSPDYVAVDLAAARSGLVSVPLQAGASLAQLVGILEE TEPKVLAASASSLEGAVACALAAPSVQRLVVFDLRGPDASESAADERR GALADAEEQLARAGRAVVVETLADLAARGEALPEAPLFEPAEGEDPL ALLIYTSGSTGAPKGAMYSQRLVSQLWGRTPVVPGMPNISLHYMPLSH SYGRAVLAGALSAGGTAHFTANSDLSTLFEDIALARPTFLALVPRVCE MLFQESQRGQDVAELRERVLGGRLLVAVCGSAPLSPEMRAFMEEVLG FPLLDGYGSTEALGVMRNGIIQRPPVIDYKLVDVPELGYRTTDKPYPRG ELCIRSTSLISGYYKRPEITAEVFDAQGYYKTGDVMAEIAPDHLVYVDR SKNVLKLSQGEFVAVAKLEAAYGTSPYVKQIFVYGNSERSFLLAVVVP NAEVLGARDQEEAKPLIAASLQKIAKEAGLQSYEVPRDFLIETEPFTTQ NGLLSEVGKLLRPKLKARYGEALEARYDEIAHGQADELRALRDGAGQ RPVVETVVRAAVAISGSEGAEVGPEANFADLGGDSLSALSLANLLHDV FEVEVPVRIIIGPTASLAGIAKHIEAERAGASAPTAASVHGAGATRIRAS ELTLEKFLPEDLLAAAKGLPAADQVRTVLLTGANGWLGRFLALEQLE RLARSGQDGGKLICLVRGKDAAAARRRIEEETLGTDPALAARFAELAEG RLEVVPGDVGEPKFGLDDAAWDRLAEEVDVIVHPAALVNHVLPYHQL FGPNVVGTAEIIRLAITAKRKPVTYLSTVAVAAGVEPSSFEEDGDIRAV VPERPLGDGYANGYGNSKWAGEVLLREAHELVGLPVAVFRSDMILAH TRYTGQLNVPDQFTRLVLSLLATGIAPKSFYQQGAAGERQRAHYDGIP VDFTAEAITTLGAEPSWFDGGAGFRSFDVFNPHHDGVGLDEFVDWLIE AGHPISRIDDHKEWFARFETAVRGLPEAQRQHSLLPLLRAYSFPHPPVD GSVYPTGKFQGAVKAAQVGSDHDVPHLGKALIVKYADDLKALGLL |
| 5 | *Mycobacterium abscessus subsp. bolletii* | EIV11143.1 | MTNETNPQQEQLSRRIESLRESDPQFRAAQPDPAVAEQVLRPGLHLSEA IAALMTGYAERPALGERARELVIDQDGRTTLRLLPRFDTTTYGELWSR TTSVAAAWHHDATHPVKAGDLVATLGFTSIDYTVLDLAIMILGGVAV PLQTSAPASQWTTILAEAEPNTLAVSIELIGAAMESVRATPSIKQVVVFD YTPEVDDQREAFEAASTQLAGTGIALETLDAVIARGAALPAAPLYA PSAGDDPLALLIYTSGSTGAPKGAMHSENIVRRWWIREDVMAGTENLP MIGLNFMPMSHIMGRGTLTSTLSTGGTGYFAASSDMSTLFEDMELIRPT ALALVPRVCDMVFQRFQTEVDRRLASGDTASAEAVAAEVKADIRDNL FGGRVSAVMVGSAPLSEELGEFIESCFELNLTDGYGSTEAGMVFRDGIV QRPPVIDYKLVDVPELGYFSTDKPHPRGELLLKTDGMFLGYYKRPEV TASVFDADGFYMTGDIVAELAHDNIEIIDRRNNVLKLSQGEFVAVATL EAEYANSPVVHQIYVYGSSERSYLLAVVVPTPEAVAAAKGDAAALKT TIADSLQDIAKEIQLQSYEVPRDFIIEPQPFTQGGNGLLTGIAKLARPNLKA HYGPRLEQMYAEIAEQQAAELRALHGVDPDKPALETVLKAAQALLGV SSAELAADAHFTDLGGDSLSALSFSDLLRDIFAVEVPVGVIVSAAND LGGVAKFVDEQRHSGGTRPTAETVHGAGHTEIRAADLTLDKFIDEATL HAAPSLPKAAGIPHTVLLTGSNGYLGHYLALEWLERLDKTDGKLIVIV RGKNAEAAYGRLEEAFDTGDTELLAHFRSLADKHLEVLAGDIGDPNL GLDADTWQRLADTVDVIVHPAALVNHVLPYNQLFGPNVVGTAEIIRKL AITTKIKPVTYLSTVAVAAYVDPTTFDEESDIRLISAVRPIDDGYANGYG NAKWAGEVLLREAHDLCGLPVAVFRSDMILAHSRYTGQLNVPDQFTR LILSLIATGIAPGSFYAQTTGERPLAHYDGLPGDFTAEAITTLGTQVPE GSEGFVTYDCVNPHADGISLDNFVDWLIEAGYPIARIDNYTEWFTRFDT AIRGLSEKQKQHSLLPLLHAFEQPSAAENHGVVPAKRFQHAVQAAGIG PVGQDGTTDIPHLSRRLIVKYAKDLEQLGLL |

Fig 8C

| SEQ ID NO | Organism | GENBANK reference | Amino acid sequence |
|---|---|---|---|
| 6 | Segniliparus rotundus | ADG98140.1 | MTQSHTQGPQASAAHSRLARRAAELLATDPQAAATLPDPEVVRQATR PGLRLAERVDAILSGYADRPALGQRSFQTVKDPITGRSSVELLPTFDTIT YRELRERATAIASDLAHHPQAPAKPGDFLASIGFISVDYVAIDIAGVPA GLTAVPLQTGATLATLTAITAETAPTLFAASIEHLPTAVDAVLATPSVR RLLVFDYRAGSDEDREAVEAAKRKIADAGSSVLVDVLDEVIARGKSAP KAPLPPATDAGDDSLSLLIYTSGSTGTPKGAMYPERNVAHFWGGVWA AAFDEDAAPPVPAINITFLPLSHVASRLSLMPTLARGGLMHFVAKSDLS TLFEDLKLARPTNLFLVPRVVEMLYQHYQSELDRRGVQDGTREAEAV KDDLRTGLLGGRILTAGFGSAPLSAELAGFIESLLQIHLVDGYGSTEAG PVWRDGYLVKPPVTDYKLIDVPELGYFSTDSPHPRGELAIKTQTILPGY YKRPETTAEVFDEDGPYLTGDVVAQIGPEQFAYVDRRKNVLKLSQGEF VTLAKLEAAYSSSPLVRQLFVYGSSERSYLLAVIVPTPDALKKFGVGEA AKAALGESLQKIARDEGLQSYEVPRDFHETDPFTVENGLLSDARKSLRP KLKEHYGERLEAMYKELADGQANELRDIRRGVQQRPTLETVRRAAAA MLGASAAEIKPDAHFTDLGGDSLSALTFSNFLHDLFEVDVPVGVIVSA ANTLGSVAEHIDAQLAGGRARPTFATVHGKGSTTIKASDLTLDKFIDEQ TLEAAKHLPKPADPPRTVLLTGANGWLGRFLALEWLERLAPAGGKLIT IVRGKDAAQAKARLDAAYESGDPKLAGHYQDLAATTLEVLAGDFSEP RLGLDEATWNRLADEVDFISHPGALVNHVLPYNQLFGPNVAGVAEIIK LAITTRIKPVTYLSTVAVAAGVEPSALDEDGDIRTVSAERSVDEGYANG YGNSKWGGEVLLREAHDRTGLPVRVFRSDMILAHQKYTGQVNATDQ FTRLVQSLLATGLAPKSFYELDAQGNRQRAHYDGIPVDFTAESITTLGG DGLEGYRSYNVFNPHRDGVGLDEFVDWLIEAGHPITRIDDYDQWLSRF ETSLRGLPESKRQASVLPLLHAFARPGPAVDGSPFRNTVFRTDVQKAKI GAEHDIPHLGKALVLKYADDIKQLGLL |
| 7 | Chromobacterium violaceum | AAQ59697.1 | MQKQRTTSQWRELDAAHHLHPFTDTASLNQAGARVMTRGEGVYLW DSEGNKIIDGMAGLWCVNVGYGRKDFAEAARRQMEELPFYNTFFKTT HPAVVELSSLLAEVTPAGFDRVFYTNSGSESVDTMIRMVRRYWDVQG KPEKKTLIGRWNGYHGSTIGGASLGGMKYMHEQGDLPIPGMAHIEQP WWYKHGKDMTPDEFGVVAARWLEEKILEIGADKVAAFVGEPIQGAG GVIVPPATYWPEIERICRKYDVLLVADEVICGFGRTGEWFGHQHFGFQP DLFTAAKGLSSGYLPIGAVFVGKRVAEGLIAGGDFNHGFTYSGHPVCA AVAHANVAALRDEGIVQRVKDDIGPYMQKRWRETFSRFEHVDDVRG VGMVQAFTLVKNKAKRELFPDFGEIGTLCRDIFFRNNLIMRACGDHIVS APPLVMTRAEVDEMLAVAERCLEEFEQTLKARGLA |
| 8 | Pseudomonas aeruginosa | AAG08191.1 | MNARLHATSPLGDADLVRADQAHYMHGYHVFDDHRVNGSLNIAAGD GAYIYDTAGNRYLDAVGGMWCTNIGLGREEMARTVAEQTRLLAYSN PFCDMANPRAIELCRKLAELAPGDLDHVFLTTGGSTAVDTAIRLMHYY QNCRGKRAKKHVITRINAYHGSTFLGMSLGGKSADRPAEFDFLDERIH HLACPYYYRAPEGLGEAEFLDGLVDEFERKILELGADRVGAFISEPVFG SGGVIVPPAGYHRRMWELCQRYDVLYISDEVVTSFGRLGHFFASQAVF GVQPDIHLTAKGLTSGYQPLGACIFSRRIWEVIAEPDKGRCFSHGFTYSG HPVACAAALKNIEHEREGLLAHADEVGRYFEERLQSLRDLPIVGDVRG MRFMACVEFVADKASKALFPESLNIGEWVHLRAQKRGLLVRPIVHLN VMSPPLILTREQVDTVVRVLRESIEETVEDLVRAGHR |
| 9 | Pseudomonas syringae | AAY39893.1 | MSANNPQTLEWQALSSEHHLAPFSDYKQLKEKGPRIITRAEGVYLWDS EGNKILDGMSGLWCVAIGYGREELADAASKQMRELPYYNLFFQTAHP PVLELAKAISDIAPEGMNHVFFTGSGSEGNDTMLRMVRHYWALKGQP NKKTIISRVNGYHGSTVAGASLGGMTYMHEQGDLPIPGVVHIPQPYWF GEGGDMTPDEFGIWAAEQLEKKILELGVENVGAFIAEPIQGAGGVIVPP DSYWPKIKEILSRYDILFAADEVICGFGRTSEWFGSDFYGLRPDMMTIA KGLTSGYVPMGGLIVRDEIVAVLNEGGDFNHGFTYSGHPVAAAVALE NIRILREEKIVERVRSETAPYLQKRLRELSDHPLVGEVRGVGLLGAIELV KDKTTRERYTDKGAGMICRTFCFDNGLIMRAVGDTMIIAPPLVISFAQI DELVEKARTCLDLTLAVLQG |
| 10 | Rhodobacter sphaeroides | ABA81135.1 | MTRNDATNAAGAVGAAMRDHILLPAQEMAKLGKSAQPVLTHAEGIY VHTEDGRRLIDGPAGMWCAQVGYGRREIVDAMAHQAMVLPYASPW YMATSPAARLAEKIATLTPGDLNRIFFTTGGSTAVDSALRFSEFYNNVL GRPQKKRIIVRYDGYHGSTALTAACTGRTGNWPNFDIAQDRISFLSSPN PRHAGNRSQEAFLDDLVQEFEDRIESLGPDTIAAFLAEPILASGGVHPPA GYHARFKAICEKHDILYISDEVVTGFGRCGEWFASEKVFGVVPDIITFA KGVTSGYVPLGGLAISEAVLARISGENAKGSWFTNGYTYSNQPVACAA ALANIELMEREGIVDQAREMADYFAAALASLRDLPGVAETRSVGLVG CVQCLLDPTRADGTAEDKAFTLKIDERCFELGLIVRPLGDLCVISPPLIIS RAQIDEMVAIMRQAITEVSAAHGLTAKEPAAV |

Fig 8D

| SEQ ID NO | Organism | GENBANK reference | Amino acid sequence |
|---|---|---|---|
| 11 | Escherichia coli | AAA57874.1 | MNRLPSSASALACSAHALNLIEKRTLDHEEMKALNREVIEYFKEHVNP GPLEYRKSVTAGGDYGAVEWQAGSLNTLVDTQGQEPIDCLGGPGIFN VGHRNPVVVSAVQNQLAKQPLHSQELLDPLRAMLAKTLAALTPGKLK YSFFCNSGTESVEAALKLAKAYQSPRGKFTFIATSGAFHGKSLGALSAT AKSTFRKPFMPLLPGFRHVPFGNIEAMRTALNECKKTGDDVAAVILEPI QGEGGVILPPPGYLTAVRKLCDEFGALMILDEVQTGMGRTGKMFACE HENVQPDILCLAKALGGGVMPIGATIATEEVFSVLFDNPFLHTTTFGGN PLACAAALATINVLLEQNLPAQAEQKGDMLLDGFRQLAREYPDLVQE ARGKGMLMAJEFVDNEIGYNFASEMFRQRVLVAGTLNNAKTIRJEPPL TLTIEQCELVIKAARKALAAMRVSVEEA |
| 12 | Vibrio fluvialis | AEA39183.1 | MNKPQSWEARAETYSLYGFTDMPSLHQRGTVVVTHGEGPYIVDVNGR RYLDANSGLWNMVAGFDHKGLIDAAKAQYERFPGYHAFFGRMSDQT VMLSEKLVEVSPFDSGRVFYTNSGSEANDTMVKMLWFLHAAEGKPQ KRKILTRWNAYHGVTAVSASMTGKPYNSVFGLPLPGFVHLT CPHYWRYGEEGETEEQFVARLARELEETIQREGADTIAGFFAEPVMGA GGVIPPAKGYFQAILPILRKYDIPVISDEVICGFGRTGNTWGCVTYDFTP DAHSSKNLTAGFPMGAVILGPELSKRLETAIEAIEEFPHGFTASGHPVG CAIALKAIDVVMNEGLAENVRRLAPRFEERLKHIAERPNIGEYRGIGFM WALEAVKDKASKTPFDGNLSVSERIANTCTDLGLICRPLGQSVVLCPPF ILTEAQMDEMFDKLEKALDKVFAEVA |
| 13 | Escherichia coli | AAC74479.1 | MREAFICDGIRTPIGRYGGALSSVRADDLAAIPLRELLVRNPRLDAECID DVILGCANQAGEDNRNVARMATLLAGLPQSVSGTTINRLCGSGLDAL GFAARAIKAGDGDLLIAGGVESMSRAPFVMGKAASAFSRQAEMFDTTI GWRFVNPLMAQQFGTDSMPETAENVAELLKISREDQDSFALRSQQRT AKAQSSGILAEEIVPVVLKNKKGVVTEIQHDEHLRPETTLEQLRGLKA PFRANGVITAGNASGVNDGAAALIASEQMAAAQGLTPRARIVAMATA GVEPRLMGLGPVPATRRVLERAGLSIHDMDVIELNEAFAAQALGVLRE LGLPDDAPHVNPNGGAIALGHPLGMSGARLALAASHELHRRNGRYAL CTMCIGVGQGIAMILERV |
| 14 | Bacillus subtilis | CAA74523.1 | MSKAKITAIGTYAPSRRLTNADLEKIVDTSDEWIVQRTGMRERRIADEH QFTSDLCIEAVKNLKSRYKGTLDDVDMILVATTTSDYAFPSTACRVQE YFPGWESTGALDINATCAGLTYGLHLANGLITSGLHQKILVIAGETLSKV TDYTDRTTCVLFGDAAGALLVERDEETPGFLASVQGTSGNGGDILYRA GLRNEINGVQLVGSGKMVQNGREVYKWAARTVPGEFERLLHKAGLS SDDDLDWFVPHSANLRMIESICEKTPFPIEKTLTSVEHYGNTSSVSIVLAL DLAVKAGKLKKDQIVLLFGFGGGLTYTGLLIKWGM |
| 15 | Mycobacterium smegmatis | ABK75684.1 | MTIETREDRFNRRIDHLFETDPQFAAARPDEAISAAAADPELRLPAAVK QILAGYADRPALGKRAVEFVTDEEGRTTAKLLPRFDTITYRQLAGRIQA VTNAWHNHPVNAGDRVAILGFTSVDYTTIDIALLELGAVSVPLQTSAP VAQLQPIVAETEPKVIASSVDFLADAVALVESGPAPSRLVVFDYSHEVD DQREAFEAAKGKLAGTGVVVETITDALDRGRSLADAPLYVPDEAD PLTLLIYTSGSTGTPKGAMYPESKTATMWQAGSKARWDETLGVMPSIT LNFMPMSHVMGRGILCSTLASGGTAYFAARSDLSTFLEDLALVRPTQL NFVPRIWDMLFQEYQSRLDNRRAEGSEDRAEAAVLEEVRTQLLGGRF VSALTGSAPISAEMKSWVEDLLDMHLLEGYGSTEAGAVFIDGQIQRPP VIDYKLVDVPDLGYFATDRPYPRGELLVKSEQMFPGYYKRPEITAEMF DEDGYYRTGDIVAELGPDHLEYLDRRNNVLKLSQGEFVTVSKLEAVF GDSPLVRQIYVYGNSARSYLLAVVVPTEEALSRWDGDELKSRISDSLQ DAARAAGLQSYEIPRDFLVETTPFTLENGLLTGIRKLARPKLKAHYGER LEQLYTDLAEGQANELRELRRNGADRPVVETVSRAAVALLGASVTDL RSDAHFTDLGGDSLSALSFSNLLHEIFDVDVPVGVIVSPATDLAGVAAY IEGELRGSKRPTYASVHGRDATEVRARDLALGKFIDAKTLSAAPGLPRS GTEIRTVLLTGATGFLGRYLALEWLERMDLVDGKVICLVRARSDDEAR ARLDATFDTGDATLLEHYRALAADHLEVIAGDKGEADLGLDHDTWQ RLADTVDLIVDPAALVNHVLPYSQMFGPNALGTAELIRIALTTTIKPYV YVSTIGVGQGISPEAFVEDADIREISATRRVDDSYANGYGNSKWAGEV LLREAHDWCGLPVSVFRCDMILADTTYSGQLNLPDMFTRLMLSLVAT GIAPGSFYELDADGNRQRAHYDGLPVEFIAEAISTIGSQVTDGFETFHV MNPYDDGIGLDEYVDWLIEAGYPVHRVDDYATWLSRFETALRALPER QRQASLLPLLHNYQQPSPPVCGAMAPTDRFRAAVQDAKIGPDKDIPHV TADVIVKYISNLQMLGLL |

Fig 8E

| SEQ ID NO | Organism | GENBANK reference | Amino acid sequence |
|---|---|---|---|
| 16 | Cupriavidus necator | AAC38322.1 | MTREVVVVSGVRTAIGTFGGSLKDVAPAELGALVVREALARAQVSGD DVGHVVFGNVIQTEPRDMYLGRVAAVNGGVTINAPALTVNRLCGSGL QAIVSAAQTILLGDTDVAIGGGAESMSRAPYLAPAARWGARMGDAGL VDMMLGALHDPFHRIHMGVTAENVAKEYDISRAQQDEAALESHRRAS AAIKAGYFKDQIVPVVSKGRKGDVTFDTDEHVRHDATIDDMTKLRPV FVKENGTVTAGNASGLNDAAAAVVMMERAEAERRGLKPLARLVSYH AGVDPKAMGIGPVPATKIALERAGLQVSDLDVIEANEAFAAQACAVT KALGLDPAKVNPNGSGISLGHPIGATGALITVKALHELNRVQGRYALV TMCIGGGQGIAAIFERI |
| 17 | Escherichia coli | AAC74479.1 | MREAFICDGIRTPIGRYGGALSSVRADDLAAIPLRELLVRNPRLDAECID DVILGCANQAGEDNRNVARMATLLAGLPQSVSGTTINRLCGSGLDAL GFAARAIKAGDGDLLIAGGVESMSRAPFVMGKAASAFSRQAEMFDTTI GWRFVNPLMAQQFGTDSMPETAENVAELLKISREDQDSFALRSQQRT AKAQSSGILAEEIVPVVLKNKKGVVTEIQHDEHLRPETTLEQLRGLKAP FRANGVITAGNASGVNDGAAALIIASEQMAAAQGLTPRARIVAMATA GVEPRLMGLGPVPATRRVLERAGLSIHDMDVIELNEAFAAQALGVLRE LGLPDDAPHVNPNGGAIALGHPLGMSGARLALAASHELHRRNGRYAL CTMCIGVGQGIAMILERV |
| 18 | Clostridium propionicum | CAB77207.1 | MRKVPIITADEAAKLIKDGDTVTTSGFVGNAIPEALDRAVEKRFLETGE PKNITYVYCGSQGNRDGRGAEHFAHEGLLKRYIAGHWATVPALGKM AMENKMEAYNVSQGALCHLFRDIASHKPGVFTKVGIGTFIDPRNGGG KVNDITKEDIVELVEIKGQEYLFYPAFPIHVALIRGTYADESGNITFEKE VAPLEGTSVCQAVKNSGGIVVVQVERVVKAGTLDPRHVKVPGIYVDY VVVADPEDHQQSLDCEYDPALSGEHRRPEVVGEPLPLSAKKVIGRRGA IELEKDVAVNLGVGAPEYVASVADEEGIVDFMTLTAESGAIGGVPAGG VRFGASYNADALIDQGYQFDYYDGGGLDLCYLGLAECDEKGNINVSR FGPRIAGCGGFINITQNTPKVFFCGTFTAGGLKVKIEDGKVIIVQEGKQK KFLKAVEQITFNGDVALANKQQVTYITERCVFLLKEDGLHLSEIAPGID LQTQILDVMDFAPIIDRDANGQIKLMDAALFAEGLMGLKEMKS |
| 19 | Clostridium aminobutyricum | CAB60036.2 | MDWKKIYEDRTCTADEAVKSIKSGDRVLFAHCVAEPPVLVEAMVANA AAYKNVTVSHMVTLGKGEYSKPEYKENFTFEGWFTSPSTRGSIAEGHG QFVPVFFHEVPSLIRKDIFHVDVFMVMVSPPDHNGFCCVGVSSDYTMQ AIKSAKIVLAEVNDQVPVVYGDTFVHVSEIDKFVETSHPLPEIGLPKIGE VEAAIGKHCASLIEDGSTLQLGIGAIPDAVLSQLKDKKHLGIHSEMISDG VVDLYEAGVIDCSQKSIDKGKMAITFLMGTKRLYDFAANNPKVELKP VDYINHPSVVAQCSKMVCINACLQVDFMGQIVSDSIGTKQFSGVGGQV DFVRGASMSIDGKGKAHAMPSVAKKKDGSMISKIVPFIDHGAAVTTSR NDADYVVTEYGIAEMKGKSLQDRARALINIAHPDFKDELKAEFEKRFN AAF |
| 20 | Citrobacter sp. A1 | EJF23789.1 | MKRMSAEQAAEHQHDDMVAFSGFTPAGSPKALPTAIAQRACEQHQN GQPFQIRLLTGASIGAAADDVLSAADAVSWRAPYQTSSGLRDKINQGQ VRFVDLHLSEVAQMVNYGFFGEIDVAVIEASAIAPDGRIWLSSGIGNAP TWLLRAKKVHELNHYHNPRVAEFADIVIPGAPPRRNSVPIFHTMDRVG SQCVQIDPKKVVAVVDTELPDAGNASDKTNPVSQQIADNVVSFLLAE MAHKRIPAEFLPLQSGVGNINNAVMARLGENPDIPPFMMYSEVLQESV VHLLETGKISGASASSLTISAPSLQKIYDNMDFFASRIVLRPQEISNNPEH RRLGVIALNVGLEFDIYGHANSTHVAGVNLMNGIGGSGDFERNAYLSI FMAPSIAKGGKISTIVPMCSHVDHSEHSVKVIVTEQGIADLRGLSPMQR AHTHNNCAHPLYRDYLHRYLEKAPGGHHHDLSHAFDLHRNLLETGS MLG |
| 21 | Acetobacter aceti | ACD85596.1 | MTERIRNVALRSKVCPAETASELIKHGDVVGTSGFTGAGYPKEVPKAL AQRMEAAHDRGEKYQISLITGASTGFQLDGELAKANGVYFRSPFNTDA TMRRNRINAGETEYFDNHLGQVAGRAVQGNYGKFNIALVEATAITEDG GIVPTSSVGNSQTFLNLAEKVHEVNEWQNPMLEGIHDIWDGNVSGVPT RDIVPIVRADQRVGGPVLRVNPDKIAAIVRTNDRDRNAPFAAPDETAK AIAGYLLDFFGHEVKQNRLPPSLLPLQSGVGNVANAVLEGLKEGPFEN LVGYSEVIQDGMLAMLDSGRMRIASASSFSLSPEAAEEINNRMDFFRSK HLRQQDVSNSPGHRRLGCIAMNGMIEADIYGNVNSTRVMGSKMMNGI GGSGDFARSSYLSIFLSPSTAKGGKISAIVPMAAHVDHIMQDAQIFVTE QGLADLRGLSPVQRAREHSKCAHPDYRPMLQDYFDRALKNSFGKHTP HLLTEALSWHQRFIDTGTMLPS |

SEQUENCE LISTING

<160> NUMBER OF SEQ ID NOS: 22

<210> SEQ ID NO 1
<211> LENGTH: 393
<212> TYPE: PRT
<213> ORGANISM: Cupriavidus necator

<400> SEQUENCE: 1

```
Met Thr Arg Glu Val Val Val Ser Gly Val Arg Thr Ala Ile Gly
1               5                   10                  15

Thr Phe Gly Gly Ser Leu Lys Asp Val Ala Pro Ala Glu Leu Gly Ala
            20                  25                  30

Leu Val Val Arg Glu Ala Leu Ala Arg Ala Gln Val Ser Gly Asp Val
        35                  40                  45

Gly His Val Val Phe Gly Asn Val Ile Gln Thr Glu Pro Arg Asp Met
    50                  55                  60

Tyr Leu Gly Arg Val Ala Val Asn Gly Val Thr Ile Asn Ala
65                  70                  75                  80

Pro Ala Leu Thr Val Asn Arg Leu Cys Gly Ser Gly Leu Gln Ala Ile
                85                  90                  95

Val Ser Ala Ala Gln Thr Ile Leu Leu Gly Asp Thr Asp Val Ala Ile
                100                 105                 110

Gly Gly Gly Ala Glu Ser Met Ser Arg Ala Pro Tyr Leu Ala Pro Ala
            115                 120                 125

Ala Arg Trp Gly Ala Arg Met Gly Asp Ala Gly Leu Val Asp Met Met
130                 135                 140

Leu Gly Ala Leu His Asp Pro Phe His Arg Ile His Met Gly Val Thr
145                 150                 155                 160

Ala Glu Asn Val Ala Lys Glu Tyr Asp Ile Ser Arg Ala Gln Gln Asp
                165                 170                 175

Glu Ala Ala Leu Glu Ser His Arg Arg Ala Ser Ala Ala Ile Lys Ala
            180                 185                 190

Gly Tyr Phe Lys Asp Gln Ile Val Pro Val Val Ser Lys Gly Arg Lys
        195                 200                 205

Gly Asp Val Thr Phe Asp Thr Asp Glu His Val Arg His Asp Ala Thr
    210                 215                 220

Ile Asp Asp Met Thr Lys Leu Arg Pro Val Phe Val Lys Glu Asn Gly
225                 230                 235                 240

Thr Val Thr Ala Gly Asn Ala Ser Gly Leu Asn Asp Ala Ala Ala Ala
                245                 250                 255

Val Val Met Met Glu Arg Ala Glu Ala Glu Arg Arg Gly Leu Lys Pro
            260                 265                 270

Leu Ala Arg Leu Val Ser Tyr Gly His Ala Gly Val Asp Pro Lys Ala
        275                 280                 285

Met Gly Ile Gly Pro Val Pro Ala Thr Lys Ile Ala Leu Glu Arg Ala
    290                 295                 300

Gly Leu Gln Val Ser Asp Leu Asp Val Ile Glu Ala Asn Glu Ala Phe
305                 310                 315                 320

Ala Ala Gln Ala Cys Ala Val Thr Lys Ala Leu Gly Leu Asp Pro Ala
                325                 330                 335

Lys Val Asn Pro Asn Gly Ser Gly Ile Ser Leu Gly His Pro Ile Gly
            340                 345                 350

Ala Thr Gly Ala Leu Ile Thr Val Lys Ala Leu His Glu Leu Asn Arg
        355                 360                 365

Val Gln Gly Arg Tyr Ala Leu Val Thr Met Cys Ile Gly Gly Gly Gln
    370                 375                 380

Gly Ile Ala Ala Ile Phe Glu Arg Ile
385                 390
```

<210> SEQ ID NO 2
<211> LENGTH: 1173
<212> TYPE: PRT
<213> ORGANISM: Mycobacterium marinum

<400> SEQUENCE: 2

```
Met Ser Pro Ile Thr Arg Glu Glu Arg Leu Glu Arg Arg Ile Gln Asp
1               5                   10                  15

Leu Tyr Ala Asn Asp Pro Gln Phe Ala Ala Ala Lys Pro Ala Thr Ala
            20                  25                  30

Ile Thr Ala Ala Ile Glu Arg Pro Gly Leu Pro Leu Pro Gln Ile Ile
        35                  40                  45

Glu Thr Met Thr Gly Tyr Ala Asp Arg Pro Ala Leu Ala Gln Arg Ser
    50                  55                  60

Val Glu Phe Val Thr Asp Ala Gly Thr Gly His Thr Thr Leu Arg Leu
65                  70                  75                  80

Leu Pro His Phe Glu Thr Ile Ser Tyr Gly Glu Leu Trp Asp Arg Ile
                85                  90                  95

Ser Ala Leu Ala Asp Val Leu Ser Thr Glu Gln Thr Val Lys Pro Gly
            100                 105                 110

Asp Arg Val Cys Leu Leu Gly Phe Asn Ser Val Asp Tyr Ala Thr Ile
        115                 120                 125

Asp Met Thr Leu Ala Arg Leu Gly Ala Val Ala Val Pro Leu Gln Thr
    130                 135                 140

Ser Ala Ala Ile Thr Gln Leu Gln Pro Ile Val Ala Glu Thr Gln Pro
145                 150                 155                 160

Thr Met Ile Ala Ala Ser Val Asp Ala Leu Ala Asp Ala Thr Glu Leu
                165                 170                 175

Ala Leu Ser Gly Gln Thr Ala Thr Arg Val Leu Val Phe Asp His His
            180                 185                 190

Arg Gln Val Asp Ala His Arg Ala Ala Val Glu Ser Ala Arg Glu Arg
        195                 200                 205

Leu Ala Gly Ser Ala Val Val Glu Thr Leu Ala Glu Ala Ile Ala Arg
    210                 215                 220

Gly Asp Val Pro Arg Gly Ala Ser Ala Gly Ser Ala Pro Gly Thr Asp
225                 230                 235                 240

Val Ser Asp Asp Ser Leu Ala Leu Leu Ile Tyr Thr Ser Gly Ser Thr
                245                 250                 255

Gly Ala Pro Lys Gly Ala Met Tyr Pro Arg Arg Asn Val Ala Thr Phe
            260                 265                 270

Trp Arg Lys Arg Thr Trp Phe Glu Gly Gly Tyr Glu Pro Ser Ile Thr
        275                 280                 285

Leu Asn Phe Met Pro Met Ser His Val Met Gly Arg Gln Ile Leu Tyr
    290                 295                 300

Gly Thr Leu Cys Asn Gly Gly Thr Ala Tyr Phe Val Ala Lys Ser Asp
305                 310                 315                 320

Leu Ser Thr Leu Phe Glu Asp Leu Ala Leu Val Arg Pro Thr Glu Leu
                325                 330                 335

Thr Phe Val Pro Arg Val Trp Asp Met Val Phe Asp Glu Phe Gln Ser
            340                 345                 350

Glu Val Asp Arg Arg Leu Val Asp Gly Ala Asp Arg Val Ala Leu Glu
        355                 360                 365

Ala Gln Val Lys Ala Glu Ile Arg Asn Asp Val Leu Gly Gly Arg Tyr
    370                 375                 380
```

```
Thr Ser Ala Leu Thr Gly Ser Ala Pro Ile Ser Asp Glu Met Lys Ala
385                 390                 395                 400

Trp Val Glu Glu Leu Leu Asp Met His Leu Val Glu Gly Tyr Gly Ser
            405                 410                 415

Thr Glu Ala Gly Met Ile Leu Ile Asp Gly Ala Ile Arg Arg Pro Ala
            420                 425                 430

Val Leu Asp Tyr Lys Leu Val Asp Val Pro Asp Leu Gly Tyr Phe Leu
            435                 440                 445

Thr Asp Arg Pro His Pro Arg Gly Glu Leu Leu Val Lys Thr Asp Ser
450                 455                 460

Leu Phe Pro Gly Tyr Tyr Gln Arg Ala Glu Val Thr Ala Asp Val Phe
465                 470                 475                 480

Asp Ala Asp Gly Phe Tyr Arg Thr Gly Asp Ile Met Ala Glu Val Gly
            485                 490                 495

Pro Glu Gln Phe Val Tyr Leu Asp Arg Arg Asn Asn Val Leu Lys Leu
            500                 505                 510

Ser Gln Gly Glu Phe Val Thr Val Ser Lys Leu Glu Ala Val Phe Gly
            515                 520                 525

Asp Ser Pro Leu Val Arg Gln Ile Tyr Ile Tyr Gly Asn Ser Ala Arg
530                 535                 540

Ala Tyr Leu Leu Ala Val Ile Val Pro Thr Gln Glu Ala Leu Asp Ala
545                 550                 555                 560

Val Pro Val Glu Glu Leu Lys Ala Arg Leu Gly Asp Ser Leu Gln Glu
            565                 570                 575

Val Ala Lys Ala Ala Gly Leu Gln Ser Tyr Glu Ile Pro Arg Asp Phe
            580                 585                 590

Ile Ile Glu Thr Thr Pro Trp Thr Leu Glu Asn Gly Leu Leu Thr Gly
            595                 600                 605

Ile Arg Lys Leu Ala Arg Pro Gln Leu Lys Lys His Tyr Gly Glu Leu
            610                 615                 620

Leu Glu Gln Ile Tyr Thr Asp Leu Ala His Gly Gln Ala Asp Glu Leu
625                 630                 635                 640

Arg Ser Leu Arg Gln Ser Gly Ala Asp Ala Pro Val Leu Val Thr Val
            645                 650                 655

Cys Arg Ala Ala Ala Leu Leu Gly Gly Ser Ala Ser Asp Val Gln
            660                 665                 670

Pro Asp Ala His Phe Thr Asp Leu Gly Gly Asp Ser Leu Ser Ala Leu
            675                 680                 685

Ser Phe Thr Asn Leu Leu His Glu Ile Phe Asp Ile Glu Val Pro Val
690                 695                 700

Gly Val Ile Val Ser Pro Ala Asn Asp Leu Gln Ala Leu Ala Asp Tyr
705                 710                 715                 720

Val Glu Ala Ala Arg Lys Pro Gly Ser Ser Arg Pro Thr Phe Ala Ser
            725                 730                 735

Val His Gly Ala Ser Asn Gly Gln Val Thr Glu Val His Ala Gly Asp
            740                 745                 750

Leu Ser Leu Asp Lys Phe Ile Asp Ala Ala Thr Leu Ala Glu Ala Pro
            755                 760                 765

Arg Leu Pro Ala Ala Asn Thr Gln Val Arg Thr Val Leu Leu Thr Gly
            770                 775                 780

Ala Thr Gly Phe Leu Gly Arg Tyr Leu Ala Leu Glu Trp Leu Glu Arg
785                 790                 795                 800

Met Asp Leu Val Asp Gly Lys Leu Ile Cys Leu Val Arg Ala Lys Ser
```

```
            805                 810                 815
Asp Thr Glu Ala Arg Ala Arg Leu Asp Lys Thr Phe Asp Ser Gly Asp
            820                 825                 830

Pro Glu Leu Leu Ala His Tyr Arg Ala Leu Ala Gly Asp His Leu Glu
        835                 840                 845

Val Leu Ala Gly Asp Lys Gly Glu Ala Asp Leu Gly Leu Asp Arg Gln
    850                 855                 860

Thr Trp Gln Arg Leu Ala Asp Thr Val Asp Leu Ile Val Asp Pro Ala
865                 870                 875                 880

Ala Leu Val Asn His Val Leu Pro Tyr Ser Gln Leu Phe Gly Pro Asn
                885                 890                 895

Ala Leu Gly Thr Ala Glu Leu Leu Arg Leu Ala Leu Thr Ser Lys Ile
            900                 905                 910

Lys Pro Tyr Ser Tyr Thr Ser Thr Ile Gly Val Ala Asp Gln Ile Pro
        915                 920                 925

Pro Ser Ala Phe Thr Glu Asp Ala Asp Ile Arg Val Ile Ser Ala Thr
    930                 935                 940

Arg Ala Val Asp Asp Ser Tyr Ala Asn Gly Tyr Ser Asn Ser Lys Trp
945                 950                 955                 960

Ala Gly Glu Val Leu Leu Arg Glu Ala His Asp Leu Cys Gly Leu Pro
                965                 970                 975

Val Ala Val Phe Arg Cys Asp Met Ile Leu Ala Asp Thr Thr Trp Ala
            980                 985                 990

Gly Gln Leu Asn Val Pro Asp Met Phe Thr Arg Met Ile Leu Ser Leu
        995                 1000                1005

Ala Ala Thr Gly Ile Ala Pro Gly Ser Phe Tyr Glu Leu Ala Ala
    1010                1015                1020

Asp Gly Ala Arg Gln Arg Ala His Tyr Asp Gly Leu Pro Val Glu
    1025                1030                1035

Phe Ile Ala Glu Ala Ile Ser Thr Leu Gly Ala Gln Ser Gln Asp
    1040                1045                1050

Gly Phe His Thr Tyr His Val Met Asn Pro Tyr Asp Asp Gly Ile
    1055                1060                1065

Gly Leu Asp Glu Phe Val Asp Trp Leu Asn Glu Ser Gly Cys Pro
    1070                1075                1080

Ile Gln Arg Ile Ala Asp Tyr Gly Asp Trp Leu Gln Arg Phe Glu
    1085                1090                1095

Thr Ala Leu Arg Ala Leu Pro Asp Arg Gln Arg His Ser Ser Leu
    1100                1105                1110

Leu Pro Leu Leu His Asn Tyr Arg Gln Pro Glu Arg Pro Val Arg
    1115                1120                1125

Gly Ser Ile Ala Pro Thr Asp Arg Phe Arg Ala Ala Val Gln Glu
    1130                1135                1140

Ala Lys Ile Gly Pro Asp Lys Asp Ile Pro His Val Gly Ala Pro
    1145                1150                1155

Ile Ile Val Lys Tyr Val Ser Asp Leu Arg Leu Leu Gly Leu Leu
    1160                1165                1170
```

<210> SEQ ID NO 3
<211> LENGTH: 1173
<212> TYPE: PRT
<213> ORGANISM: Mycobacterium smegmatis

<400> SEQUENCE: 3

-continued

```
Met Thr Ser Asp Val His Asp Ala Thr Asp Gly Val Thr Glu Thr Ala
1               5                  10                 15

Leu Asp Asp Glu Gln Ser Thr Arg Arg Ile Ala Glu Leu Tyr Ala Thr
                20                 25                 30

Asp Pro Glu Phe Ala Ala Ala Pro Leu Pro Ala Val Val Asp Ala
            35                 40                 45

Ala His Lys Pro Gly Leu Arg Leu Ala Glu Ile Leu Gln Thr Leu Phe
        50                 55                 60

Thr Gly Tyr Gly Asp Arg Pro Ala Leu Gly Tyr Arg Ala Arg Glu Leu
65                 70                 75                 80

Ala Thr Asp Glu Gly Gly Arg Thr Val Thr Arg Leu Leu Pro Arg Phe
                85                 90                 95

Asp Thr Leu Thr Tyr Ala Gln Val Trp Ser Arg Val Gln Ala Val Ala
            100                105                110

Ala Ala Leu Arg His Asn Phe Ala Gln Pro Ile Tyr Pro Gly Asp Ala
        115                120                125

Val Ala Thr Ile Gly Phe Ala Ser Pro Asp Tyr Leu Thr Leu Asp Leu
    130                135                140

Val Cys Ala Tyr Leu Gly Leu Val Ser Val Pro Leu Gln His Asn Ala
145                150                155                160

Pro Val Ser Arg Leu Ala Pro Ile Leu Ala Glu Val Glu Pro Arg Ile
            165                170                175

Leu Thr Val Ser Ala Glu Tyr Leu Asp Leu Ala Val Glu Ser Val Arg
            180                185                190

Asp Val Asn Ser Val Ser Gln Leu Val Val Phe Asp His His Pro Glu
            195                200                205

Val Asp Asp His Arg Asp Ala Leu Ala Arg Ala Arg Glu Gln Leu Ala
    210                215                220

Gly Lys Gly Ile Ala Val Thr Thr Leu Asp Ala Ile Ala Asp Glu Gly
225                230                235                240

Ala Gly Leu Pro Ala Glu Pro Ile Tyr Thr Ala Asp His Asp Gln Arg
            245                250                255

Leu Ala Met Ile Leu Tyr Thr Ser Gly Ser Thr Gly Ala Pro Lys Gly
            260                265                270

Ala Met Tyr Thr Glu Ala Met Val Ala Arg Leu Trp Thr Met Ser Phe
        275                280                285

Ile Thr Gly Asp Pro Thr Pro Val Ile Asn Val Asn Phe Met Pro Leu
        290                295                300

Asn His Leu Gly Gly Arg Ile Pro Ile Ser Thr Ala Val Gln Asn Gly
305                310                315                320

Gly Thr Ser Tyr Phe Val Pro Glu Ser Asp Met Ser Thr Leu Phe Glu
            325                330                335

Asp Leu Ala Leu Val Arg Pro Thr Glu Leu Gly Leu Val Pro Arg Val
            340                345                350

Ala Asp Met Leu Tyr Gln His His Leu Ala Thr Val Asp Arg Leu Val
        355                360                365

Thr Gln Gly Ala Asp Glu Leu Thr Ala Glu Lys Gln Ala Gly Ala Glu
    370                375                380

Leu Arg Glu Gln Val Leu Gly Gly Arg Val Ile Thr Gly Phe Val Ser
385                390                395                400

Thr Ala Pro Leu Ala Ala Glu Met Arg Ala Phe Leu Asp Ile Thr Leu
            405                410                415

Gly Ala His Ile Val Asp Gly Tyr Gly Leu Thr Glu Thr Gly Ala Val
```

-continued

```
                420                 425                 430
Thr Arg Asp Gly Val Ile Val Arg Pro Val Ile Asp Tyr Lys Leu
            435                 440                 445
Ile Asp Val Pro Glu Leu Gly Tyr Phe Ser Thr Asp Lys Pro Tyr Pro
450                 455                 460
Arg Gly Glu Leu Leu Val Arg Ser Gln Thr Leu Thr Pro Gly Tyr Tyr
465                 470                 475                 480
Lys Arg Pro Glu Val Thr Ala Ser Val Phe Asp Arg Asp Gly Tyr Tyr
            485                 490                 495
His Thr Gly Asp Val Met Ala Glu Thr Ala Pro Asp His Leu Val Tyr
            500                 505                 510
Val Asp Arg Arg Asn Asn Val Leu Lys Leu Ala Gln Gly Glu Phe Val
            515                 520                 525
Ala Val Ala Asn Leu Glu Ala Val Phe Ser Gly Ala Ala Leu Val Arg
            530                 535                 540
Gln Ile Phe Val Tyr Gly Asn Ser Glu Arg Ser Phe Leu Leu Ala Val
545                 550                 555                 560
Val Val Pro Thr Pro Glu Ala Leu Glu Gln Tyr Asp Pro Ala Ala Leu
            565                 570                 575
Lys Ala Ala Leu Ala Asp Ser Leu Gln Arg Thr Ala Arg Asp Ala Glu
            580                 585                 590
Leu Gln Ser Tyr Glu Val Pro Ala Asp Phe Ile Val Glu Thr Glu Pro
            595                 600                 605
Phe Ser Ala Ala Asn Gly Leu Leu Ser Gly Val Gly Lys Leu Leu Arg
610                 615                 620
Pro Asn Leu Lys Asp Arg Tyr Gly Gln Arg Leu Glu Gln Met Tyr Ala
625                 630                 635                 640
Asp Ile Ala Ala Thr Gln Ala Asn Gln Leu Arg Glu Leu Arg Arg Ala
            645                 650                 655
Ala Ala Thr Gln Pro Val Ile Asp Thr Leu Thr Gln Ala Ala Ala Thr
            660                 665                 670
Ile Leu Gly Thr Gly Ser Glu Val Ala Ser Asp Ala His Phe Thr Asp
            675                 680                 685
Leu Gly Gly Asp Ser Leu Ser Ala Leu Thr Leu Ser Asn Leu Leu Ser
            690                 695                 700
Asp Phe Phe Gly Phe Glu Val Pro Val Gly Thr Ile Val Asn Pro Ala
705                 710                 715                 720
Thr Asn Leu Ala Gln Leu Ala Gln His Ile Glu Ala Gln Arg Thr Ala
            725                 730                 735
Gly Asp Arg Arg Pro Ser Phe Thr Thr Val His Gly Ala Asp Ala Thr
            740                 745                 750
Glu Ile Arg Ala Ser Glu Leu Thr Leu Asp Lys Phe Ile Asp Ala Glu
            755                 760                 765
Thr Leu Arg Ala Ala Pro Gly Leu Pro Lys Val Thr Thr Glu Pro Arg
            770                 775                 780
Thr Val Leu Leu Ser Gly Ala Asn Gly Trp Leu Gly Arg Phe Leu Thr
785                 790                 795                 800
Leu Gln Trp Leu Glu Arg Leu Ala Pro Val Gly Gly Thr Leu Ile Thr
            805                 810                 815
Ile Val Arg Gly Arg Asp Asp Ala Ala Ala Arg Ala Arg Leu Thr Gln
            820                 825                 830
Ala Tyr Asp Thr Asp Pro Glu Leu Ser Arg Arg Phe Ala Glu Leu Ala
            835                 840                 845
```

-continued

```
Asp Arg His Leu Arg Val Val Ala Gly Asp Ile Gly Asp Pro Asn Leu
850                 855                 860

Gly Leu Thr Pro Glu Ile Trp His Arg Leu Ala Ala Glu Val Asp Leu
865                 870                 875                 880

Val Val His Pro Ala Ala Leu Val Asn His Val Leu Pro Tyr Arg Gln
                885                 890                 895

Leu Phe Gly Pro Asn Val Val Gly Thr Ala Glu Val Ile Lys Leu Ala
                900                 905                 910

Leu Thr Glu Arg Ile Lys Pro Val Thr Tyr Leu Ser Thr Val Ser Val
            915                 920                 925

Ala Met Gly Ile Pro Asp Phe Glu Glu Asp Gly Asp Ile Arg Thr Val
930                 935                 940

Ser Pro Val Arg Pro Leu Asp Gly Gly Tyr Ala Asn Gly Tyr Gly Asn
945                 950                 955                 960

Ser Lys Trp Ala Gly Glu Val Leu Leu Arg Glu Ala His Asp Leu Cys
                965                 970                 975

Gly Leu Pro Val Ala Thr Phe Arg Ser Asp Met Ile Leu Ala His Pro
                980                 985                 990

Arg Tyr Arg Gly Gln Val Asn Val Pro Asp Met Phe Thr Arg Leu Leu
            995                 1000                1005

Leu Ser Leu Leu Ile Thr Gly Val Ala Pro Arg Ser Phe Tyr Ile
    1010                1015                1020

Gly Asp Gly Glu Arg Pro Arg Ala His Tyr Pro Gly Leu Thr Val
    1025                1030                1035

Asp Phe Val Ala Glu Ala Val Thr Thr Leu Gly Ala Gln Gln Arg
    1040                1045                1050

Glu Gly Tyr Val Ser Tyr Asp Val Met Asn Pro His Asp Asp Gly
    1055                1060                1065

Ile Ser Leu Asp Val Phe Val Asp Trp Leu Ile Arg Ala Gly His
    1070                1075                1080

Pro Ile Asp Arg Val Asp Asp Tyr Asp Asp Trp Val Arg Arg Phe
    1085                1090                1095

Glu Thr Ala Leu Thr Ala Leu Pro Glu Lys Arg Arg Ala Gln Thr
    1100                1105                1110

Val Leu Pro Leu Leu His Ala Phe Arg Ala Pro Gln Ala Pro Leu
    1115                1120                1125

Arg Gly Ala Pro Glu Pro Thr Glu Val Phe His Ala Ala Val Arg
    1130                1135                1140

Thr Ala Lys Val Gly Pro Gly Asp Ile Pro His Leu Asp Glu Ala
    1145                1150                1155

Leu Ile Asp Lys Tyr Ile Arg Asp Leu Arg Glu Phe Gly Leu Ile
    1160                1165                1170
```

<210> SEQ ID NO 4
<211> LENGTH: 1148
<212> TYPE: PRT
<213> ORGANISM: Segniliparus rugosus

<400> SEQUENCE: 4

```
Met Gly Asp Gly Glu Glu Arg Ala Lys Arg Phe Phe Gln Arg Ile Gly
1               5                   10                  15

Glu Leu Ser Ala Thr Asp Pro Gln Phe Ala Ala Ala Pro Asp Pro
            20                  25                  30

Ala Val Val Glu Ala Val Ser Asp Pro Ser Leu Ser Phe Thr Arg Tyr
```

```
            35                  40                  45
Leu Asp Thr Leu Met Arg Gly Tyr Ala Glu Arg Pro Ala Leu Ala His
 50                  55                  60

Arg Val Gly Ala Gly Tyr Glu Thr Ile Ser Tyr Gly Glu Leu Trp Ala
 65                  70                  75                  80

Arg Val Gly Ala Ile Ala Ala Trp Gln Ala Asp Gly Leu Ala Pro
                 85                  90                  95

Gly Asp Phe Val Ala Thr Val Gly Phe Thr Ser Pro Asp Tyr Val Ala
                100                 105                 110

Val Asp Leu Ala Ala Ala Arg Ser Gly Leu Val Ser Val Pro Leu Gln
                115                 120                 125

Ala Gly Ala Ser Leu Ala Gln Leu Val Gly Ile Leu Glu Glu Thr Glu
                130                 135                 140

Pro Lys Val Leu Ala Ala Ser Ala Ser Ser Leu Glu Gly Ala Val Ala
145                 150                 155                 160

Cys Ala Leu Ala Ala Pro Ser Val Gln Arg Leu Val Val Phe Asp Leu
                165                 170                 175

Arg Gly Pro Asp Ala Ser Glu Ser Ala Ala Asp Glu Arg Arg Gly Ala
                180                 185                 190

Leu Ala Asp Ala Glu Glu Gln Leu Ala Arg Ala Gly Arg Ala Val Val
                195                 200                 205

Val Glu Thr Leu Ala Asp Leu Ala Ala Arg Gly Glu Ala Leu Pro Glu
210                 215                 220

Ala Pro Leu Phe Glu Pro Ala Glu Gly Glu Asp Pro Leu Ala Leu Leu
225                 230                 235                 240

Ile Tyr Thr Ser Gly Ser Thr Gly Ala Pro Lys Gly Ala Met Tyr Ser
                245                 250                 255

Gln Arg Leu Val Ser Gln Leu Trp Gly Arg Thr Pro Val Val Pro Gly
                260                 265                 270

Met Pro Asn Ile Ser Leu His Tyr Met Pro Leu Ser His Ser Tyr Gly
                275                 280                 285

Arg Ala Val Leu Ala Gly Ala Leu Ser Ala Gly Gly Thr Ala His Phe
                290                 295                 300

Thr Ala Asn Ser Asp Leu Ser Thr Leu Phe Glu Asp Ile Ala Leu Ala
305                 310                 315                 320

Arg Pro Thr Phe Leu Ala Leu Val Pro Arg Val Cys Glu Met Leu Phe
                325                 330                 335

Gln Glu Ser Gln Arg Gly Gln Asp Val Ala Glu Leu Arg Glu Arg Val
                340                 345                 350

Leu Gly Gly Arg Leu Leu Val Ala Val Cys Gly Ser Ala Pro Leu Ser
                355                 360                 365

Pro Glu Met Arg Ala Phe Met Glu Glu Val Leu Gly Phe Pro Leu Leu
                370                 375                 380

Asp Gly Tyr Gly Ser Thr Glu Ala Leu Gly Val Met Arg Asn Gly Ile
385                 390                 395                 400

Ile Gln Arg Pro Pro Val Ile Asp Tyr Lys Leu Val Asp Val Pro Glu
                405                 410                 415

Leu Gly Tyr Arg Thr Thr Asp Lys Pro Tyr Pro Arg Gly Glu Leu Cys
                420                 425                 430

Ile Arg Ser Thr Ser Leu Ile Ser Gly Tyr Tyr Lys Arg Pro Glu Ile
                435                 440                 445

Thr Ala Glu Val Phe Asp Ala Gln Gly Tyr Tyr Lys Thr Gly Asp Val
450                 455                 460
```

-continued

Met Ala Glu Ile Ala Pro Asp His Leu Val Tyr Val Asp Arg Ser Lys
465                 470                 475                 480

Asn Val Leu Lys Leu Ser Gln Gly Glu Phe Val Ala Val Ala Lys Leu
            485                 490                 495

Glu Ala Ala Tyr Gly Thr Ser Pro Tyr Val Lys Gln Ile Phe Val Tyr
        500                 505                 510

Gly Asn Ser Glu Arg Ser Phe Leu Leu Ala Val Val Pro Asn Ala
    515                 520                 525

Glu Val Leu Gly Ala Arg Asp Gln Glu Glu Ala Lys Pro Leu Ile Ala
530                 535                 540

Ala Ser Leu Gln Lys Ile Ala Lys Glu Ala Gly Leu Gln Ser Tyr Glu
545                 550                 555                 560

Val Pro Arg Asp Phe Leu Ile Glu Thr Glu Pro Phe Thr Thr Gln Asn
                565                 570                 575

Gly Leu Leu Ser Glu Val Gly Lys Leu Leu Arg Pro Lys Leu Lys Ala
            580                 585                 590

Arg Tyr Gly Glu Ala Leu Glu Ala Arg Tyr Asp Glu Ile Ala His Gly
        595                 600                 605

Gln Ala Asp Glu Leu Arg Ala Leu Arg Asp Gly Ala Gly Gln Arg Pro
610                 615                 620

Val Val Glu Thr Val Val Arg Ala Ala Val Ala Ile Ser Gly Ser Glu
625                 630                 635                 640

Gly Ala Glu Val Gly Pro Glu Ala Asn Phe Ala Asp Leu Gly Gly Asp
                645                 650                 655

Ser Leu Ser Ala Leu Ser Leu Ala Asn Leu Leu His Asp Val Phe Glu
            660                 665                 670

Val Glu Val Pro Val Arg Ile Ile Ile Gly Pro Thr Ala Ser Leu Ala
        675                 680                 685

Gly Ile Ala Lys His Ile Glu Ala Glu Arg Ala Gly Ala Ser Ala Pro
690                 695                 700

Thr Ala Ala Ser Val His Gly Ala Gly Ala Thr Arg Ile Arg Ala Ser
705                 710                 715                 720

Glu Leu Thr Leu Glu Lys Phe Leu Pro Glu Asp Leu Leu Ala Ala Ala
                725                 730                 735

Lys Gly Leu Pro Ala Ala Asp Gln Val Arg Thr Val Leu Leu Thr Gly
            740                 745                 750

Ala Asn Gly Trp Leu Gly Arg Phe Leu Ala Leu Glu Gln Leu Glu Arg
        755                 760                 765

Leu Ala Arg Ser Gly Gln Asp Gly Gly Lys Leu Ile Cys Leu Val Arg
    770                 775                 780

Gly Lys Asp Ala Ala Ala Arg Arg Ile Glu Glu Thr Leu Gly
785                 790                 795                 800

Thr Asp Pro Ala Leu Ala Ala Arg Phe Ala Glu Leu Ala Glu Gly Arg
                805                 810                 815

Leu Glu Val Val Pro Gly Asp Val Gly Glu Pro Lys Phe Gly Leu Asp
            820                 825                 830

Asp Ala Ala Trp Asp Arg Leu Ala Glu Glu Val Asp Val Ile Val His
        835                 840                 845

Pro Ala Ala Leu Val Asn His Val Leu Pro Tyr His Gln Leu Phe Gly
    850                 855                 860

Pro Asn Val Val Gly Thr Ala Glu Ile Ile Arg Leu Ala Ile Thr Ala
865                 870                 875                 880

-continued

Lys Arg Lys Pro Val Thr Tyr Leu Ser Thr Val Ala Val Ala Ala Gly
                885                 890                 895

Val Glu Pro Ser Ser Phe Glu Glu Asp Gly Asp Ile Arg Ala Val Val
            900                 905                 910

Pro Glu Arg Pro Leu Gly Asp Gly Tyr Ala Asn Gly Tyr Gly Asn Ser
        915                 920                 925

Lys Trp Ala Gly Glu Val Leu Leu Arg Glu Ala His Glu Leu Val Gly
    930                 935                 940

Leu Pro Val Ala Val Phe Arg Ser Asp Met Ile Leu Ala His Thr Arg
945                 950                 955                 960

Tyr Thr Gly Gln Leu Asn Val Pro Asp Gln Phe Thr Arg Leu Val Leu
                965                 970                 975

Ser Leu Leu Ala Thr Gly Ile Ala Pro Lys Ser Phe Tyr Gln Gln Gly
            980                 985                 990

Ala Ala Gly Glu Arg Gln Arg Ala His Tyr Asp Gly Ile Pro Val Asp
        995                 1000                1005

Phe Thr Ala Glu Ala Ile Thr Thr Leu Gly Ala Glu Pro Ser Trp
        1010                1015                1020

Phe Asp Gly Gly Ala Gly Phe Arg Ser Phe Asp Val Phe Asn Pro
        1025                1030                1035

His His Asp Gly Val Gly Leu Asp Glu Phe Val Asp Trp Leu Ile
        1040                1045                1050

Glu Ala Gly His Pro Ile Ser Arg Ile Asp Asp His Lys Glu Trp
        1055                1060                1065

Phe Ala Arg Phe Glu Thr Ala Val Arg Gly Leu Pro Glu Ala Gln
        1070                1075                1080

Arg Gln His Ser Leu Leu Pro Leu Leu Arg Ala Tyr Ser Phe Pro
        1085                1090                1095

His Pro Pro Val Asp Gly Ser Val Tyr Pro Thr Gly Lys Phe Gln
        1100                1105                1110

Gly Ala Val Lys Ala Ala Gln Val Gly Ser Asp His Asp Val Pro
        1115                1120                1125

His Leu Gly Lys Ala Leu Ile Val Lys Tyr Ala Asp Asp Leu Lys
        1130                1135                1140

Ala Leu Gly Leu Leu
        1145

<210> SEQ ID NO 5
<211> LENGTH: 1185
<212> TYPE: PRT
<213> ORGANISM: Mycobacterium abscessus

<400> SEQUENCE: 5

Met Thr Asn Glu Thr Asn Pro Gln Gln Glu Gln Leu Ser Arg Arg Ile
1               5                   10                  15

Glu Ser Leu Arg Glu Ser Asp Pro Gln Phe Arg Ala Ala Gln Pro Asp
            20                  25                  30

Pro Ala Val Ala Glu Gln Val Leu Arg Pro Gly Leu His Leu Ser Glu
        35                  40                  45

Ala Ile Ala Ala Leu Met Thr Gly Tyr Ala Glu Arg Pro Ala Leu Gly
    50                  55                  60

Glu Arg Ala Arg Glu Leu Val Ile Asp Gln Asp Gly Arg Thr Thr Leu
65                  70                  75                  80

Arg Leu Leu Pro Arg Phe Asp Thr Thr Thr Tyr Gly Glu Leu Trp Ser
                85                  90                  95

```
Arg Thr Thr Ser Val Ala Ala Ala Trp His His Asp Ala Thr His Pro
            100                 105                 110

Val Lys Ala Gly Asp Leu Val Ala Thr Leu Gly Phe Thr Ser Ile Asp
            115                 120                 125

Tyr Thr Val Leu Asp Leu Ala Ile Met Ile Leu Gly Gly Val Ala Val
    130                 135                 140

Pro Leu Gln Thr Ser Ala Pro Ala Ser Gln Trp Thr Thr Ile Leu Ala
145                 150                 155                 160

Glu Ala Glu Pro Asn Thr Leu Ala Val Ser Ile Glu Leu Ile Gly Ala
                165                 170                 175

Ala Met Glu Ser Val Arg Ala Thr Pro Ser Ile Lys Gln Val Val Val
            180                 185                 190

Phe Asp Tyr Thr Pro Glu Val Asp Asp Gln Arg Glu Ala Phe Glu Ala
            195                 200                 205

Ala Ser Thr Gln Leu Ala Gly Thr Gly Ile Ala Leu Glu Thr Leu Asp
    210                 215                 220

Ala Val Ile Ala Arg Gly Ala Ala Leu Pro Ala Ala Pro Leu Tyr Ala
225                 230                 235                 240

Pro Ser Ala Gly Asp Asp Pro Leu Ala Leu Leu Ile Tyr Thr Ser Gly
                245                 250                 255

Ser Thr Gly Ala Pro Lys Gly Ala Met His Ser Glu Asn Ile Val Arg
            260                 265                 270

Arg Trp Trp Ile Arg Glu Asp Val Met Ala Gly Thr Glu Asn Leu Pro
            275                 280                 285

Met Ile Gly Leu Asn Phe Met Pro Met Ser His Ile Met Gly Arg Gly
            290                 295                 300

Thr Leu Thr Ser Thr Leu Ser Thr Gly Gly Thr Gly Tyr Phe Ala Ala
305                 310                 315                 320

Ser Ser Asp Met Ser Thr Leu Phe Glu Asp Met Glu Leu Ile Arg Pro
                325                 330                 335

Thr Ala Leu Ala Leu Val Pro Arg Val Cys Asp Met Val Phe Gln Arg
            340                 345                 350

Phe Gln Thr Glu Val Asp Arg Arg Leu Ala Ser Gly Asp Thr Ala Ser
            355                 360                 365

Ala Glu Ala Val Ala Ala Glu Val Lys Ala Asp Ile Arg Asp Asn Leu
    370                 375                 380

Phe Gly Gly Arg Val Ser Ala Val Met Val Gly Ser Ala Pro Leu Ser
385                 390                 395                 400

Glu Glu Leu Gly Glu Phe Ile Glu Ser Cys Phe Glu Leu Asn Leu Thr
                405                 410                 415

Asp Gly Tyr Gly Ser Thr Glu Ala Gly Met Val Phe Arg Asp Gly Ile
            420                 425                 430

Val Gln Arg Pro Pro Val Ile Asp Tyr Lys Leu Val Asp Val Pro Glu
            435                 440                 445

Leu Gly Tyr Phe Ser Thr Asp Lys Pro His Pro Arg Gly Glu Leu Leu
    450                 455                 460

Leu Lys Thr Asp Gly Met Phe Leu Gly Tyr Tyr Lys Arg Pro Glu Val
465                 470                 475                 480

Thr Ala Ser Val Phe Asp Ala Asp Gly Phe Tyr Met Thr Gly Asp Ile
                485                 490                 495

Val Ala Glu Leu Ala His Asp Asn Ile Glu Ile Ile Asp Arg Arg Asn
            500                 505                 510
```

```
Asn Val Leu Lys Leu Ser Gln Gly Glu Phe Val Ala Val Ala Thr Leu
            515                 520                 525

Glu Ala Glu Tyr Ala Asn Ser Pro Val His Gln Ile Tyr Val Tyr
530                 535                 540

Gly Ser Ser Glu Arg Ser Tyr Leu Leu Ala Val Val Pro Thr Pro
545                 550                 555                 560

Glu Ala Val Ala Ala Lys Gly Asp Ala Ala Leu Lys Thr Thr
                565                 570                 575

Ile Ala Asp Ser Leu Gln Asp Ile Ala Lys Glu Ile Gln Leu Gln Ser
            580                 585                 590

Tyr Glu Val Pro Arg Asp Phe Ile Ile Glu Pro Gln Pro Phe Thr Gln
595                 600                 605

Gly Asn Gly Leu Leu Thr Gly Ile Ala Lys Leu Ala Arg Pro Asn Leu
610                 615                 620

Lys Ala His Tyr Gly Pro Arg Leu Glu Gln Met Tyr Ala Glu Ile Ala
625                 630                 635                 640

Glu Gln Gln Ala Ala Glu Leu Arg Ala Leu His Gly Val Asp Pro Asp
                645                 650                 655

Lys Pro Ala Leu Glu Thr Val Leu Lys Ala Ala Gln Ala Leu Leu Gly
            660                 665                 670

Val Ser Ser Ala Glu Leu Ala Ala Asp Ala His Phe Thr Asp Leu Gly
675                 680                 685

Gly Asp Ser Leu Ser Ala Leu Ser Phe Ser Asp Leu Leu Arg Asp Ile
690                 695                 700

Phe Ala Val Glu Val Pro Val Gly Val Ile Val Ser Ala Ala Asn Asp
705                 710                 715                 720

Leu Gly Gly Val Ala Lys Phe Val Asp Glu Gln Arg His Ser Gly Gly
                725                 730                 735

Thr Arg Pro Thr Ala Glu Thr Val His Gly Ala Gly His Thr Glu Ile
            740                 745                 750

Arg Ala Ala Asp Leu Thr Leu Asp Lys Phe Ile Asp Glu Ala Thr Leu
755                 760                 765

His Ala Ala Pro Ser Leu Pro Lys Ala Ala Gly Ile Pro His Thr Val
770                 775                 780

Leu Leu Thr Gly Ser Asn Gly Tyr Leu Gly His Tyr Leu Ala Leu Glu
785                 790                 795                 800

Trp Leu Glu Arg Leu Asp Lys Thr Asp Gly Lys Leu Ile Val Ile Val
                805                 810                 815

Arg Gly Lys Asn Ala Glu Ala Ala Tyr Gly Arg Leu Glu Glu Ala Phe
            820                 825                 830

Asp Thr Gly Asp Thr Glu Leu Leu Ala His Phe Arg Ser Leu Ala Asp
835                 840                 845

Lys His Leu Glu Val Leu Ala Gly Asp Ile Gly Asp Pro Asn Leu Gly
850                 855                 860

Leu Asp Ala Asp Thr Trp Gln Arg Leu Ala Asp Thr Val Asp Val Ile
865                 870                 875                 880

Val His Pro Ala Ala Leu Val Asn His Val Leu Pro Tyr Asn Gln Leu
                885                 890                 895

Phe Gly Pro Asn Val Val Gly Thr Ala Glu Ile Ile Lys Leu Ala Ile
            900                 905                 910

Thr Thr Lys Ile Lys Pro Val Thr Tyr Leu Ser Thr Val Ala Val Ala
915                 920                 925

Ala Tyr Val Asp Pro Thr Thr Phe Asp Glu Glu Ser Asp Ile Arg Leu
```

```
                930             935                 940
Ile Ser Ala Val Arg Pro Ile Asp Asp Gly Tyr Ala Asn Gly Tyr Gly
945                 950                 955                 960

Asn Ala Lys Trp Ala Gly Glu Val Leu Leu Arg Glu Ala His Asp Leu
                965                 970                 975

Cys Gly Leu Pro Val Ala Val Phe Arg Ser Asp Met Ile Leu Ala His
                980                 985                 990

Ser Arg Tyr Thr Gly Gln Leu Asn Val Pro Asp Gln Phe Thr Arg Leu
                995                1000                1005

Ile Leu Ser Leu Ile Ala Thr Gly Ile Ala Pro Gly Ser Phe Tyr
     1010                1015                1020

Gln Ala Gln Thr Thr Gly Glu Arg Pro Leu Ala His Tyr Asp Gly
     1025                1030                1035

Leu Pro Gly Asp Phe Thr Ala Glu Ala Ile Thr Thr Leu Gly Thr
     1040                1045                1050

Gln Val Pro Glu Gly Ser Gly Phe Val Thr Tyr Asp Cys Val
     1055                1060                1065

Asn Pro His Ala Asp Gly Ile Ser Leu Asp Asn Phe Val Asp Trp
     1070                1075                1080

Leu Ile Glu Ala Gly Tyr Pro Ile Ala Arg Ile Asp Asn Tyr Thr
     1085                1090                1095

Glu Trp Phe Thr Arg Phe Asp Thr Ala Ile Arg Gly Leu Ser Glu
     1100                1105                1110

Lys Gln Lys Gln His Ser Leu Leu Pro Leu Leu His Ala Phe Glu
     1115                1120                1125

Gln Pro Ser Ala Ala Glu Asn His Gly Val Val Pro Ala Lys Arg
     1130                1135                1140

Phe Gln His Ala Val Gln Ala Ala Gly Ile Gly Pro Val Gly Gln
     1145                1150                1155

Asp Gly Thr Thr Asp Ile Pro His Leu Ser Arg Arg Leu Ile Val
     1160                1165                1170

Lys Tyr Ala Lys Asp Leu Glu Gln Leu Gly Leu Leu
     1175                1180                1185

<210> SEQ ID NO 6
<211> LENGTH: 1186
<212> TYPE: PRT
<213> ORGANISM: Segniliparus rotundus

<400> SEQUENCE: 6

Met Thr Gln Ser His Thr Gln Gly Pro Gln Ala Ser Ala His Ser
1               5                  10                  15

Arg Leu Ala Arg Arg Ala Ala Glu Leu Leu Ala Thr Asp Pro Gln Ala
                20                  25                  30

Ala Ala Thr Leu Pro Asp Pro Glu Val Val Arg Gln Ala Thr Arg Pro
        35                  40                  45

Gly Leu Arg Leu Ala Glu Arg Val Asp Ala Ile Leu Ser Gly Tyr Ala
    50                  55                  60

Asp Arg Pro Ala Leu Gly Gln Arg Ser Phe Gln Thr Val Lys Asp Pro
65                  70                  75                  80

Ile Thr Gly Arg Ser Ser Val Glu Leu Leu Pro Thr Phe Asp Thr Ile
                85                  90                  95

Thr Tyr Arg Glu Leu Arg Glu Arg Ala Thr Ala Ile Ala Ser Asp Leu
            100                 105                 110
```

-continued

```
Ala His His Pro Gln Ala Pro Ala Lys Pro Gly Asp Phe Leu Ala Ser
            115                 120                 125

Ile Gly Phe Ile Ser Val Asp Tyr Val Ala Ile Asp Ile Ala Gly Val
        130                 135                 140

Phe Ala Gly Leu Thr Ala Val Pro Leu Gln Thr Gly Ala Thr Leu Ala
145                 150                 155                 160

Thr Leu Thr Ala Ile Thr Ala Glu Thr Ala Pro Thr Leu Phe Ala Ala
                165                 170                 175

Ser Ile Glu His Leu Pro Thr Ala Val Asp Ala Val Leu Ala Thr Pro
            180                 185                 190

Ser Val Arg Arg Leu Leu Val Phe Asp Tyr Arg Ala Gly Ser Asp Glu
        195                 200                 205

Asp Arg Glu Ala Val Glu Ala Ala Lys Arg Lys Ile Ala Asp Ala Gly
210                 215                 220

Ser Ser Val Leu Val Asp Val Leu Asp Glu Val Ile Ala Arg Gly Lys
225                 230                 235                 240

Ser Ala Pro Lys Ala Pro Leu Pro Pro Ala Thr Asp Ala Gly Asp Asp
                245                 250                 255

Ser Leu Ser Leu Leu Ile Tyr Thr Ser Gly Ser Thr Gly Thr Pro Lys
            260                 265                 270

Gly Ala Met Tyr Pro Glu Arg Asn Val Ala His Phe Trp Gly Gly Val
        275                 280                 285

Trp Ala Ala Phe Asp Glu Asp Ala Ala Pro Val Pro Ala Ile
290                 295                 300

Asn Ile Thr Phe Leu Pro Leu Ser His Val Ala Ser Arg Leu Ser Leu
305                 310                 315                 320

Met Pro Thr Leu Ala Arg Gly Gly Leu Met His Phe Val Ala Lys Ser
                325                 330                 335

Asp Leu Ser Thr Leu Phe Glu Asp Leu Lys Leu Ala Arg Pro Thr Asn
            340                 345                 350

Leu Phe Leu Val Pro Arg Val Val Glu Met Leu Tyr Gln His Tyr Gln
        355                 360                 365

Ser Glu Leu Asp Arg Arg Gly Val Gln Asp Gly Thr Arg Glu Ala Glu
370                 375                 380

Ala Val Lys Asp Asp Leu Arg Thr Gly Leu Leu Gly Gly Arg Ile Leu
385                 390                 395                 400

Thr Ala Gly Phe Gly Ser Ala Pro Leu Ser Ala Glu Leu Ala Gly Phe
                405                 410                 415

Ile Glu Ser Leu Leu Gln Ile His Leu Val Asp Gly Tyr Gly Ser Thr
            420                 425                 430

Glu Ala Gly Pro Val Trp Arg Asp Gly Tyr Leu Val Lys Pro Pro Val
        435                 440                 445

Thr Asp Tyr Lys Leu Ile Asp Val Pro Glu Leu Gly Tyr Phe Ser Thr
450                 455                 460

Asp Ser Pro His Pro Arg Gly Glu Leu Ala Ile Lys Thr Gln Thr Ile
465                 470                 475                 480

Leu Pro Gly Tyr Tyr Lys Arg Pro Glu Thr Thr Ala Glu Val Phe Asp
                485                 490                 495

Glu Asp Gly Phe Tyr Leu Thr Gly Asp Val Val Ala Gln Ile Gly Pro
            500                 505                 510

Glu Gln Phe Ala Tyr Val Asp Arg Arg Lys Asn Val Leu Lys Leu Ser
        515                 520                 525

Gln Gly Glu Phe Val Thr Leu Ala Lys Leu Glu Ala Ala Tyr Ser Ser
```

```
               530                 535                 540
Ser Pro Leu Val Arg Gln Leu Phe Val Tyr Gly Ser Ser Glu Arg Ser
545                 550                 555                 560

Tyr Leu Leu Ala Val Ile Val Pro Thr Pro Asp Ala Leu Lys Lys Phe
                565                 570                 575

Gly Val Gly Glu Ala Ala Lys Ala Ala Leu Gly Glu Ser Leu Gln Lys
            580                 585                 590

Ile Ala Arg Asp Glu Gly Leu Gln Ser Tyr Glu Val Pro Arg Asp Phe
        595                 600                 605

Ile Ile Glu Thr Asp Pro Phe Thr Val Glu Asn Gly Leu Leu Ser Asp
    610                 615                 620

Ala Arg Lys Ser Leu Arg Pro Lys Leu Lys Glu His Tyr Gly Glu Arg
625                 630                 635                 640

Leu Glu Ala Met Tyr Lys Glu Leu Ala Asp Gly Gln Ala Asn Glu Leu
                645                 650                 655

Arg Asp Ile Arg Arg Gly Val Gln Gln Arg Pro Thr Leu Glu Thr Val
            660                 665                 670

Arg Arg Ala Ala Ala Ala Met Leu Gly Ala Ser Ala Ala Glu Ile Lys
        675                 680                 685

Pro Asp Ala His Phe Thr Asp Leu Gly Gly Asp Ser Leu Ser Ala Leu
    690                 695                 700

Thr Phe Ser Asn Phe Leu His Asp Leu Phe Glu Val Asp Val Pro Val
705                 710                 715                 720

Gly Val Ile Val Ser Ala Ala Asn Thr Leu Gly Ser Val Ala Glu His
                725                 730                 735

Ile Asp Ala Gln Leu Ala Gly Gly Arg Ala Arg Pro Thr Phe Ala Thr
            740                 745                 750

Val His Gly Lys Gly Ser Thr Thr Ile Lys Ala Ser Asp Leu Thr Leu
        755                 760                 765

Asp Lys Phe Ile Asp Glu Gln Thr Leu Glu Ala Ala Lys His Leu Pro
    770                 775                 780

Lys Pro Ala Asp Pro Pro Arg Thr Val Leu Leu Thr Gly Ala Asn Gly
785                 790                 795                 800

Trp Leu Gly Arg Phe Leu Ala Leu Glu Trp Leu Glu Arg Leu Ala Pro
                805                 810                 815

Ala Gly Gly Lys Leu Ile Thr Ile Val Arg Gly Lys Asp Ala Ala Gln
            820                 825                 830

Ala Lys Ala Arg Leu Asp Ala Ala Tyr Glu Ser Gly Asp Pro Lys Leu
        835                 840                 845

Ala Gly His Tyr Gln Asp Leu Ala Ala Thr Thr Leu Glu Val Leu Ala
    850                 855                 860

Gly Asp Phe Ser Glu Pro Arg Leu Gly Leu Asp Glu Ala Thr Trp Asn
865                 870                 875                 880

Arg Leu Ala Asp Glu Val Asp Phe Ile Ser His Pro Gly Ala Leu Val
                885                 890                 895

Asn His Val Leu Pro Tyr Asn Gln Leu Phe Gly Pro Asn Val Ala Gly
            900                 905                 910

Val Ala Glu Ile Ile Lys Leu Ala Ile Thr Thr Arg Ile Lys Pro Val
        915                 920                 925

Thr Tyr Leu Ser Thr Val Ala Val Ala Ala Gly Val Glu Pro Ser Ala
    930                 935                 940

Leu Asp Glu Asp Gly Asp Ile Arg Thr Val Ser Ala Glu Arg Ser Val
945                 950                 955                 960
```

Asp Glu Gly Tyr Ala Asn Gly Tyr Gly Asn Ser Lys Trp Gly Gly Glu
            965                 970                 975

Val Leu Leu Arg Glu Ala His Asp Arg Thr Gly Leu Pro Val Arg Val
            980                 985                 990

Phe Arg Ser Asp Met Ile Leu Ala His Gln Lys Tyr Thr Gly Gln Val
            995                 1000                1005

Asn Ala Thr Asp Gln Phe Thr Arg Leu Val Gln Ser Leu Leu Ala
        1010                1015                1020

Thr Gly Leu Ala Pro Lys Ser Phe Tyr Glu Leu Asp Ala Gln Gly
        1025                1030                1035

Asn Arg Gln Arg Ala His Tyr Asp Gly Ile Pro Val Asp Phe Thr
        1040                1045                1050

Ala Glu Ser Ile Thr Thr Leu Gly Gly Asp Gly Leu Glu Gly Tyr
        1055                1060                1065

Arg Ser Tyr Asn Val Phe Asn Pro His Arg Asp Gly Val Gly Leu
        1070                1075                1080

Asp Glu Phe Val Asp Trp Leu Ile Glu Ala Gly His Pro Ile Thr
        1085                1090                1095

Arg Ile Asp Asp Tyr Asp Gln Trp Leu Ser Arg Phe Glu Thr Ser
        1100                1105                1110

Leu Arg Gly Leu Pro Glu Ser Lys Arg Gln Ala Ser Val Leu Pro
        1115                1120                1125

Leu Leu His Ala Phe Ala Arg Pro Gly Pro Ala Val Asp Gly Ser
        1130                1135                1140

Pro Phe Arg Asn Thr Val Phe Arg Thr Asp Val Gln Lys Ala Lys
        1145                1150                1155

Ile Gly Ala Glu His Asp Ile Pro His Leu Gly Lys Ala Leu Val
        1160                1165                1170

Leu Lys Tyr Ala Asp Asp Ile Lys Gln Leu Gly Leu Leu
        1175                1180                1185

<210> SEQ ID NO 7
<211> LENGTH: 459
<212> TYPE: PRT
<213> ORGANISM: Chromobacterium violaceum

<400> SEQUENCE: 7

Met Gln Lys Gln Arg Thr Thr Ser Gln Trp Arg Glu Leu Asp Ala Ala
1               5                   10                  15

His His Leu His Pro Phe Thr Asp Thr Ala Ser Leu Asn Gln Ala Gly
                20                  25                  30

Ala Arg Val Met Thr Arg Gly Glu Gly Val Tyr Leu Trp Asp Ser Glu
            35                  40                  45

Gly Asn Lys Ile Ile Asp Gly Met Ala Gly Leu Trp Cys Val Asn Val
        50                  55                  60

Gly Tyr Gly Arg Lys Asp Phe Ala Glu Ala Ala Arg Arg Gln Met Glu
65                  70                  75                  80

Glu Leu Pro Phe Tyr Asn Thr Phe Phe Lys Thr Thr His Pro Ala Val
                85                  90                  95

Val Glu Leu Ser Ser Leu Leu Ala Glu Val Thr Pro Ala Gly Phe Asp
            100                 105                 110

Arg Val Phe Tyr Thr Asn Ser Gly Ser Glu Ser Val Asp Thr Met Ile
        115                 120                 125

Arg Met Val Arg Arg Tyr Trp Asp Val Gln Gly Lys Pro Glu Lys Lys

```
                    130                 135                 140
Thr Leu Ile Gly Arg Trp Asn Gly Tyr His Gly Ser Thr Ile Gly Gly
145                 150                 155                 160

Ala Ser Leu Gly Gly Met Lys Tyr Met His Glu Gln Gly Asp Leu Pro
                165                 170                 175

Ile Pro Gly Met Ala His Ile Glu Gln Pro Trp Trp Tyr Lys His Gly
            180                 185                 190

Lys Asp Met Thr Pro Asp Glu Phe Gly Val Val Ala Ala Arg Trp Leu
        195                 200                 205

Glu Glu Lys Ile Leu Glu Ile Gly Ala Asp Lys Val Ala Ala Phe Val
    210                 215                 220

Gly Glu Pro Ile Gln Gly Ala Gly Gly Val Ile Val Pro Pro Ala Thr
225                 230                 235                 240

Tyr Trp Pro Glu Ile Glu Arg Ile Cys Arg Lys Tyr Asp Val Leu Leu
                245                 250                 255

Val Ala Asp Glu Val Ile Cys Gly Phe Gly Arg Thr Gly Glu Trp Phe
            260                 265                 270

Gly His Gln His Phe Gly Phe Gln Pro Asp Leu Phe Thr Ala Ala Lys
        275                 280                 285

Gly Leu Ser Ser Gly Tyr Leu Pro Ile Gly Ala Val Phe Val Gly Lys
    290                 295                 300

Arg Val Ala Glu Gly Leu Ile Ala Gly Gly Asp Phe Asn His Gly Phe
305                 310                 315                 320

Thr Tyr Ser Gly His Pro Val Cys Ala Ala Val Ala His Ala Asn Val
                325                 330                 335

Ala Ala Leu Arg Asp Glu Gly Ile Val Gln Arg Val Lys Asp Asp Ile
            340                 345                 350

Gly Pro Tyr Met Gln Lys Arg Trp Arg Glu Thr Phe Ser Arg Phe Glu
        355                 360                 365

His Val Asp Asp Val Arg Gly Val Gly Met Val Gln Ala Phe Thr Leu
    370                 375                 380

Val Lys Asn Lys Ala Lys Arg Glu Leu Phe Pro Asp Phe Gly Glu Ile
385                 390                 395                 400

Gly Thr Leu Cys Arg Asp Ile Phe Phe Arg Asn Asn Leu Ile Met Arg
                405                 410                 415

Ala Cys Gly Asp His Ile Val Ser Ala Pro Pro Leu Val Met Thr Arg
            420                 425                 430

Ala Glu Val Asp Glu Met Leu Ala Val Ala Glu Arg Cys Leu Glu Glu
        435                 440                 445

Phe Glu Gln Thr Leu Lys Ala Arg Gly Leu Ala
    450                 455

<210> SEQ ID NO 8
<211> LENGTH: 468
<212> TYPE: PRT
<213> ORGANISM: Pseudomonas aeruginosa

<400> SEQUENCE: 8

Met Asn Ala Arg Leu His Ala Thr Ser Pro Leu Gly Asp Ala Asp Leu
1               5                   10                  15

Val Arg Ala Asp Gln Ala His Tyr Met His Gly Tyr His Val Phe Asp
            20                  25                  30

Asp His Arg Val Asn Gly Ser Leu Asn Ile Ala Ala Gly Asp Gly Ala
        35                  40                  45
```

-continued

```
Tyr Ile Tyr Asp Thr Ala Gly Asn Arg Tyr Leu Asp Ala Val Gly Gly
     50                  55                  60

Met Trp Cys Thr Asn Ile Gly Leu Gly Arg Glu Glu Met Ala Arg Thr
 65                  70                  75                  80

Val Ala Glu Gln Thr Arg Leu Leu Ala Tyr Ser Asn Pro Phe Cys Asp
                 85                  90                  95

Met Ala Asn Pro Arg Ala Ile Glu Leu Cys Arg Lys Leu Ala Glu Leu
                100                 105                 110

Ala Pro Gly Asp Leu Asp His Val Phe Leu Thr Thr Gly Gly Ser Thr
                115                 120                 125

Ala Val Asp Thr Ala Ile Arg Leu Met His Tyr Tyr Gln Asn Cys Arg
    130                 135                 140

Gly Lys Arg Ala Lys Lys His Val Ile Thr Arg Ile Asn Ala Tyr His
145                 150                 155                 160

Gly Ser Thr Phe Leu Gly Met Ser Leu Gly Gly Lys Ser Ala Asp Arg
                165                 170                 175

Pro Ala Glu Phe Asp Phe Leu Asp Glu Arg Ile His His Leu Ala Cys
                180                 185                 190

Pro Tyr Tyr Tyr Arg Ala Pro Glu Gly Leu Gly Glu Ala Glu Phe Leu
                195                 200                 205

Asp Gly Leu Val Asp Glu Phe Glu Arg Lys Ile Leu Glu Leu Gly Ala
    210                 215                 220

Asp Arg Val Gly Ala Phe Ile Ser Glu Pro Val Phe Gly Ser Gly Gly
225                 230                 235                 240

Val Ile Val Pro Pro Ala Gly Tyr His Arg Arg Met Trp Glu Leu Cys
                245                 250                 255

Gln Arg Tyr Asp Val Leu Tyr Ile Ser Asp Glu Val Val Thr Ser Phe
                260                 265                 270

Gly Arg Leu Gly His Phe Phe Ala Ser Gln Ala Val Phe Gly Val Gln
                275                 280                 285

Pro Asp Ile Ile Leu Thr Ala Lys Gly Leu Thr Ser Gly Tyr Gln Pro
    290                 295                 300

Leu Gly Ala Cys Ile Phe Ser Arg Arg Ile Trp Glu Val Ile Ala Glu
305                 310                 315                 320

Pro Asp Lys Gly Arg Cys Phe Ser His Gly Phe Thr Tyr Ser Gly His
                325                 330                 335

Pro Val Ala Cys Ala Ala Ala Leu Lys Asn Ile Glu Ile Ile Glu Arg
                340                 345                 350

Glu Gly Leu Leu Ala His Ala Asp Glu Val Gly Arg Tyr Phe Glu Glu
                355                 360                 365

Arg Leu Gln Ser Leu Arg Asp Leu Pro Ile Val Gly Asp Val Arg Gly
    370                 375                 380

Met Arg Phe Met Ala Cys Val Glu Phe Val Ala Asp Lys Ala Ser Lys
385                 390                 395                 400

Ala Leu Phe Pro Glu Ser Leu Asn Ile Gly Glu Trp Val His Leu Arg
                405                 410                 415

Ala Gln Lys Arg Gly Leu Leu Val Arg Pro Ile Val His Leu Asn Val
                420                 425                 430

Met Ser Pro Pro Leu Ile Leu Thr Arg Glu Gln Val Asp Thr Val Val
                435                 440                 445

Arg Val Leu Arg Glu Ser Ile Glu Glu Thr Val Glu Asp Leu Val Arg
    450                 455                 460

Ala Gly His Arg
```

<210> SEQ ID NO 9
<211> LENGTH: 454
<212> TYPE: PRT
<213> ORGANISM: Pseudomonas syringae

<400> SEQUENCE: 9

```
Met Ser Ala Asn Asn Pro Gln Thr Leu Glu Trp Gln Ala Leu Ser Ser
1               5                   10                  15

Glu His His Leu Ala Pro Phe Ser Asp Tyr Lys Gln Leu Lys Glu Lys
            20                  25                  30

Gly Pro Arg Ile Ile Thr Arg Ala Glu Gly Val Tyr Leu Trp Asp Ser
        35                  40                  45

Glu Gly Asn Lys Ile Leu Asp Gly Met Ser Gly Leu Trp Cys Val Ala
    50                  55                  60

Ile Gly Tyr Gly Arg Glu Glu Leu Ala Asp Ala Ala Ser Lys Gln Met
65                  70                  75                  80

Arg Glu Leu Pro Tyr Tyr Asn Leu Phe Phe Gln Thr Ala His Pro Pro
                85                  90                  95

Val Leu Glu Leu Ala Lys Ala Ile Ser Asp Ile Ala Pro Glu Gly Met
            100                 105                 110

Asn His Val Phe Phe Thr Gly Ser Gly Ser Glu Gly Asn Asp Thr Met
        115                 120                 125

Leu Arg Met Val Arg His Tyr Trp Ala Leu Lys Gly Gln Pro Asn Lys
    130                 135                 140

Lys Thr Ile Ile Ser Arg Val Asn Gly Tyr His Gly Ser Thr Val Ala
145                 150                 155                 160

Gly Ala Ser Leu Gly Gly Met Thr Tyr Met His Glu Gln Gly Asp Leu
                165                 170                 175

Pro Ile Pro Gly Val Val His Ile Pro Gln Pro Tyr Trp Phe Gly Glu
            180                 185                 190

Gly Gly Asp Met Thr Pro Asp Glu Phe Gly Ile Trp Ala Ala Glu Gln
        195                 200                 205

Leu Glu Lys Lys Ile Leu Glu Leu Gly Val Glu Asn Val Gly Ala Phe
    210                 215                 220

Ile Ala Glu Pro Ile Gln Gly Ala Gly Gly Val Ile Val Pro Pro Asp
225                 230                 235                 240

Ser Tyr Trp Pro Lys Ile Lys Glu Ile Leu Ser Arg Tyr Asp Ile Leu
                245                 250                 255

Phe Ala Ala Asp Glu Val Ile Cys Gly Phe Gly Arg Thr Ser Glu Trp
            260                 265                 270

Phe Gly Ser Asp Phe Tyr Gly Leu Arg Pro Asp Met Met Thr Ile Ala
        275                 280                 285

Lys Gly Leu Thr Ser Gly Tyr Val Pro Met Gly Gly Leu Ile Val Arg
    290                 295                 300

Asp Glu Ile Val Ala Val Leu Asn Glu Gly Gly Asp Phe Asn His Gly
305                 310                 315                 320

Phe Thr Tyr Ser Gly His Pro Val Ala Ala Val Ala Leu Glu Asn
                325                 330                 335

Ile Arg Ile Leu Arg Glu Glu Lys Ile Val Glu Arg Val Arg Ser Glu
            340                 345                 350

Thr Ala Pro Tyr Leu Gln Lys Arg Leu Arg Glu Leu Ser Asp His Pro
        355                 360                 365
```

```
Leu Val Gly Glu Val Arg Gly Val Gly Leu Leu Ala Ile Glu Leu
    370                 375                 380

Val Lys Asp Lys Thr Thr Arg Glu Arg Tyr Thr Asp Lys Gly Ala Gly
385                 390                 395                 400

Met Ile Cys Arg Thr Phe Cys Phe Asp Asn Gly Leu Ile Met Arg Ala
                405                 410                 415

Val Gly Asp Thr Met Ile Ile Ala Pro Pro Leu Val Ile Ser Phe Ala
                420                 425                 430

Gln Ile Asp Glu Leu Val Glu Lys Ala Arg Thr Cys Leu Asp Leu Thr
                435                 440                 445

Leu Ala Val Leu Gln Gly
    450
```

<210> SEQ ID NO 10
<211> LENGTH: 467
<212> TYPE: PRT
<213> ORGANISM: Rhodobacter sphaeroides

<400> SEQUENCE: 10

```
Met Thr Arg Asn Asp Ala Thr Asn Ala Ala Gly Ala Val Gly Ala Ala
1               5                   10                  15

Met Arg Asp His Ile Leu Leu Pro Ala Gln Glu Met Ala Lys Leu Gly
                20                  25                  30

Lys Ser Ala Gln Pro Val Leu Thr His Ala Glu Gly Ile Tyr Val His
            35                  40                  45

Thr Glu Asp Gly Arg Arg Leu Ile Asp Gly Pro Ala Gly Met Trp Cys
        50                  55                  60

Ala Gln Val Gly Tyr Gly Arg Arg Glu Ile Val Asp Ala Met Ala His
65              70                  75                  80

Gln Ala Met Val Leu Pro Tyr Ala Ser Pro Trp Tyr Met Ala Thr Ser
                85                  90                  95

Pro Ala Ala Arg Leu Ala Glu Lys Ile Ala Thr Leu Thr Pro Gly Asp
            100                 105                 110

Leu Asn Arg Ile Phe Phe Thr Thr Gly Gly Ser Thr Ala Val Asp Ser
        115                 120                 125

Ala Leu Arg Phe Ser Glu Phe Tyr Asn Asn Val Leu Gly Arg Pro Gln
    130                 135                 140

Lys Lys Arg Ile Ile Val Arg Tyr Asp Gly Tyr His Gly Ser Thr Ala
145                 150                 155                 160

Leu Thr Ala Ala Cys Thr Gly Arg Thr Gly Asn Trp Pro Asn Phe Asp
                165                 170                 175

Ile Ala Gln Asp Arg Ile Ser Phe Leu Ser Ser Pro Asn Pro Arg His
                180                 185                 190

Ala Gly Asn Arg Ser Gln Glu Ala Phe Leu Asp Asp Leu Val Gln Glu
            195                 200                 205

Phe Glu Asp Arg Ile Glu Ser Leu Gly Pro Asp Thr Ile Ala Ala Phe
        210                 215                 220

Leu Ala Glu Pro Ile Leu Ala Ser Gly Gly Val Ile Ile Pro Pro Ala
225                 230                 235                 240

Gly Tyr His Ala Arg Phe Lys Ala Ile Cys Glu Lys His Asp Ile Leu
                245                 250                 255

Tyr Ile Ser Asp Glu Val Val Thr Gly Phe Gly Arg Cys Gly Glu Trp
                260                 265                 270

Phe Ala Ser Glu Lys Val Phe Gly Val Val Pro Asp Ile Ile Thr Phe
            275                 280                 285
```

Ala Lys Gly Val Thr Ser Gly Tyr Val Pro Leu Gly Gly Leu Ala Ile
            290                 295                 300

Ser Glu Ala Val Leu Ala Arg Ile Ser Gly Glu Asn Ala Lys Gly Ser
305                 310                 315                 320

Trp Phe Thr Asn Gly Tyr Thr Tyr Ser Asn Gln Pro Val Ala Cys Ala
                325                 330                 335

Ala Ala Leu Ala Asn Ile Glu Leu Met Glu Arg Glu Gly Ile Val Asp
            340                 345                 350

Gln Ala Arg Glu Met Ala Asp Tyr Phe Ala Ala Leu Ala Ser Leu
        355                 360                 365

Arg Asp Leu Pro Gly Val Ala Glu Thr Arg Ser Val Gly Leu Val Gly
370                 375                 380

Cys Val Gln Cys Leu Leu Asp Pro Thr Arg Ala Asp Gly Thr Ala Glu
385                 390                 395                 400

Asp Lys Ala Phe Thr Leu Lys Ile Asp Glu Arg Cys Phe Glu Leu Gly
                405                 410                 415

Leu Ile Val Arg Pro Leu Gly Asp Leu Cys Val Ile Ser Pro Pro Leu
            420                 425                 430

Ile Ile Ser Arg Ala Gln Ile Asp Glu Met Val Ala Ile Met Arg Gln
            435                 440                 445

Ala Ile Thr Glu Val Ser Ala Ala His Gly Leu Thr Ala Lys Glu Pro
450                 455                 460

Ala Ala Val
465

<210> SEQ ID NO 11
<211> LENGTH: 459
<212> TYPE: PRT
<213> ORGANISM: Escherichia coli

<400> SEQUENCE: 11

Met Asn Arg Leu Pro Ser Ser Ala Ser Ala Leu Ala Cys Ser Ala His
1               5                   10                  15

Ala Leu Asn Leu Ile Glu Lys Arg Thr Leu Asp His Glu Glu Met Lys
            20                  25                  30

Ala Leu Asn Arg Glu Val Ile Glu Tyr Phe Lys Glu His Val Asn Pro
        35                  40                  45

Gly Phe Leu Glu Tyr Arg Lys Ser Val Thr Ala Gly Gly Asp Tyr Gly
    50                  55                  60

Ala Val Glu Trp Gln Ala Gly Ser Leu Asn Thr Leu Val Asp Thr Gln
65                  70                  75                  80

Gly Gln Glu Phe Ile Asp Cys Leu Gly Gly Phe Gly Ile Phe Asn Val
                85                  90                  95

Gly His Arg Asn Pro Val Val Ser Ala Val Gln Asn Gln Leu Ala
            100                 105                 110

Lys Gln Pro Leu His Ser Gln Glu Leu Leu Asp Pro Leu Arg Ala Met
        115                 120                 125

Leu Ala Lys Thr Leu Ala Ala Leu Thr Pro Gly Lys Leu Lys Tyr Ser
    130                 135                 140

Phe Phe Cys Asn Ser Gly Thr Glu Ser Val Glu Ala Ala Leu Lys Leu
145                 150                 155                 160

Ala Lys Ala Tyr Gln Ser Pro Arg Gly Lys Phe Thr Phe Ile Ala Thr
                165                 170                 175

Ser Gly Ala Phe His Gly Lys Ser Leu Gly Ala Leu Ser Ala Thr Ala

```
            180                 185                 190
Lys Ser Thr Phe Arg Lys Pro Phe Met Pro Leu Leu Pro Gly Phe Arg
                195                 200                 205

His Val Pro Phe Gly Asn Ile Glu Ala Met Arg Thr Ala Leu Asn Glu
    210                 215                 220

Cys Lys Lys Thr Gly Asp Asp Val Ala Val Ile Leu Glu Pro Ile
225                 230                 235                 240

Gln Gly Glu Gly Val Ile Leu Pro Pro Gly Tyr Leu Thr Ala
                245                 250                 255

Val Arg Lys Leu Cys Asp Glu Phe Gly Ala Leu Met Ile Leu Asp Glu
                260                 265                 270

Val Gln Thr Gly Met Gly Arg Thr Gly Lys Met Phe Ala Cys Glu His
                275                 280                 285

Glu Asn Val Gln Pro Asp Ile Leu Cys Leu Ala Lys Ala Leu Gly Gly
                290                 295                 300

Gly Val Met Pro Ile Gly Ala Thr Ile Ala Thr Glu Glu Val Phe Ser
305                 310                 315                 320

Val Leu Phe Asp Asn Pro Phe Leu His Thr Thr Phe Gly Gly Asn
                325                 330                 335

Pro Leu Ala Cys Ala Ala Ala Leu Ala Thr Ile Asn Val Leu Leu Glu
                340                 345                 350

Gln Asn Leu Pro Ala Gln Ala Glu Gln Lys Gly Asp Met Leu Leu Asp
                355                 360                 365

Gly Phe Arg Gln Leu Ala Arg Glu Tyr Pro Asp Leu Val Gln Glu Ala
                370                 375                 380

Arg Gly Lys Gly Met Leu Met Ala Ile Glu Phe Val Asp Asn Glu Ile
385                 390                 395                 400

Gly Tyr Asn Phe Ala Ser Glu Met Phe Arg Gln Arg Val Leu Val Ala
                405                 410                 415

Gly Thr Leu Asn Asn Ala Lys Thr Ile Arg Ile Glu Pro Pro Leu Thr
                420                 425                 430

Leu Thr Ile Glu Gln Cys Glu Leu Val Ile Lys Ala Ala Arg Lys Ala
                435                 440                 445

Leu Ala Met Arg Val Ser Val Glu Glu Ala
                450                 455

<210> SEQ ID NO 12
<211> LENGTH: 453
<212> TYPE: PRT
<213> ORGANISM: Vibrio fluvialis

<400> SEQUENCE: 12

Met Asn Lys Pro Gln Ser Trp Glu Ala Arg Ala Glu Thr Tyr Ser Leu
1               5                   10                  15

Tyr Gly Phe Thr Asp Met Pro Ser Leu His Gln Arg Gly Thr Val Val
                20                  25                  30

Val Thr His Gly Glu Gly Pro Tyr Ile Val Asp Val Asn Gly Arg Arg
            35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65              70                  75                  80

Gly Tyr His Ala Phe Phe Gly Arg Met Ser Asp Gln Thr Val Met Leu
                85                  90                  95
```

Ser Glu Lys Leu Val Glu Val Ser Pro Phe Asp Ser Gly Arg Val Phe
                100                 105                 110

Tyr Thr Asn Ser Gly Ser Glu Ala Asn Asp Thr Met Val Lys Met Leu
            115                 120                 125

Trp Phe Leu His Ala Ala Glu Gly Lys Pro Gln Lys Arg Lys Ile Leu
        130                 135                 140

Thr Arg Trp Asn Ala Tyr His Gly Val Thr Ala Val Ser Ala Ser Met
145                 150                 155                 160

Thr Gly Lys Pro Tyr Asn Ser Val Phe Gly Leu Pro Leu Pro Gly Phe
                165                 170                 175

Val His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Arg Glu Gly Ala Asp Thr Ile Ala Gly Phe Phe Ala Glu Pro
210                 215                 220

Val Met Gly Ala Gly Gly Val Ile Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Met Gly Ala Val Ile Leu Gly Pro Glu Leu Ser
290                 295                 300

Lys Arg Leu Glu Thr Ala Ile Glu Ala Ile Glu Glu Phe Pro His Gly
305                 310                 315                 320

Phe Thr Ala Ser Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Ala Val
370                 375                 380

Lys Asp Lys Ala Ser Lys Thr Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450

<210> SEQ ID NO 13
<211> LENGTH: 401
<212> TYPE: PRT
<213> ORGANISM: Escherichia coli

<400> SEQUENCE: 13

Met Arg Glu Ala Phe Ile Cys Asp Gly Ile Arg Thr Pro Ile Gly Arg
1               5                   10                  15

Tyr Gly Gly Ala Leu Ser Ser Val Arg Ala Asp Asp Leu Ala Ala Ile
            20                  25                  30

Pro Leu Arg Glu Leu Leu Val Arg Asn Pro Arg Leu Asp Ala Glu Cys
        35                  40                  45

Ile Asp Asp Val Ile Leu Gly Cys Ala Asn Gln Ala Gly Glu Asp Asn
 50                  55                  60

Arg Asn Val Ala Arg Met Ala Thr Leu Leu Ala Gly Leu Pro Gln Ser
 65                  70                  75                  80

Val Ser Gly Thr Thr Ile Asn Arg Leu Cys Gly Ser Gly Leu Asp Ala
                85                  90                  95

Leu Gly Phe Ala Ala Arg Ala Ile Lys Ala Gly Asp Gly Asp Leu Leu
            100                 105                 110

Ile Ala Gly Gly Val Glu Ser Met Ser Arg Ala Pro Phe Val Met Gly
            115                 120                 125

Lys Ala Ala Ser Ala Phe Ser Arg Gln Ala Glu Met Phe Asp Thr Thr
130                 135                 140

Ile Gly Trp Arg Phe Val Asn Pro Leu Met Ala Gln Gln Phe Gly Thr
145                 150                 155                 160

Asp Ser Met Pro Glu Thr Ala Glu Asn Val Ala Glu Leu Leu Lys Ile
                165                 170                 175

Ser Arg Glu Asp Gln Asp Ser Phe Ala Leu Arg Ser Gln Gln Arg Thr
            180                 185                 190

Ala Lys Ala Gln Ser Ser Gly Ile Leu Ala Glu Glu Ile Val Pro Val
            195                 200                 205

Val Leu Lys Asn Lys Lys Gly Val Val Thr Glu Ile Gln His Asp Glu
210                 215                 220

His Leu Arg Pro Glu Thr Thr Leu Glu Gln Leu Arg Gly Leu Lys Ala
225                 230                 235                 240

Pro Phe Arg Ala Asn Gly Val Ile Thr Ala Gly Asn Ala Ser Gly Val
                245                 250                 255

Asn Asp Gly Ala Ala Ala Leu Ile Ile Ala Ser Glu Gln Met Ala Ala
            260                 265                 270

Ala Gln Gly Leu Thr Pro Arg Ala Arg Ile Val Ala Met Ala Thr Ala
            275                 280                 285

Gly Val Glu Pro Arg Leu Met Gly Leu Gly Pro Val Pro Ala Thr Arg
            290                 295                 300

Arg Val Leu Glu Arg Ala Gly Leu Ser Ile His Asp Met Asp Val Ile
305                 310                 315                 320

Glu Leu Asn Glu Ala Phe Ala Ala Gln Ala Leu Gly Val Leu Arg Glu
                325                 330                 335

Leu Gly Leu Pro Asp Asp Ala Pro His Val Asn Pro Asn Gly Gly Ala
            340                 345                 350

Ile Ala Leu Gly His Pro Leu Gly Met Ser Gly Ala Arg Leu Ala Leu
            355                 360                 365

Ala Ala Ser His Glu Leu His Arg Arg Asn Gly Arg Tyr Ala Leu Cys
            370                 375                 380

Thr Met Cys Ile Gly Val Gly Gln Gly Ile Ala Met Ile Leu Glu Arg
385                 390                 395                 400

Val

<210> SEQ ID NO 14
<211> LENGTH: 325
<212> TYPE: PRT

<213> ORGANISM: Bacillus subtilis

<400> SEQUENCE: 14

Met Ser Lys Ala Lys Ile Thr Ala Ile Gly Thr Tyr Ala Pro Ser Arg
1               5                   10                  15

Arg Leu Thr Asn Ala Asp Leu Glu Lys Ile Val Asp Thr Ser Asp Glu
            20                  25                  30

Trp Ile Val Gln Arg Thr Gly Met Arg Glu Arg Ile Ala Asp Glu
        35                  40                  45

His Gln Phe Thr Ser Asp Leu Cys Ile Glu Ala Val Lys Asn Leu Lys
    50                  55                  60

Ser Arg Tyr Lys Gly Thr Leu Asp Asp Val Asp Met Ile Leu Val Ala
65                  70                  75                  80

Thr Thr Thr Ser Asp Tyr Ala Phe Pro Ser Thr Ala Cys Arg Val Gln
                85                  90                  95

Glu Tyr Phe Gly Trp Glu Ser Thr Gly Ala Leu Asp Ile Asn Ala Thr
            100                 105                 110

Cys Ala Gly Leu Thr Tyr Gly Leu His Leu Ala Asn Gly Leu Ile Thr
        115                 120                 125

Ser Gly Leu His Gln Lys Ile Leu Val Ile Ala Gly Glu Thr Leu Ser
    130                 135                 140

Lys Val Thr Asp Tyr Thr Asp Arg Thr Thr Cys Val Leu Phe Gly Asp
145                 150                 155                 160

Ala Ala Gly Ala Leu Leu Val Glu Arg Asp Glu Glu Thr Pro Gly Phe
                165                 170                 175

Leu Ala Ser Val Gln Gly Thr Ser Gly Asn Gly Gly Asp Ile Leu Tyr
            180                 185                 190

Arg Ala Gly Leu Arg Asn Glu Ile Asn Gly Val Gln Leu Val Gly Ser
        195                 200                 205

Gly Lys Met Val Gln Asn Gly Arg Glu Val Tyr Lys Trp Ala Ala Arg
    210                 215                 220

Thr Val Pro Gly Glu Phe Glu Arg Leu Leu His Lys Ala Gly Leu Ser
225                 230                 235                 240

Ser Asp Asp Leu Asp Trp Phe Val Pro His Ser Ala Asn Leu Arg Met
                245                 250                 255

Ile Glu Ser Ile Cys Glu Lys Thr Pro Phe Pro Ile Gly Lys Thr Leu
            260                 265                 270

Thr Ser Val Glu His Tyr Gly Asn Thr Ser Ser Val Ser Ile Val Leu
        275                 280                 285

Ala Leu Asp Leu Ala Val Lys Ala Gly Lys Leu Lys Lys Asp Gln Ile
    290                 295                 300

Val Leu Leu Phe Gly Phe Gly Gly Gly Leu Thr Tyr Thr Gly Leu Leu
305                 310                 315                 320

Ile Lys Trp Gly Met
                325

<210> SEQ ID NO 15
<211> LENGTH: 1168
<212> TYPE: PRT
<213> ORGANISM: Mycobacterium smegmatis

<400> SEQUENCE: 15

Met Thr Ile Glu Thr Arg Glu Asp Arg Phe Asn Arg Arg Ile Asp His
1               5                   10                  15

Leu Phe Glu Thr Asp Pro Gln Phe Ala Ala Ala Arg Pro Asp Glu Ala

```
                    20                  25                  30
Ile Ser Ala Ala Ala Asp Pro Glu Leu Arg Leu Pro Ala Ala Val
            35                  40                  45
Lys Gln Ile Leu Ala Gly Tyr Ala Asp Arg Pro Ala Leu Gly Lys Arg
 50                  55                  60
Ala Val Glu Phe Val Thr Asp Glu Glu Gly Arg Thr Thr Ala Lys Leu
 65                  70                  75                  80
Leu Pro Arg Phe Asp Thr Ile Thr Tyr Arg Gln Leu Ala Gly Arg Ile
                85                  90                  95
Gln Ala Val Thr Asn Ala Trp His Asn His Pro Val Asn Ala Gly Asp
                100                 105                 110
Arg Val Ala Ile Leu Gly Phe Thr Ser Val Asp Tyr Thr Thr Ile Asp
                115                 120                 125
Ile Ala Leu Leu Glu Leu Gly Ala Val Ser Val Pro Leu Gln Thr Ser
                130                 135                 140
Ala Pro Val Ala Gln Leu Gln Pro Ile Val Ala Glu Thr Glu Pro Lys
145                 150                 155                 160
Val Ile Ala Ser Ser Val Asp Phe Leu Ala Asp Ala Val Ala Leu Val
                165                 170                 175
Glu Ser Gly Pro Ala Pro Ser Arg Leu Val Val Phe Asp Tyr Ser His
                180                 185                 190
Glu Val Asp Asp Gln Arg Glu Ala Phe Glu Ala Ala Lys Gly Lys Leu
                195                 200                 205
Ala Gly Thr Gly Val Val Glu Thr Ile Thr Asp Ala Leu Asp Arg
                210                 215                 220
Gly Arg Ser Leu Ala Asp Ala Pro Leu Tyr Val Pro Asp Glu Ala Asp
225                 230                 235                 240
Pro Leu Thr Leu Leu Ile Tyr Thr Ser Gly Ser Thr Gly Thr Pro Lys
                245                 250                 255
Gly Ala Met Tyr Pro Glu Ser Lys Thr Ala Thr Met Trp Gln Ala Gly
                260                 265                 270
Ser Lys Ala Arg Trp Asp Glu Thr Leu Gly Val Met Pro Ser Ile Thr
                275                 280                 285
Leu Asn Phe Met Pro Met Ser His Val Met Gly Arg Gly Ile Leu Cys
                290                 295                 300
Ser Thr Leu Ala Ser Gly Gly Thr Ala Tyr Phe Ala Ala Arg Ser Asp
305                 310                 315                 320
Leu Ser Thr Phe Leu Glu Asp Leu Ala Leu Val Arg Pro Thr Gln Leu
                325                 330                 335
Asn Phe Val Pro Arg Ile Trp Asp Met Leu Phe Gln Glu Tyr Gln Ser
                340                 345                 350
Arg Leu Asp Asn Arg Arg Ala Glu Gly Ser Glu Asp Arg Ala Glu Ala
                355                 360                 365
Ala Val Leu Glu Glu Val Arg Thr Gln Leu Leu Gly Gly Arg Phe Val
                370                 375                 380
Ser Ala Leu Thr Gly Ser Ala Pro Ile Ser Ala Glu Met Lys Ser Trp
385                 390                 395                 400
Val Glu Asp Leu Leu Asp Met His Leu Leu Glu Gly Tyr Gly Ser Thr
                405                 410                 415
Glu Ala Gly Ala Val Phe Ile Asp Gly Gln Ile Gln Arg Pro Pro Val
                420                 425                 430
Ile Asp Tyr Lys Leu Val Asp Val Pro Asp Leu Gly Tyr Phe Ala Thr
                435                 440                 445
```

-continued

Asp Arg Pro Tyr Pro Arg Gly Glu Leu Leu Val Lys Ser Glu Gln Met
450                455                460

Phe Pro Gly Tyr Tyr Lys Arg Pro Glu Ile Thr Ala Glu Met Phe Asp
465                    470                475                480

Glu Asp Gly Tyr Tyr Arg Thr Gly Asp Ile Val Ala Glu Leu Gly Pro
                   485                490                495

Asp His Leu Glu Tyr Leu Asp Arg Arg Asn Asn Val Leu Lys Leu Ser
                500                505                510

Gln Gly Glu Phe Val Thr Val Ser Lys Leu Glu Ala Val Phe Gly Asp
            515                520                525

Ser Pro Leu Val Arg Gln Ile Tyr Val Tyr Gly Asn Ser Ala Arg Ser
530                535                540

Tyr Leu Leu Ala Val Val Pro Thr Glu Glu Ala Leu Ser Arg Trp
545                550                555                560

Asp Gly Asp Glu Leu Lys Ser Arg Ile Ser Asp Ser Leu Gln Asp Ala
                565                570                575

Ala Arg Ala Ala Gly Leu Gln Ser Tyr Glu Ile Pro Arg Asp Phe Leu
            580                585                590

Val Glu Thr Thr Pro Phe Thr Leu Glu Asn Gly Leu Leu Thr Gly Ile
        595                600                605

Arg Lys Leu Ala Arg Pro Lys Leu Lys Ala His Tyr Gly Glu Arg Leu
610                615                620

Glu Gln Leu Tyr Thr Asp Leu Ala Glu Gly Gln Ala Asn Glu Leu Arg
625                630                635                640

Glu Leu Arg Arg Asn Gly Ala Asp Arg Pro Val Val Glu Thr Val Ser
                645                650                655

Arg Ala Ala Val Ala Leu Leu Gly Ala Ser Val Thr Asp Leu Arg Ser
            660                665                670

Asp Ala His Phe Thr Asp Leu Gly Gly Asp Ser Leu Ser Ala Leu Ser
            675                680                685

Phe Ser Asn Leu Leu His Glu Ile Phe Asp Val Asp Val Pro Val Gly
690                695                700

Val Ile Val Ser Pro Ala Thr Asp Leu Ala Gly Val Ala Ala Tyr Ile
705                710                715                720

Glu Gly Glu Leu Arg Gly Ser Lys Arg Pro Thr Tyr Ala Ser Val His
                725                730                735

Gly Arg Asp Ala Thr Glu Val Arg Ala Arg Asp Leu Ala Leu Gly Lys
            740                745                750

Phe Ile Asp Ala Lys Thr Leu Ser Ala Ala Pro Gly Leu Pro Arg Ser
755                760                765

Gly Thr Glu Ile Arg Thr Val Leu Leu Thr Gly Ala Thr Gly Phe Leu
770                775                780

Gly Arg Tyr Leu Ala Leu Glu Trp Leu Glu Arg Met Asp Leu Val Asp
785                790                795                800

Gly Lys Val Ile Cys Leu Val Arg Ala Arg Ser Asp Asp Glu Ala Arg
                805                810                815

Ala Arg Leu Asp Ala Thr Phe Asp Thr Gly Asp Ala Thr Leu Leu Glu
            820                825                830

His Tyr Arg Ala Leu Ala Ala Asp His Leu Glu Val Ile Ala Gly Asp
        835                840                845

Lys Gly Glu Ala Asp Leu Gly Leu Asp His Asp Thr Trp Gln Arg Leu
850                855                860

Ala Asp Thr Val Asp Leu Ile Val Asp Pro Ala Leu Val Asn His
865                 870                 875                 880

Val Leu Pro Tyr Ser Gln Met Phe Gly Pro Asn Ala Leu Gly Thr Ala
            885                 890                 895

Glu Leu Ile Arg Ile Ala Leu Thr Thr Thr Ile Lys Pro Tyr Val Tyr
        900                 905                 910

Val Ser Thr Ile Gly Val Gly Gln Gly Ile Ser Pro Glu Ala Phe Val
    915                 920                 925

Glu Asp Ala Asp Ile Arg Glu Ile Ser Ala Thr Arg Arg Val Asp Asp
930                 935                 940

Ser Tyr Ala Asn Gly Tyr Gly Asn Ser Lys Trp Ala Gly Glu Val Leu
945                 950                 955                 960

Leu Arg Glu Ala His Asp Trp Cys Gly Leu Pro Val Ser Val Phe Arg
            965                 970                 975

Cys Asp Met Ile Leu Ala Asp Thr Thr Tyr Ser Gly Gln Leu Asn Leu
        980                 985                 990

Pro Asp Met Phe Thr Arg Leu Met Leu Ser Leu Val Ala Thr Gly Ile
    995                 1000                1005

Ala Pro Gly Ser Phe Tyr Glu Leu Asp Ala Asp Gly Asn Arg Gln
    1010                1015                1020

Arg Ala His Tyr Asp Gly Leu Pro Val Glu Phe Ile Ala Glu Ala
    1025                1030                1035

Ile Ser Thr Ile Gly Ser Gln Val Thr Asp Gly Phe Glu Thr Phe
    1040                1045                1050

His Val Met Asn Pro Tyr Asp Asp Gly Ile Gly Leu Asp Glu Tyr
    1055                1060                1065

Val Asp Trp Leu Ile Glu Gly Tyr Pro Val His Arg Val Asp
    1070                1075                1080

Asp Tyr Ala Thr Trp Leu Ser Arg Phe Glu Thr Ala Leu Arg Ala
    1085                1090                1095

Leu Pro Glu Arg Gln Arg Gln Ala Ser Leu Leu Pro Leu Leu His
    1100                1105                1110

Asn Tyr Gln Gln Pro Ser Pro Pro Val Cys Gly Ala Met Ala Pro
    1115                1120                1125

Thr Asp Arg Phe Arg Ala Val Gln Asp Ala Lys Ile Gly Pro
    1130                1135                1140

Asp Lys Asp Ile Pro His Val Thr Ala Asp Val Val Lys Tyr
    1145                1150                1155

Ile Ser Asn Leu Gln Met Leu Gly Leu Leu
    1160                1165

<210> SEQ ID NO 16
<211> LENGTH: 393
<212> TYPE: PRT
<213> ORGANISM: Cupriavidus necator

<400> SEQUENCE: 16

Met Thr Arg Glu Val Val Val Ser Gly Val Arg Thr Ala Ile Gly
1               5                   10                  15

Thr Phe Gly Gly Ser Leu Lys Asp Val Ala Pro Ala Glu Leu Gly Ala
            20                  25                  30

Leu Val Val Arg Glu Ala Leu Ala Arg Ala Gln Val Ser Gly Asp Asp
        35                  40                  45

Val Gly His Val Val Phe Gly Asn Val Ile Gln Thr Glu Pro Arg Asp
    50                  55                  60

Met Tyr Leu Gly Arg Val Ala Val Asn Gly Val Thr Ile Asn
65                  70                  75                  80

Ala Pro Ala Leu Thr Val Asn Arg Leu Cys Gly Ser Gly Leu Gln Ala
                85                  90                  95

Ile Val Ser Ala Ala Gln Thr Ile Leu Leu Gly Asp Thr Asp Val Ala
            100                 105                 110

Ile Gly Gly Gly Ala Glu Ser Met Ser Arg Ala Pro Tyr Leu Ala Pro
            115                 120                 125

Ala Ala Arg Trp Gly Ala Arg Met Gly Asp Ala Gly Leu Val Asp Met
            130                 135                 140

Met Leu Gly Ala Leu His Asp Pro Phe His Arg Ile His Met Gly Val
145                 150                 155                 160

Thr Ala Glu Asn Val Ala Lys Glu Tyr Asp Ile Ser Arg Ala Gln Gln
                165                 170                 175

Asp Glu Ala Ala Leu Glu Ser His Arg Arg Ala Ser Ala Ala Ile Lys
            180                 185                 190

Ala Gly Tyr Phe Lys Asp Gln Ile Val Pro Val Val Ser Lys Gly Arg
            195                 200                 205

Lys Gly Asp Val Thr Phe Asp Thr Asp Glu His Val Arg His Asp Ala
210                 215                 220

Thr Ile Asp Asp Met Thr Lys Leu Arg Pro Val Phe Val Lys Glu Asn
225                 230                 235                 240

Gly Thr Val Thr Ala Gly Asn Ala Ser Gly Leu Asn Asp Ala Ala Ala
                245                 250                 255

Ala Val Val Met Met Glu Arg Ala Glu Ala Arg Arg Gly Leu Lys
            260                 265                 270

Pro Leu Ala Arg Leu Val Ser Tyr His Ala Gly Val Asp Pro Lys Ala
            275                 280                 285

Met Gly Ile Gly Pro Val Pro Ala Thr Lys Ile Ala Leu Glu Arg Ala
            290                 295                 300

Gly Leu Gln Val Ser Asp Leu Asp Val Ile Glu Ala Asn Glu Ala Phe
305                 310                 315                 320

Ala Ala Gln Ala Cys Ala Val Thr Lys Ala Leu Gly Leu Asp Pro Ala
            325                 330                 335

Lys Val Asn Pro Asn Gly Ser Gly Ile Ser Leu Gly His Pro Ile Gly
            340                 345                 350

Ala Thr Gly Ala Leu Ile Thr Val Lys Ala Leu His Glu Leu Asn Arg
            355                 360                 365

Val Gln Gly Arg Tyr Ala Leu Val Thr Met Cys Ile Gly Gly Gly Gln
            370                 375                 380

Gly Ile Ala Ala Ile Phe Glu Arg Ile
385                 390

<210> SEQ ID NO 17
<211> LENGTH: 401
<212> TYPE: PRT
<213> ORGANISM: Escherichia coli

<400> SEQUENCE: 17

Met Arg Glu Ala Phe Ile Cys Asp Gly Ile Arg Thr Pro Ile Gly Arg
1               5                   10                  15

Tyr Gly Gly Ala Leu Ser Ser Val Arg Ala Asp Asp Leu Ala Ala Ile
            20                  25                  30

Pro Leu Arg Glu Leu Leu Val Arg Asn Pro Arg Leu Asp Ala Glu Cys

```
            35                  40                  45
Ile Asp Asp Val Ile Leu Gly Cys Ala Asn Gln Ala Gly Glu Asp Asn
 50                  55                  60

Arg Asn Val Ala Arg Met Ala Thr Leu Leu Ala Gly Leu Pro Gln Ser
 65                  70                  75                  80

Val Ser Gly Thr Thr Ile Asn Arg Leu Cys Gly Ser Gly Leu Asp Ala
                 85                  90                  95

Leu Gly Phe Ala Ala Arg Ala Ile Lys Ala Gly Asp Gly Asp Leu Leu
                100                 105                 110

Ile Ala Gly Gly Val Glu Ser Met Ser Arg Ala Pro Phe Val Met Gly
            115                 120                 125

Lys Ala Ser Ala Phe Ser Arg Gln Ala Glu Met Phe Asp Thr Thr
        130                 135                 140

Ile Gly Trp Arg Phe Val Asn Pro Leu Met Ala Gln Gln Phe Gly Thr
145                 150                 155                 160

Asp Ser Met Pro Glu Thr Ala Glu Asn Val Ala Glu Leu Leu Lys Ile
                165                 170                 175

Ser Arg Glu Asp Gln Asp Ser Phe Ala Leu Arg Ser Gln Gln Arg Thr
                180                 185                 190

Ala Lys Ala Gln Ser Ser Gly Ile Leu Ala Glu Glu Ile Val Pro Val
            195                 200                 205

Val Leu Lys Asn Lys Lys Gly Val Val Thr Glu Ile Gln His Asp Glu
210                 215                 220

His Leu Arg Pro Glu Thr Thr Leu Glu Gln Leu Arg Gly Leu Lys Ala
225                 230                 235                 240

Pro Phe Arg Ala Asn Gly Val Ile Thr Ala Gly Asn Ala Ser Gly Val
                245                 250                 255

Asn Asp Gly Ala Ala Ala Leu Ile Ile Ala Ser Glu Gln Met Ala Ala
            260                 265                 270

Ala Gln Gly Leu Thr Pro Arg Ala Arg Ile Val Ala Met Ala Thr Ala
        275                 280                 285

Gly Val Glu Pro Arg Leu Met Gly Leu Gly Pro Val Pro Ala Thr Arg
290                 295                 300

Arg Val Leu Glu Arg Ala Gly Leu Ser Ile His Asp Met Asp Val Ile
305                 310                 315                 320

Glu Leu Asn Glu Ala Phe Ala Ala Gln Ala Leu Gly Val Leu Arg Glu
                325                 330                 335

Leu Gly Leu Pro Asp Asp Ala Pro His Val Asn Pro Asn Gly Gly Ala
                340                 345                 350

Ile Ala Leu Gly His Pro Leu Gly Met Ser Gly Ala Arg Leu Ala Leu
            355                 360                 365

Ala Ala Ser His Glu Leu His Arg Arg Asn Gly Arg Tyr Ala Leu Cys
        370                 375                 380

Thr Met Cys Ile Gly Val Gly Gln Gly Ile Ala Met Ile Leu Glu Arg
385                 390                 395                 400

Val

<210> SEQ ID NO 18
<211> LENGTH: 524
<212> TYPE: PRT
<213> ORGANISM: Clostridium propionicum

<400> SEQUENCE: 18

Met Arg Lys Val Pro Ile Ile Thr Ala Asp Glu Ala Ala Lys Leu Ile
```

-continued

```
1               5                   10                  15
Lys Asp Gly Asp Thr Val Thr Thr Ser Gly Phe Val Gly Asn Ala Ile
                20                  25                  30

Pro Glu Ala Leu Asp Arg Ala Val Glu Lys Arg Phe Leu Glu Thr Gly
                35                  40                  45

Glu Pro Lys Asn Ile Thr Tyr Val Tyr Cys Gly Ser Gln Gly Asn Arg
 50                  55                  60

Asp Gly Arg Gly Ala Glu His Phe Ala His Glu Gly Leu Leu Lys Arg
 65                  70                  75                  80

Tyr Ile Ala Gly His Trp Ala Thr Val Pro Ala Leu Gly Lys Met Ala
                85                  90                  95

Met Glu Asn Lys Met Glu Ala Tyr Asn Val Ser Gln Gly Ala Leu Cys
                100                 105                 110

His Leu Phe Arg Asp Ile Ala Ser His Lys Pro Gly Val Phe Thr Lys
                115                 120                 125

Val Gly Ile Gly Thr Phe Ile Asp Pro Arg Asn Gly Gly Lys Val
                130                 135                 140

Asn Asp Ile Thr Lys Glu Asp Ile Val Glu Leu Val Glu Ile Lys Gly
145                 150                 155                 160

Gln Glu Tyr Leu Phe Tyr Pro Ala Phe Pro Ile His Val Ala Leu Ile
                165                 170                 175

Arg Gly Thr Tyr Ala Asp Glu Ser Gly Asn Ile Thr Phe Glu Lys Glu
                180                 185                 190

Val Ala Pro Leu Glu Gly Thr Ser Val Cys Gln Ala Val Lys Asn Ser
                195                 200                 205

Gly Gly Ile Val Val Gln Val Glu Arg Val Val Lys Ala Gly Thr
                210                 215                 220

Leu Asp Pro Arg His Val Lys Val Pro Gly Ile Tyr Val Asp Tyr Val
225                 230                 235                 240

Val Val Ala Asp Pro Glu Asp His Gln Gln Ser Leu Asp Cys Glu Tyr
                245                 250                 255

Asp Pro Ala Leu Ser Gly Glu His Arg Arg Pro Glu Val Val Gly Glu
                260                 265                 270

Pro Leu Pro Leu Ser Ala Lys Lys Val Ile Gly Arg Gly Ala Ile
                275                 280                 285

Glu Leu Glu Lys Asp Val Ala Val Asn Leu Gly Val Gly Ala Pro Glu
                290                 295                 300

Tyr Val Ala Ser Val Ala Asp Glu Glu Gly Ile Val Asp Phe Met Thr
305                 310                 315                 320

Leu Thr Ala Glu Ser Gly Ala Ile Gly Gly Val Pro Ala Gly Gly Val
                325                 330                 335

Arg Phe Gly Ala Ser Tyr Asn Ala Asp Ala Leu Ile Asp Gln Gly Tyr
                340                 345                 350

Gln Phe Asp Tyr Tyr Asp Gly Gly Leu Asp Leu Cys Tyr Leu Gly
                355                 360                 365

Leu Ala Glu Cys Asp Glu Lys Gly Asn Ile Asn Val Ser Arg Phe Gly
                370                 375                 380

Pro Arg Ile Ala Gly Cys Gly Phe Ile Asn Ile Thr Gln Asn Thr
385                 390                 395                 400

Pro Lys Val Phe Phe Cys Gly Thr Phe Thr Ala Gly Gly Leu Lys Val
                405                 410                 415

Lys Ile Glu Asp Gly Lys Val Ile Ile Val Gln Glu Gly Lys Gln Lys
                420                 425                 430
```

```
Lys Phe Leu Lys Ala Val Glu Gln Ile Thr Phe Asn Gly Asp Val Ala
        435                 440                 445

Leu Ala Asn Lys Gln Gln Val Thr Tyr Ile Thr Glu Arg Cys Val Phe
    450                 455                 460

Leu Leu Lys Glu Asp Gly Leu His Leu Ser Glu Ile Ala Pro Gly Ile
465                 470                 475                 480

Asp Leu Gln Thr Gln Ile Leu Asp Val Met Asp Phe Ala Pro Ile Ile
                485                 490                 495

Asp Arg Asp Ala Asn Gly Gln Ile Lys Leu Met Asp Ala Ala Leu Phe
            500                 505                 510

Ala Glu Gly Leu Met Gly Leu Lys Glu Met Lys Ser
        515                 520

<210> SEQ ID NO 19
<211> LENGTH: 438
<212> TYPE: PRT
<213> ORGANISM: Clostridium aminobutyricum

<400> SEQUENCE: 19

Met Asp Trp Lys Lys Ile Tyr Glu Asp Arg Thr Cys Thr Ala Asp Glu
1               5                   10                  15

Ala Val Lys Ser Ile Lys Ser Gly Asp Arg Val Leu Phe Ala His Cys
            20                  25                  30

Val Ala Glu Pro Pro Val Leu Val Glu Ala Met Val Ala Asn Ala Ala
        35                  40                  45

Ala Tyr Lys Asn Val Thr Val Ser His Met Val Thr Leu Gly Lys Gly
    50                  55                  60

Glu Tyr Ser Lys Pro Glu Tyr Lys Glu Asn Phe Thr Phe Glu Gly Trp
65                  70                  75                  80

Phe Thr Ser Pro Ser Thr Arg Gly Ser Ile Ala Glu Gly His Gly Gln
                85                  90                  95

Phe Val Pro Val Phe Phe His Glu Val Pro Ser Leu Ile Arg Lys Asp
            100                 105                 110

Ile Phe His Val Asp Val Phe Met Val Met Val Ser Pro Pro Asp His
        115                 120                 125

Asn Gly Phe Cys Cys Val Gly Val Ser Ser Asp Tyr Thr Met Gln Ala
    130                 135                 140

Ile Lys Ser Ala Lys Ile Val Leu Ala Glu Val Asn Asp Gln Val Pro
145                 150                 155                 160

Val Val Tyr Gly Asp Thr Phe Val His Val Ser Glu Ile Asp Lys Phe
                165                 170                 175

Val Glu Thr Ser His Pro Leu Pro Glu Ile Gly Leu Pro Lys Ile Gly
            180                 185                 190

Glu Val Glu Ala Ala Ile Gly Lys His Cys Ala Ser Leu Ile Glu Asp
        195                 200                 205

Gly Ser Thr Leu Gln Leu Gly Ile Gly Ala Ile Pro Asp Ala Val Leu
    210                 215                 220

Ser Gln Leu Lys Asp Lys Lys His Leu Gly Ile His Ser Glu Met Ile
225                 230                 235                 240

Ser Asp Gly Val Val Asp Leu Tyr Glu Ala Gly Val Ile Asp Cys Ser
                245                 250                 255

Gln Lys Ser Ile Asp Lys Gly Lys Met Ala Ile Thr Phe Leu Met Gly
            260                 265                 270

Thr Lys Arg Leu Tyr Asp Phe Ala Ala Asn Asn Pro Lys Val Glu Leu
```

```
            275                 280                 285
Lys Pro Val Asp Tyr Ile Asn His Pro Ser Val Ala Gln Cys Ser
290                 295                 300

Lys Met Val Cys Ile Asn Ala Cys Leu Gln Val Asp Phe Met Gly Gln
305                 310                 315                 320

Ile Val Ser Asp Ser Ile Gly Thr Lys Gln Phe Ser Gly Val Gly Gly
                325                 330                 335

Gln Val Asp Phe Val Arg Gly Ala Ser Met Ser Ile Asp Gly Lys Gly
                340                 345                 350

Lys Ala Ile Ile Ala Met Pro Ser Val Ala Lys Lys Asp Gly Ser
                355                 360                 365

Met Ile Ser Lys Ile Val Pro Phe Ile Asp His Gly Ala Ala Val Thr
370                 375                 380

Thr Ser Arg Asn Asp Ala Asp Tyr Val Val Thr Glu Tyr Gly Ile Ala
385                 390                 395                 400

Glu Met Lys Gly Lys Ser Leu Gln Asp Arg Ala Arg Ala Leu Ile Asn
                405                 410                 415

Ile Ala His Pro Asp Phe Lys Asp Glu Leu Lys Ala Glu Phe Glu Lys
                420                 425                 430

Arg Phe Asn Ala Ala Phe
                435

<210> SEQ ID NO 20
<211> LENGTH: 488
<212> TYPE: PRT
<213> ORGANISM: Citrobacter sp.

<400> SEQUENCE: 20

Met Lys Arg Met Ser Ala Glu Gln Ala Glu Ile Ile Gln His Asp
1               5                   10                  15

Asp Met Val Ala Phe Ser Gly Phe Thr Pro Ala Gly Ser Pro Lys Ala
                20                  25                  30

Leu Pro Thr Ala Ile Ala Gln Arg Ala Cys Glu Gln His Gln Asn Gly
                35                  40                  45

Gln Pro Phe Gln Ile Arg Leu Leu Thr Gly Ala Ser Ile Gly Ala Ala
        50                  55                  60

Ala Asp Asp Val Leu Ser Ala Ala Asp Ala Val Ser Trp Arg Ala Pro
65                  70                  75                  80

Tyr Gln Thr Ser Ser Gly Leu Arg Asp Lys Ile Asn Gln Gly Gln Val
                85                  90                  95

Arg Phe Val Asp Leu His Leu Ser Glu Val Ala Gln Met Val Asn Tyr
                100                 105                 110

Gly Phe Phe Gly Glu Ile Asp Val Ala Val Ile Glu Ala Ser Ala Ile
                115                 120                 125

Ala Pro Asp Gly Arg Ile Trp Leu Ser Ser Gly Ile Gly Asn Ala Pro
        130                 135                 140

Thr Trp Leu Leu Arg Ala Lys Lys Val Ile Glu Leu Asn His Tyr
145                 150                 155                 160

His Asn Pro Arg Val Ala Glu Phe Ala Asp Ile Val Ile Pro Gly Ala
                165                 170                 175

Pro Pro Arg Arg Asn Ser Val Pro Ile Phe His Thr Met Asp Arg Val
                180                 185                 190

Gly Ser Gln Cys Val Gln Ile Asp Pro Lys Lys Val Val Ala Val Val
                195                 200                 205
```

```
Asp Thr Glu Leu Pro Asp Ala Gly Asn Ala Ser Asp Lys Thr Asn Pro
    210                 215                 220

Val Ser Gln Gln Ile Ala Asp Asn Val Val Ser Phe Leu Leu Ala Glu
225                 230                 235                 240

Met Ala His Lys Arg Ile Pro Ala Glu Phe Leu Pro Leu Gln Ser Gly
                245                 250                 255

Val Gly Asn Ile Asn Asn Ala Val Met Ala Arg Leu Gly Glu Asn Pro
            260                 265                 270

Asp Ile Pro Pro Phe Met Met Tyr Ser Glu Val Leu Gln Glu Ser Val
        275                 280                 285

Val His Leu Leu Glu Thr Gly Lys Ile Ser Gly Ala Ser Ala Ser Ser
    290                 295                 300

Leu Thr Ile Ser Ala Pro Ser Leu Gln Lys Ile Tyr Asp Asn Met Asp
305                 310                 315                 320

Phe Phe Ala Ser Arg Ile Val Leu Arg Pro Gln Glu Ile Ser Asn Asn
                325                 330                 335

Pro Glu Ile Ile Arg Arg Leu Gly Val Ile Ala Leu Asn Val Gly Leu
            340                 345                 350

Glu Phe Asp Ile Tyr Gly His Ala Asn Ser Thr His Val Ala Gly Val
        355                 360                 365

Asn Leu Met Asn Gly Ile Gly Gly Ser Gly Asp Phe Glu Arg Asn Ala
    370                 375                 380

Tyr Leu Ser Ile Phe Met Ala Pro Ser Ile Ala Lys Gly Gly Lys Ile
385                 390                 395                 400

Ser Thr Ile Val Pro Met Cys Ser His Val Asp His Ser Glu His Ser
                405                 410                 415

Val Lys Val Ile Val Thr Glu Gln Gly Ile Ala Asp Leu Arg Gly Leu
            420                 425                 430

Ser Pro Met Gln Arg Ala His Thr Ile Ile Asn Asn Cys Ala His Pro
        435                 440                 445

Leu Tyr Arg Asp Tyr Leu His Arg Tyr Leu Glu Lys Ala Pro Gly Gly
    450                 455                 460

His Ile His His Asp Leu Ser His Ala Phe Asp Leu His Arg Asn Leu
465                 470                 475                 480

Leu Glu Thr Gly Ser Met Leu Gly
                485

<210> SEQ ID NO 21
<211> LENGTH: 505
<212> TYPE: PRT
<213> ORGANISM: Acetobacter aceti

<400> SEQUENCE: 21

Met Thr Glu Arg Ile Arg Asn Val Ala Leu Arg Ser Lys Val Cys Pro
1               5                   10                  15

Ala Glu Thr Ala Ser Glu Leu Ile Lys His Gly Asp Val Val Gly Thr
            20                  25                  30

Ser Gly Phe Thr Gly Ala Gly Tyr Pro Lys Glu Val Pro Lys Ala Leu
        35                  40                  45

Ala Gln Arg Met Glu Ala Ala His Asp Arg Gly Glu Lys Tyr Gln Ile
    50                  55                  60

Ser Leu Ile Thr Gly Ala Ser Thr Gly Pro Gln Leu Asp Gly Glu Leu
65                  70                  75                  80

Ala Lys Ala Asn Gly Val Tyr Phe Arg Ser Pro Phe Asn Thr Asp Ala
                85                  90                  95
```

```
Thr Met Arg Asn Arg Ile Asn Ala Gly Glu Thr Glu Tyr Phe Asp Asn
            100                 105                 110

His Leu Gly Gln Val Ala Gly Arg Ala Val Gln Gly Asn Tyr Gly Lys
            115                 120                 125

Phe Asn Ile Ala Leu Val Glu Ala Thr Ala Ile Thr Glu Asp Gly Gly
130                 135                 140

Ile Val Pro Thr Ser Ser Val Gly Asn Ser Gln Thr Phe Leu Asn Leu
145                 150                 155                 160

Ala Glu Lys Val Ile Ile Glu Val Asn Glu Trp Gln Asn Pro Met Leu
                165                 170                 175

Glu Gly Ile His Asp Ile Trp Asp Gly Asn Val Ser Gly Val Pro Thr
            180                 185                 190

Arg Asp Ile Val Pro Ile Val Arg Ala Asp Gln Arg Val Gly Gly Pro
            195                 200                 205

Val Leu Arg Val Asn Pro Asp Lys Ile Ala Ala Ile Val Arg Thr Asn
            210                 215                 220

Asp Arg Asp Arg Asn Ala Pro Phe Ala Ala Pro Asp Glu Thr Ala Lys
225                 230                 235                 240

Ala Ile Ala Gly Tyr Leu Leu Asp Phe Phe Gly His Glu Val Lys Gln
                245                 250                 255

Asn Arg Leu Pro Pro Ser Leu Leu Pro Leu Gln Ser Gly Val Gly Asn
            260                 265                 270

Val Ala Asn Ala Val Leu Glu Gly Leu Lys Glu Gly Pro Phe Glu Asn
            275                 280                 285

Leu Val Gly Tyr Ser Glu Val Ile Gln Asp Gly Met Leu Ala Met Leu
            290                 295                 300

Asp Ser Gly Arg Met Arg Ile Ala Ser Ala Ser Ser Phe Ser Leu Ser
305                 310                 315                 320

Pro Glu Ala Ala Glu Glu Ile Asn Asn Arg Met Asp Phe Phe Arg Ser
                325                 330                 335

Lys Ile Ile Leu Arg Gln Gln Asp Val Ser Asn Ser Pro Gly Ile Ile
            340                 345                 350

Arg Arg Leu Gly Cys Ile Ala Met Asn Gly Met Ile Glu Ala Asp Ile
            355                 360                 365

Tyr Gly Asn Val Asn Ser Thr Arg Val Met Gly Ser Lys Met Met Asn
            370                 375                 380

Gly Ile Gly Gly Ser Gly Asp Phe Ala Arg Ser Ser Tyr Leu Ser Ile
385                 390                 395                 400

Phe Leu Ser Pro Ser Thr Ala Lys Gly Gly Lys Ile Ser Ala Ile Val
                405                 410                 415

Pro Met Ala Ala His Val Asp His Ile Met Gln Asp Ala Gln Ile Phe
            420                 425                 430

Val Thr Glu Gln Gly Leu Ala Asp Leu Arg Gly Leu Ser Pro Val Gln
            435                 440                 445

Arg Ala Arg Glu Ile Ile Ser Lys Cys Ala His Pro Asp Tyr Arg Pro
            450                 455                 460

Met Leu Gln Asp Tyr Phe Asp Arg Ala Leu Lys Asn Ser Phe Gly Lys
465                 470                 475                 480

His Thr Pro His Leu Leu Thr Glu Ala Leu Ser Trp His Gln Arg Phe
                485                 490                 495

Ile Asp Thr Gly Thr Met Leu Pro Ser
            500                 505
```

```
<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic
      7xHis tag

<400> SEQUENCE: 22

His His His His His His His
1               5
```

METHODS AND MATERIALS FOR PRODUCING 7-CARBON MONOMERS

CROSS REFERENCE TO RELATED APPLICATIONS

This application is a continuation of U.S. application Ser. No. 16/262,184, filed on Jan. 30, 2019, which is a continuation of U.S. application Ser. No. 15/368,419, filed Dec. 2, 2016, which claims priority to U.S. Provisional Application No. 62/263,317, filed Dec. 4, 2015, the contents of which are incorporated herein by reference.

TECHNICAL FIELD

This invention provides methods for biosynthesizing 7-carbon monomers. For example, the present invention provides methods for making 5-amino-3-oxopentanoyl-[ACP] or 5-amino-3-oxopentanoyl-CoA or corresponding salts thereof using a β-ketoacyl synthase or a β-ketothiolase and enzymatically converting 5-amino-3-oxopentanoyl-[ACP] or 5-amino-3-oxopentanoyl-CoA or corresponding salts thereof to 7-aminoheptanoic acid using one or more polypeptides having the activity of a 3-oxoacyl-[ACP] reductase, a 3-hydroxyacyl-CoA dehydrogenase, a 3-hydroxyacyl-[ACP] dehydratase, an enoyl-CoA hydratase, an enoyl-[ACP] reductase, a trans-2-enoyl-CoA reductase, a β-ketoacyl synthase, a β-ketothiolase, and a thioesterase or a CoA-transferase, or methods using microorganisms expressing one or more of such enzymes. This invention also provides methods for converting 7-aminoheptanoic acid to one or more of pimelic acid, 7-hydroxyheptanoic acid, heptamethylenediamine and 1,7-heptanediol or their corresponding salts thereof using one or more polypeptides having the activity of isolated enzymes such as dehydrogenases, reductases, N-acetyl transferases, deacylases, thioesterases, and transaminases or using recombinant microorganisms expressing one or more such enzymes.

BACKGROUND

Nylons are synthetic polymers composed of polyamides which are generally synthesized by the condensation polymerization of a diamine with a dicarboxylic acid. Similarly, nylons also may be produced by the condensation polymerization of lactams. Nylon 7 is produced by polymerization of 7-aminoheptanoic acid, whereas Nylon 7,7 is produced by condensation polymerization of pimelic acid and heptamethylenediamine. No economically cost competitive petrochemical route exists to produce the monomers for Nylon 7 and Nylon 7,7.

Given no economically cost competitive petrochemical monomer feedstock, biotechnology offers an alternative approach via biocatalysis. Biocatalysis is the use of biological catalysts, such as enzymes, to perform biochemical transformations of, for example, bioderived feedstocks and petrochemical feedstocks which can both be viable starting materials for the biocatalysis processes.

SUMMARY

Accordingly, against this background, it is clear that there is a need for sustainable methods for producing one or more of 7-aminoheptanoate, pimelic acid, 7-hydroxyheptanoate, heptamethylenediamine, and 1,7-heptanediol wherein the methods are biocatalyst based.

This document is based at least in part on the discovery that it is possible to construct biochemical pathways for using, inter alia, polypeptides having the activity of a β-ketoacyl synthase or a β-ketothiolase to produce 7-aminoheptanoate or a salt thereof which can be converted in one or more enzymatic steps to pimelic acid, 7-hydroxyheptanoic acid, heptamethylenediamine or 1,7-heptanediol. Pimelic acid and pimelate, 7-hydroxyheptanoic acid and 7-hydroxyheptanoate, and 7-aminoheptanoic acid and 7-aminoheptanoate are used interchangeably herein to refer to the compound in any of its neutral or ionized forms, including any salt forms thereof. It is understood by those skilled in the art that the specific form will depend on pH.

For compounds containing carboxylic acid groups such as organic monoacids, hydroxyacids, amino acids and dicarboxylic acids, these compounds may be formed or converted to their ionic salt form when an acidic proton present in the parent compound either is replaced by a metal ion, e.g., an alkali metal ion, an alkaline earth ion, or an aluminum ion; or coordinates with an organic base. Acceptable organic bases include ethanolamine, diethanolamine, triethanolamine, tromethamine, N-methylglucamine, and the like. Acceptable inorganic bases include aluminum hydroxide, calcium hydroxide, potassium hydroxide, sodium carbonate, sodium hydroxide, and the like. The salt can be isolated as is from the system as the salt or converted to the free acid by reducing the pH to below the pKa through addition of acid or treatment with an acidic ion exchange resin.

For compounds containing amine groups such as but not limited to organic amines, amino acids and diamine, these compounds may be formed or converted to their ionic salt form by addition of an acidic proton to the amine to form the ammonium salt, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid or muconic acid. Acceptable inorganic bases are known in the art and include aluminum hydroxide, calcium hydroxide, potassium hydroxide, sodium carbonate, sodium hydroxide, and the like. The salt can be isolated as is from the system as a salt or converted to the free amine by raising the pH to above the pKb through addition of base or treatment with a basic ion exchange resin.

For compounds containing both amine groups and carboxylic acid groups such as but not limited to amino acids, these compounds may be formed or converted to their ionic salt form by either 1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethane-sulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-β-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid Acceptable inorganic bases include aluminum hydroxide, calcium hydroxide, potassium hydroxide, sodium carbonate, sodium hydroxide, and the like or 2) when an acidic proton present in the parent compound either is replaced by a metal ion, e.g., an alkali metal ion, an alkaline earth ion, or an aluminum ion; or coordinates with an organic base. Acceptable organic bases are known in the art and include ethanolamine, diethanolamine, triethanolamine, tromethamine, N-methylglucamine, and the like. Acceptable inorganic bases are known in the art and include aluminum hydroxide, calcium hydroxide, potassium hydroxide, sodium carbonate, sodium hydroxide, and the like. The salt can be isolated as is from the system or converted to the free acid by reducing the pH to below the pKa through addition of acid or treatment with an acidic ion exchange resin.

It has been surprisingly discovered that appropriate non-natural pathways, feedstocks, microorganisms, attenuation strategies to the microorganism's biochemical network and cultivation strategies may be combined to efficiently produce 7-aminoheptanoate as a C7 (7-carbon) building block, or convert 7-aminoheptanoate to other C7 building blocks such as pimelic acid, 7-hydroxyheptanoic acid, heptamethylenediamine or 1,7-heptanediol.

In some embodiments, a terminal carboxyl group can be enzymatically formed using polypeptides having the activity of a thioesterase, a CoA transferase, a ω-transaminase, an aldehyde dehydrogenase, a 5-oxopentanoate dehydrogenase, a 6-oxohexanoate dehydrogenase or a 7-oxoheptanoate dehydrogenase. See FIGS. 3 and 4.

In some embodiments, a terminal amine group can be enzymatically formed using polypeptides having the activity of a carboxylate reductase, a ω-transaminase or a deacylase. See FIGS. 1 and 5. The carboxylate reductase can have at least 70% sequence identity to any one of the amino acid sequences set forth in SEQ ID NOs. 2-6 and 15. Furthermore, the carboxylate reductase can have at least 70% sequence identity to any one of the amino acid sequences set forth in SEQ ID NOs. 2-6 and 15 and be capable of reducing a carboxyl group to a terminal aldehyde. The ω-transaminase can have at least 70% sequence identity to any one of the amino acid sequences set forth in SEQ ID NOs. 7-12. Furthermore, the ω-transaminase can have at least 70% sequence identity to any one of the amino acid sequences set forth in SEQ ID NOs. 7-12 and be capable of transferring at least one amine group separated from a carbonyl group by at least one methylene insertion.

In some embodiments, a terminal hydroxyl group can be enzymatically formed using a polypeptide having the activity of an alcohol dehydrogenase. See FIG. 6 and FIG. 7.

In one aspect, this document features a method of producing 5-amino-3-oxopentanoyl-[ACP] and 5-amino-3-oxopentanoyl-CoA or corresponding salts thereof. The method includes enzymatically converting β-alanyl-[ACP] to 5-amino-3-oxopentanoyl-[ACP] using a polypeptide having the activity of a β-ketoacyl synthase classified under EC. 2.3.1.- (e.g., EC 2.3.1.41, EC 2.3.1.179 or EC 2.3.1.180). The method also includes enzymatically converting β-alanyl-CoA to 5-amino-3-oxopentanoyl-CoA using a polypeptide having the activity of a β-ketoacyl synthase classified under EC. 2.3.1.- (e.g., EC 2.3.1.180) or a polypeptide having the activity of a β-ketothiolase classified under EC. 2.3.1.- (e.g., EC 2.3.1.16 or EC 2.3.1.174). The polypeptide having the activity of a β-ketothiolase can have at least 70% sequence identity to the amino acid sequence set forth in SEQ ID NO:1 or SEQ ID NO:13. Furthermore, the polypeptide having the activity of a β-ketothiolase can have at least 70% sequence identity to the amino acid sequence set forth in SEQ ID NO:1 or SEQ ID NO:13 and be capable of converting β-alanyl-CoA to 5-amino-3-oxopentanoyl-CoA. The polypeptide having the activity of a β-ketoacyl synthase can have at least 70% sequence identity to the amino acid sequence set forth in SEQ ID NO:14. Furthermore, the polypeptide having the activity of a β-ketoacyl synthase can have at least 70% sequence identity to the amino acid sequence set forth in SEQ ID NO: 14 and be capable of converting β-alanyl-[ACP] or β-alanyl-CoA to 5-amino-3-oxopentanoyl-[ACP] or 5-amino-3-oxopentanoyl-CoA respectively.

The method can include enzymatically converting either 5-amino-3-oxopentanoyl-[ACP] or 5-amino-3-oxopentanoyl-CoA or corresponding salts thereof to 7-aminoheptanoate using a plurality of polypeptides having the activities of a 3-oxoacyl-[ACP] reductase or a 3-hydroxyacyl-CoA dehydrogenase respectively, a 3-hydroxyacyl-[ACP] dehydratase or an enoyl-CoA hydratase respectively, an enoyl-[ACP] reductase or a trans-2-enoyl-CoA reductase respectively, a β-ketoacyl synthase or a β-ketothiolase respectively, and a thioesterase or a CoA transferase.

The polypeptides having the activity of a 3-oxoacyl-[ACP] reductase or 3-hydroxyacyl-CoA dehydrogenase can be classified under EC 1.1.1.35, EC 1.1.1.36, EC 1.1.1.100 or EC 1.1.1.157. The polypeptide having the activity of a 3-hydroxyacyl-[ACP] dehydratase can be classified under EC 4.2.1.59. The polypeptide having the activity of an enoyl-CoA hydratase can be classified under EC 4.2.1.17 or EC 4.2.1.119. The polypeptide having the activity of an enoyl-[ACP] reductase can be classified under EC 1.3.1.10 and the polypeptide having the activity of a trans-2-enoyl-CoA reductase can be classified under EC 1.3.1.38, EC 1.3.1.44 or EC 1.3.1.8. The polypeptide having the activity of a β-ketoacyl synthase can be classified under EC 2.3.1.41, EC 2.3.1.179 or EC 2.3.1.180. The polypeptide having the activity of a β-ketothiolase can be classified under EC 2.3.1.16 or EC 2.3.1.174. The polypeptides having the activity of a thioesterase or CoA transferase can be classified under EC 3.1.2.- or EC 2.8.3.- respectively.

In one aspect, this document features a method for biosynthesizing 7-aminoheptanoate or the salt thereof. The method includes enzymatically converting β-alanyl-[ACP] to 5-amino-3-oxopentanoyl-[ACP] using a polypeptide having the activity of a β-ketoacyl synthase classified under EC. 2.3.1.- (e.g., EC 2.3.1.41, EC 2.3.1.179 or EC 2.3.1.180). The method also includes enzymatically converting β-alanyl-CoA to 5-amino-3-oxopentanoyl-CoA using a polypeptide having the activity of a β-ketoacyl synthase classified under EC. 2.3.1.- (e.g., EC 2.3.1.180) or a β-ketothiolase classified under EC. 2.3.1.- (e.g., EC 2.3.1.16 or EC 2.3.1.174). The β-ketothiolase can have at least 70% sequence identity to the amino acid sequence set forth in SEQ ID NO:1 or SEQ ID NO:13. The polypeptide having the activity of a β-ketothiolase can have at least 70% sequence identity to the amino acid sequence set forth in SEQ ID NO:1 or SEQ ID NO:13 and be capable of converting β-alanyl-CoA to 5-amino-3-oxopentanoyl-CoA. The β-ketoacyl synthase can have at least 70% sequence identity to the amino acid sequence set forth in SEQ ID NO:14.

Furthermore, the polypeptide having the activity of a β-ketoacyl synthase can have at least 70% sequence identity to the amino acid sequence set forth in SEQ ID NO: 14 and be capable of converting β-alanyl-[ACP] or β-alanyl-CoA to 5-amino-3-oxopentanoyl-[ACP] or 5-amino-3-oxopentanoyl-CoA respectively.

5-amino-3-oxopentanoyl-[ACP] or a salt thereof can be converted to 5-amino-3-hydroxypentanoyl-[ACP] using a polypeptide having the activity of a 3-oxoacyl-[ACP] reductase and 5-amino-3-oxopentanoyl-CoA can be converted to 5-amino-3-hydroxypentanoyl-CoA using a polypeptide having the activity of a 3-hydroxyacyl-CoA dehydrogenase. 5-amino-3-hydroxypentanoyl-[ACP] can be converted to 5-amino-pent-2-enoyl-[ACP] using a polypeptide having the activity of a 3-hydroxyacyl-[ACP] dehydratase and 5-amino-3-hydroxypentanoyl-CoA can be converted to 5-amino-pent-2-enoyl-CoA using a polypeptide having the activity of an enoyl-CoA hydratase. 5-amino-pent-2-enoyl-[ACP] can be converted to 5-amino-pentanoyl-[ACP] using a polypeptide having the activity of an enoyl-[ACP] reductase and 5-amino-pent-2-enoyl-CoA can be converted to 5-amino-pentanoyl-CoA using a polypeptide having the activity of a trans-2-enoyl-CoA reductase. 5-amino-pentanoyl-[ACP] can be converted to 7-amino-3-oxoheptanoyl-[ACP] using a polypeptide having the activity of a β-ketoacyl synthase and 5-amino-pentanoyl-CoA can be converted to 7-amino-3-oxoheptanoyl-CoA using a polypeptide having the activity of a β-ketothiolase. 7-amino-3-oxoheptanoyl-[ACP] can be converted to 7-amino-3-hydroxyheptanoyl-[ACP] using a polypeptide having the activity of a 3-oxoacyl-[ACP] reductase and 7-amino-3-oxoheptanoyl-CoA can be converted to 7-amino-3-hydroxyheptanoyl-CoA using a polypeptide having the activity of a 3-hydroxyacyl-CoA dehydrogenase. 7-amino-3-hydroxyheptanoyl-[ACP] can be converted to 7-amino-hept-2-enoyl-[ACP] using a polypeptide having the activity of a 3-hydroxyacyl-[ACP] dehydratase and 7-amino-3-hydroxyheptanoyl-CoA can be converted to 7-amino-hept-2-enoyl-CoA using a polypeptide having the activity of an enoyl-CoA hydratase. 7-amino-hept-2-enoyl-[ACP] can be converted to 7-aminoheptanoyl-[ACP] using a polypeptide having the activity of an enoyl-[ACP] reductase and 7-amino-hept-2-enoyl-CoA can be converted to 7-aminoheptanoyl-CoA using a polypeptide having the activity of a trans-2-enoyl-CoA reductase. 7-aminoheptanoyl-[ACP] can be converted to 7-aminoheptanoate using a polypeptide having the activity of a thioesterase. 7-aminoheptanoyl-CoA can be converted to 7-aminoheptanoate using a polypeptide having the activity of a thioesterase or a CoA transferase.

Any of the methods further can include enzymatically converting 7-aminoheptanoate to pimelic acid, 7-hydroxyheptanoate, heptamethylenediamine or 1,7-heptanediol or corresponding salts thereof in one or more steps.

For example, 7-aminoheptanoate can be enzymatically converted to pimelic acid using one or more polypeptides having the activity of a ω-transaminase, a 7-oxoheptanoate dehydrogenase, a 6-oxohexanoate dehydrogenase, a 5-oxopentanoate dehydrogenase or an aldehyde dehydrogenase. See FIG. 4.

For example, 7-aminoheptanoate can be converted to 7-hydroxyheptanoate using one or more polypeptides having the activity of an alcohol dehydrogenase, a 6-hydroxyhexanoate dehydrogenase, a 5-hydroxypentanoate dehydrogenase, a 4-hydroxybutanoate dehydrogenase, and a ω-transaminase. See FIG. 6. The ω-transaminase can have at least 70% sequence identity to any one of the amino acid sequences set forth in SEQ ID NO. 7-12. Furthermore, the ω-transaminase can have at least 70% sequence identity to any one of the amino acid sequences set forth in SEQ ID NO. 7-12 and be capable of transferring at least one amine group separated from a carboxyl group by at least one methylene insertion.

For example, 7-aminoheptanoate and 7-hydroxyheptanoate can be converted to heptamethylenediamine using one or more polypeptides having the activity of a carboxylate reductase, a ω-transaminase, an alcohol dehydrogenase, an N-acetyltransferase, and a deacylase. The carboxylate reductase can have at least 70% sequence identity to any one of the amino acid sequences set forth in SEQ ID NO. 2-6 and 15. See FIG. 8A, FIG. 8B, FIG. 8C, and FIG. 8D. Furthermore, the carboxylate reductase can have at least 70% sequence identity to any one of the amino acid sequences set forth in SEQ ID NO. 2-6 and 15 and be capable of reducing a carboxyl group to a terminal aldehyde. The ω-transaminase can have at least 70% sequence identity to any one of the amino acid sequences set forth in SEQ ID NO. 7-12. See FIG. 8C and FIG. 8D. Furthermore, the ω-transaminase can have at least 70% sequence identity to any one of the amino acid sequences set forth in SEQ ID NO. 7-12 and be capable of transferring at least one amine group separated from a carbonyl group by at least one methylene insertion.

For example, 7-aminoheptanoate can be converted to 7-hydroxyheptanoate (see FIG. 6) and subsequently 7-hydroxyheptanoate can be converted to 1,7-heptanediol using one ore more polypeptides having the activity of a carboxylate reductase and an alcohol dehydrogenase. See FIG. 7. The carboxylate reductase can have at least 70% sequence identity to any one of the amino acid sequences set forth in SEQ ID NO. 2-6 and 15. See FIG. 8A, FIG. 8B, FIG. 8C, and FIG. 8D. Furthermore, the carboxylate reductase can have at least 70% sequence identity to any one of the amino acid sequences set forth in SEQ ID NO. 2-6 and 15 and be capable of reducing a carboxyl group to a terminal aldehyde.

In any of the methods, β-alanyl-[ACP] and β-alanyl-CoA can be enzymatically produced from β-alanine, which itself can be enzymatically produced from malonyl-CoA using polypeptides having the activity of a malonyl-CoA-reductase and a β-alanine-pyruvate aminotransferase or from L-aspartate using a polypeptide having the activity of an aspartate α-decarboxylase.

In any of the methods described herein, pimelic acid can be produced by forming the second terminal functional group in pimelate semialdehyde (also known as 7-oxoheptanoate) using a polypeptide having the activity of (i) an aldehyde dehydrogenase classified under EC 1.2.1.3, or (ii) a 5-oxopentanoate dehydrogenase classified under EC 1.2.1.- such as encoded by CpnE, a 6-oxohexanoate dehydrogenase classified under EC 1.2.1.63 such as that encoded by ChnE or a 7-oxoheptanoate dehydrogenase classified under EC 1.2.1.- (e.g., the gene product of ThnG).

In any of the methods described herein, 7-hydroxyheptanoic acid can be produced by forming the second terminal functional group in pimelate semialdehyde using a polypeptide having the activity of an alcohol dehydrogenase classified under EC 1.1.1.-, a 6-hydroxyhexanoate dehydrogenase classified under EC 1.1.1.258 such as the gene product of ChnD (Iwaki et al., *Appl. Environ. Microbiol.*, 1999, 65(11):5158-5162); a 5-hydroxypentanoate dehydrogenase classified under EC 1.1.1.- such as the gene product of cpnD, or a 4-hydroxybutanoate dehydrogenase classified under EC 1.1.1.61 such as the gene product of gabD. See FIG. 6.

In any of the methods described herein, heptamethylenediamine can be produced by forming a second terminal functional group in (i) 7-aminoheptanal using a polypeptide having the activity of a ω-transaminase classified under EC 2.6.1.18, EC 2.6.1.19, EC 2.6.1.29, EC 2.6.1.48 or EC 2.6.1.82 or in (ii) N7-acetyl-1,7-diaminoheptane using a polypeptide having the activity of a deacylase classified, for example, under EC 3.5.1.62. See FIG. 5A and FIG. 5C.

In any of the methods described herein, 1,7-heptanediol can be produced by forming the second terminal functional group in 7-hydroxyheptanal using a polypeptide having the activity of an alcohol dehydrogenase classified under EC 1.1.1.- (e.g., EC 1.1.1.1, 1.1.1.2, 1.1.1.21, or 1.1.1.184) such as that encoded by YMR318C, YqhD or CAA81612.1. See FIG. 7.

In some embodiments, the biological feedstock can be or can derive from, monosaccharides, disaccharides, lignocellulose, hemicellulose, cellulose, lignin, levulinic acid and formic acid, triglycerides, glycerol, fatty acids, agricultural waste, condensed distillers' solubles, or municipal waste.

In some embodiments, the non-biological feedstock can be or can derive from natural gas, syngas, $CO_2/H_2$, methanol, ethanol, benzoate, non-volatile residue (NVR) or a caustic wash waste stream from cycloheptane oxidation processes, or terephthalic acid/isophthalic acid mixture waste streams.

In some embodiments, the microorganism's tolerance to high concentrations of one or more C7 (7-carbon) building blocks is improved through continuous cultivation in a selective environment.

In some embodiments, the microorganism's biochemical network is attenuated or augmented to (1) ensure the intracellular availability of acetyl-CoA and β-alanine, (2) create an NADH or NADPH imbalance that may only be balanced via the formation of one or more C7 building blocks, (3) prevent degradation of central metabolites, central precursors leading to and including C7 building blocks and (4) ensure efficient efflux from the cell.

In some embodiments, a cultivation strategy is used to achieve anaerobic, micro-aerobic, or aerobic cultivation conditions.

In some embodiments, the cultivation strategy includes limiting nutrients, such as limiting nitrogen, phosphate or oxygen.

In some embodiments, one or more C7 building blocks are produced by a single type of microorganism, e.g., a recombinant microorganism containing one or more exogenous nucleic acids, using, for example, a fermentation strategy. In some embodiments, one or more C7 building blocks are produced by a single type of microorganism having one or more exogenous nucleic acids which encode a polypeptide having an activity of a 3-hydroxyacyl-CoA dehydrogenase, a 3-oxoacyl-[ACP]-reductase, an enoyl-CoA hydratase, a 3-hydroxyacyl-[ACP]-dehydratase, a trans-2-enoyl-CoA reductase, an enoyl-[ACP]-reductase, a β-ketoacyl synthase, a 3-ketothiolase, and a thioesterase or a CoA transferase.

In another aspect, this document features a recombinant microorganism that includes at least one exogenous nucleic acid encoding a polypeptide having the activity of (i) a β-ketoacyl synthase, (ii) a β-ketothiolase, (iii) a thioesterase or a CoA transferase, and one or more of (iv) a 3-oxoacyl-[ACP] reductase or a 3-hydroxyacyl-CoA dehydrogenase, (v) a 3-hydroxyacyl-[ACP] dehydratase or an enoyl-CoA hydratase, and (vi) an enoyl-[ACP] reductase or a trans-2-enoyl-CoA reductase, the microorganism producing 7-aminoheptanoate. See FIG. 1, FIG. 2 and FIG. 3.

A microorganism producing 7-aminoheptanoate further can include one or more of the following exogenous polypeptides having the activity of: a ω-transaminase, a 7-oxoheptanoate dehydrogenase, a 6-oxohexanoate dehydrogenase, a 5-oxopentanoate dehydrogenase, or an aldehyde dehydrogenase, the microorganism further producing pimelic acid. See FIG. 4.

A microorganism producing 7-aminoheptanoate further can include one or more of the following exogenous polypeptides having the activity of: a ω-transaminase, a 6-hydroxyhexanoate dehydrogenase, a 4-hydroxybutanoate dehydrogenase, a 5-hydroxypentanoate dehydrogenase, and an alcohol dehydrogenase, the microorganism further producing 7-hydroxyheptanoate. See FIG. 6.

A microorganism producing 7-aminoheptanoate or 7-hydroxyheptanoate further can include one or more of the following exogenous polypeptides having the activity of: a carboxylate reductase, a ω-transaminase, a deacylase, an N-acetyl transferase, or an alcohol dehydrogenase, said microorganism further producing heptamethylenediamine. See FIG. 5A-C.

A microorganism producing 7-hydroxyheptanoate further can include an exogenous polypeptide having the activity of a carboxylate reductase and an exogenous polypeptide having the activity of an alcohol dehydrogenase, the microorganism further producing 1,7-heptanediol. See FIG. 7.

Any of the recombinant microorganisms described herein further can include one or more of the following exogenous polypeptides having the activity of: an aspartate-α-decarboxylase; a malonyl-CoA reductase; a β-alanine-pyruvate aminotransferase; a CoA-transferase; and an [ACP]-acetyltransferase.

Any of the recombinant microorganisms can be a prokaryote such as a prokaryote from a genus selected from the group consisting of *Escherichia; Clostridia; Corynebacteria; Cupriavidus; Pseudomonas; Delftia; Bacilluss; Lactobacillus; Lactococcus*; and *Rhodococcus*. For example, the prokaryote can be selected from the group consisting of *Escherichia coli, Clostridium ljungdahlii, Clostridium autoethanogenum, Clostridium kluyveri, Corynebacterium glutamicum, Cupriavidus necator, Cupriavidus metallidurans. Pseudomonas fluorescens, Pseudomonas putida, Pseudomonas oleavorans, Delftia acidovorans, Bacillus subtillis, Lactobacillus delbrueckii, Lactococcus lactis*, and *Rhodococcus equi*. Such prokaryotes also can be sources of genes for constructing recombinant cells described herein that are capable of producing C7 building blocks.

Any of the recombinant microorganisms can be a eukaryote such as a eukaryote from a genus selected from the group consisting of *Aspergillus, Saccharomyces, Pichia, Yarrowia, Issatchenkia, Debaryomyces, Arxula*, and *Kluyveromyces*. For example, the eukaryote can be selected from the group consisting of *Aspergillus niger, Saccharomyces cerevisiae, Pichia pastoris, Yarrowia lipolytica, Issathenkia orientalis, Debaryomyces hansenii, Arxula adenoinivorans*, and *Kluyveromyces lactis*. Such eukaryotes also can be sources of genes for constructing recombinant microorganisms described herein that are capable of producing C7 building blocks.

Any of the recombinant microorganisms described herein further can include attenuation of one or more of the following enzymes: a polyhydroxyalkanoate synthase, an acetyl-CoA thioesterase, a phosphotransacetylase forming acetate, an acetate kinase, a lactate dehydrogenase, a menaquinol-fumarate oxidoreductase, an alcohol dehydrogenase forming ethanol, a triose phosphate isomerase, a pyruvate decarboxylase, a glucose-6-phosphate isomerase, NADH-consuming transhydrogenase, an NADH-specific glutamate dehydrogenase, a NADH/NADPH-utilizing glutamate dehydrogenase, a pimeloyl-CoA dehydrogenase; an acyl-CoA dehydrogenase accepting C7 building blocks and central precursors as substrates; a butyryl-CoA dehydrogenase; or an adipyl-CoA synthetase.

Any of the recombinant microorganisms described herein further can overexpress one or more genes encoding: an acetyl-CoA synthetase, a 6-phosphogluconate dehydrogenase; a transketolase; a puridine nucleotide transhydrogenase; a glyceraldehyde-3P-dehydrogenase; a malic enzyme; a glucose-6-phosphate dehydrogenase; a glucose dehydrogenase; a fructose 1,6 diphosphatase; a L-alanine dehydrogenase; a L-glutamate dehydrogenase; a formate dehydrogenase; a L-glutamine synthetase; a diamine transporter; a dicarboxylate transporter; and/or a multidrug transporter.

In another aspect of the invention, this document features a non-naturally occurring microorganism comprising at least one exogenous nucleic acid encoding at least one polypeptide having the activity of at least one enzyme, at least one substrate and at least one product, depicted in any one of FIGS. 1 to 7.

In another aspect of the invention, this document features a plurality of nucleic acid constructs or expression vectors comprising a polynucleotide encoding a polypeptide having enzymatic activities corresponding to the polypeptides as set out in SEQ ID NO:1 to SEQ ID NO: 15 and to polypeptides having at least 70% sequence identity to the polypeptides as set out in SEQ ID NO:1 to SEQ ID NO: 15. (See FIG. 8A, FIG. 8B, FIG. 8C, and FIG. 8D).

In another aspect of the invention, this document features a composition comprising a nucleic acid construct or expression vector comprising a polynucleotide encoding a polypeptide having enzymatic activities corresponding to the polypeptides as set out in SEQ ID NO:1 to SEQ ID NO: 15 and to polypeptides having at least 70% sequence identity to the polypeptides as set out in SEQ ID NO:1 to SEQ ID NO: 15. (See FIG. 8A, FIG. 8B, FIG. 8C, and FIG. 8D).

In another aspect of the invention, this document features a culture medium comprising a nucleic acid construct or expression vector comprising a polynucleotide encoding a polypeptide having enzymatic activities corresponding to the polypeptides as set out in SEQ ID NO:1 to SEQ ID NO: 15 and to polypeptides having at least 70% sequence identity to the polypeptides as set out in SEQ ID NO:1 to SEQ ID NO: 15. (See FIG. 8A, FIG. 8B, FIG. 8C, and FIG. 8D).

In another aspect of the invention, this document features a non-naturally occurring biochemical network comprising β-alanyl-[ACP] or β-alanyl-CoA, an exogenous nucleic acid encoding a polypeptide having the activity of a β-ketothiolase or a β-ketoacyl synthase classified under EC. 2.3.1, and a 5-amino-3-oxopentanoyl-[ACP] or 5-amino-3-oxopentanoyl-CoA respectively.

In another aspect of the invention, this document features a non-naturally occurring biochemical network comprising at least one exogenous nucleic acid encoding a polypeptide having the enzymatic activity of (i) a β-ketoacyl synthase and/or a β-ketothiolase, (ii) a thioesterase or a CoA transferase, and one or more of (iii) a 3-hydroxyacyl-CoA dehydrogenase or a 3-oxoacyl-[ACP] reductase, (iv) an enoyl-CoA hydratase or 3-hydroxyacyl-[ACP] dehydratase, and (v) a trans-2-enoyl-CoA reductase or enoyl-[ACP] reductase, said microorganism producing 7-aminoheptanoate.

In another aspect of the invention, this document features means for producing 7-aminoheptanoate, comprising culturing a non-naturally occurring microorganism comprising at least one exogenous nucleic acid encoding a polypeptide having the enzymatic activity of (i) a β-ketoacyl synthase and/or a β-ketothiolase, (ii) a thioesterase or a CoA transferase, and one or more of (iii) a 3-hydroxyacyl-CoA dehydrogenase or 3-oxoacyl-[ACP]-reductase, (iv) an enoyl-CoA hydratase or a 3-hydroxyacyl-[ACP] dehydratase, and (v) a trans-2-enoyl-CoA reductase or an enoyl-[ACP] reductase, expressed in a sufficient amount in said microorganism to produce 7-amino-heptanoate.

In another aspect of the invention, this document features a bio-derived, bio-based or fermentation-derived product according to any of claims 15 to 25, wherein said product comprises: i. a composition comprising at least one bio-derived, bio-based or fermentation-derived compound according this specification or any combination thereof; ii. a bio-derived, bio-based or fermentation-derived polymer comprising the bio-derived, bio-based or fermentation-derived composition or compound of i., or any combination thereof; iii. a bio-derived, bio-based or fermentation-derived resin comprising the bio-derived, bio-based or fermentation-derived compound or bio-derived, bio-based or fermentation-derived composition of i. or any combination thereof or the bio-derived, bio-based or fermentation-derived polymer of ii. or any combination thereof; iv. a molded substance obtained by molding the bio-derived, bio-based or fermentation-derived polymer of ii. or the bio-derived, bio-based or fermentation-derived resin of iii., or any combination thereof; v. a bio-derived, bio-based or fermentation-derived formulation comprising the bio-derived, bio-based or fermentation-derived composition of i., bio-derived, bio-based or fermentation-derived compound of i., bio-derived, bio-based or fermentation-derived polymer of ii., bio-derived, bio-based or fermentation-derived resin of iii., or bio-derived, bio-based or fermentation-derived molded substance of iv, or any combination thereof, or vi. a bio-derived, bio-based or fermentation-derived semi-solid or a non-semi-solid stream, comprising the bio-derived, bio-based or fermentation-derived composition of i., bio-derived, bio-based or fermentation-derived compound of i., bio-derived, bio-based or fermentation-derived polymer of ii., bio-derived, bio-based or fermentation-derived resin of iii., bio-derived, bio-based or fermentation-derived formulation of v., or bio-derived, bio-based or fermentation-derived molded substance of iv., or any combination thereof.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the application, including the written description and drawings, and the claims. The word "comprising" in the claims may be replaced by "consisting essentially of" or with "consisting of," according to standard practice in patent law.

DESCRIPTION OF DRAWINGS

FIG. 6 is a schematic of exemplary biochemical pathways leading to 7-hydroxyheptanoate using 7-aminoheptanoate as a central precursor.

FIG. 8A contains the amino acid sequences of a *Cupriavidus necator* β-ketothiolase (see GenBank Accession No. AAC38322.1, SEQ ID NO: 1), a *Mycobacterium marinum* carboxylate reductase (see Genbank Accession No. ACC40567.1, SEQ ID NO: 2), and a *Mycobacterium smegmatis* carboxylate reductase (see Genbank Accession No. ABK71854.1, SEQ ID NO: 3). FIG. 8B contains the amino acid sequences of a *Segniliparus rugosus* carboxylate reductase (see Genbank Accession No. EFV11917.1, SEQ ID NO: 4), and a *Mycobacterium massiliense* carboxylate reductase (see Genbank Accession No. EIV11143.1, SEQ ID NO: 5). FIG. 8C contains the amino acid sequences of a *Segniliparus rotundus* carboxylate reductase (see Genbank Accession No. ADG98140.1, SEQ ID NO: 6), a *Chromobacterium violaceum* ω-transaminase (see Genbank Accession No. AAQ59697.1, SEQ ID NO: 7), a *Pseudomonas aeruginosa* ω-transaminase (see Genbank Accession No. AAG08191.1, SEQ ID NO: 8), a *Pseudomonas syringae* ω-transaminase (see Genbank Accession No. AAY39893.1, SEQ ID NO: 9), and a *Rhodobacter sphaeroides* ω-transaminase (see Genbank Accession No. ABA81135.1, SEQ ID NO: 10). FIG. 8D contains the amino acid sequences of an *Escherichia coli* ω-transaminase (see Genbank Accession No. AAA57874.1, SEQ ID NO: 11), a *Vibrio fluvialis* ω-transaminase (See Genbank Accession No. AEA39183.1, SEQ ID NO: 12), an *Escherichia coli* β-ketothiolase (see GenBank Accession No. AAC74479.1, SEQ ID NO: 13), a *Bacillus subtilis* β-ketoacyl synthase encoded by FabHB (see GenBank Accession No. CAA74523.1, SEQ ID NO: 14), and a *Mycobacterium smegmatis* carboxylate reductase (see Genbank Accession No. ABK75684.1, SEQ ID NO: 15). FIG. 8E contains the amino acid sequences of a *Cupriavidus necator* beta-ketothiolase (see GenBank Accession No. AAC38322.1, SEQ ID NO: 16), an *Escherichia coli* (see Genbank Accession No. AAC74479.1, SEQ ID NO: 17), a *Clostridium propionicum* acetate/propionate CoA transferase (see Genbank Accession No. CAB77207.1, SEQ ID NO: 18), a *Clostridium aminobutyricum* 4-hydroxybutyrate-CoA transferase (see Genbank Accession No. CAB60036.2, SEQ ID NO: 19), a *Citrobacter* sp. A1 acetyl-CoA hydrolase/transferase transferase (see Genbank Accession No. EJF23789.1, SEQ ID NO: 20), and an *Acetobacter aceti* succinyl-CoA: acetate CoA-transferase (see Genbank Accesssion No. ACD85596.1, SEQ ID NO: 21).

DETAILED DESCRIPTION

Figure 1:
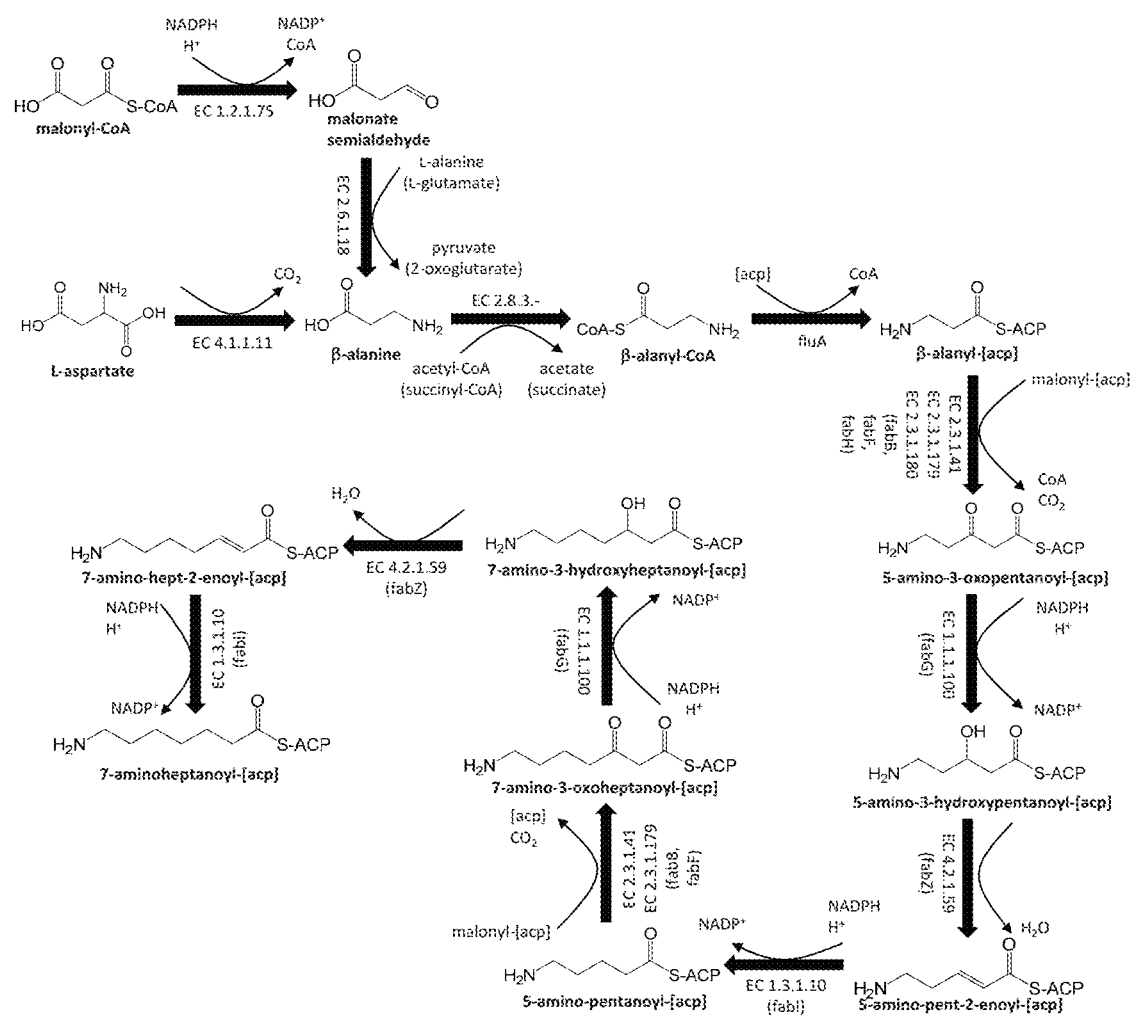
FIG. 1 is a schematic of exemplary biochemical pathways leading to 7-aminoheptanoyl-[ACP] using malonyl-CoA and L-aspartate as central metabolites.

In general, this document provides enzymes, non-natural pathways, cultivation strategies, feedstocks, microorganisms and attenuations to the microorganism's biochemical network, for producing 7-aminoheptanoate or one or more of pimelic acid, 7-hydroxyheptanoic acid, heptamethylenediamine or 1,7-heptanediol or their corresponding salts thereof, all of which are referred to as C7 building blocks herein. The term "C7 building block" is used to denote a seven (7) carbon chain aliphatic backbone. As used herein, the term "central precursor" is used to denote any metabolite in any metabolic pathway shown herein leading to the synthesis of a C7 building block. The term "central metabolite" is used herein to denote a metabolite that is produced in all microorganisms to support growth.

Microorganisms described herein can include endogenous pathways that can be manipulated such that 7-aminoheptanoate or one or more other C7 building blocks can be produced. In an endogenous pathway, the microorganism naturally expresses all of the enzymes catalyzing the reactions within the pathway. A microorganism containing an engineered pathway does not naturally express all of the enzymes catalyzing the reactions within the pathway but has been engineered such that all of the enzymes within the pathway are expressed in the microorganism.

The term "exogenous" as used herein with reference to a nucleic acid (or a protein) and a microorganism refers to a nucleic acid that does not occur in (and cannot be obtained from) a cell of that particular type as it is found in nature or a protein encoded by such a nucleic acid. Thus, a non-naturally-occurring nucleic acid is considered to be exogenous to a microorganism once in the microorganism. It is important to note that non-naturally-occurring nucleic acids can contain nucleic acid subsequences or fragments of nucleic acid sequences that are found in nature provided the nucleic acid as a whole does not exist in nature. For example, a nucleic acid molecule containing a genomic DNA sequence within an expression vector is non-naturally-occurring nucleic acid, and thus is exogenous to a cell once introduced into the microorganism, since that nucleic acid molecule as a whole (genomic DNA plus vector DNA) does not exist in nature. Thus, any vector, autonomously replicating plasmid, or virus (e.g., retrovirus, adenovirus, or herpes virus) that as a whole does not exist in nature is considered to be non-naturally-occurring nucleic acid. It follows that genomic DNA fragments produced by PCR or restriction endonuclease treatment as well as cDNAs are considered to be non-naturally-occurring nucleic acid since they exist as separate molecules not found in nature. It also follows that any nucleic acid containing a promoter sequence and polypeptide-encoding sequence (e.g., cDNA or genomic DNA) in an arrangement not found in nature is non-naturally-occurring nucleic acid. A nucleic acid that is naturally-occurring can be exogenous to a particular microorganism. For example, an entire chromosome isolated from a cell of yeast x is an exogenous nucleic acid with respect to a cell of yeasty once that chromosome is introduced into a cell of yeasty.

In contrast, the term "endogenous" as used herein with reference to a nucleic acid (e.g., a gene) (or a protein) and a microorganism refers to a nucleic acid (or protein) that does occur in (and can be obtained from) that particular microorganism as it is found in nature. Moreover, a cell "endogenously expressing" a nucleic acid (or protein) expresses that nucleic acid (or protein) as does a microorganism of the same particular type as it is found in nature. Moreover, a microorganism "endogenously producing" or that "endogenously produces" a nucleic acid, protein, or other compound produces that nucleic acid, protein, or compound as does a microorganism of the same particular type as it is found in nature.

For example, depending on the microorganism and the compounds produced by the microorganism, one or more of the following polypeptides having the following specific enzymatic activities may be expressed in the microorganism in addition to a β-ketoacyl synthase and/or a β-ketothiolase: a 3-oxoacyl-[ACP] reductase, a 3-hydroxyacyl-CoA dehydrogenase, a 3-hydroxyacyl-[ACP] dehydratase, an enoyl-CoA hydratase, an enoyl-[ACP] reductase, a trans-2-enoyl-CoA reductase, a thioesterase, a CoA transferase, an aldehyde dehydrogenase, an alcohol dehydrogenase, a 7-oxoheptanoate dehydrogenase, a 6-oxohexanoate dehydrogenase, 5-oxopentanoate dehydrogenase, a ω-transaminase, a 6-hydroxyhexanoate dehydrogenase, a 4-hydroxybutanoate dehydrogenase, a 5-hydroxypentanoate dehydrogenase, a carboxylate reductase, an N-acetyl transferase or a deacylase. In recombinant microorganisms expressing a polypeptide having the activity of a carboxylate reductase, a phosphopantetheinyl transferase also can be expressed as it enhances activity of the carboxylate reductase.

For example, a recombinant microorganism can include an exogenous polypeptide having the activity of a β-ketoacyl synthase and produce 5-amino-3-oxopentanoyl-[ACP] or a salt thereof from β-alanyl-[ACP]. The 5-amino-3-oxopentanoyl-[ACP] or salt thereof can be converted enzymatically to 7-aminoheptanoyl-[ACP] and subsequently to 7-aminoheptanoate or the corresponding salt thereof.

For example, a recombinant microorganism can include an exogenous polypeptide having the activity of a β-ketoacyl synthase or a β-ketothiolase and produce 5-amino-3-oxopentanoyl-CoA or a salt thereof from β-alanyl-CoA. The 5-amino-3-oxopentanoyl-CoA or a salt thereof can be converted enzymatically to 7-aminoheptanoyl-CoA and subsequently to 7-aminoheptanoate or the corresponding salt thereof.

For example, a recombinant microorganism producing β-alanine can include exogenous polypeptides having the activity of a β-ketoacyl synthase and an exogenous thioesterase or CoA-transferase, and one or more of the following exogenous enzymes: a 3-oxoacyl-[ACP] reductase, a 3-hydroxyacyl-[ACP] dehydratase and an enoyl-[ACP]

reductase, and produce 7-aminoheptanoate. For example, a recombinant microorganism can include a polypeptide having the activity of an exogenous β-ketothiolase or a β-ketoacyl synthase and a β-ketothiolase, an exogenous thioesterase or CoA-transferase, a 3-hydroxyacyl-CoA dehydrogenase, an enoyl-CoA hydratase, and a trans-2-enoyl-CoA reductase and produce 7-aminoheptanoate or the corresponding salt thereof.

For example, a recombinant microorganism producing 7-aminoheptanoate can include one or more of the following exogenous polypeptides having the enzymatic activity of: a ω-transaminase, a 7-oxoheptanoate dehydrogenase, a 5-oxopentanoate dehydrogenase, a 6-oxohexanoate dehydrogenase, or an aldehyde dehydrogenase, and further produce pimelic acid For example, a recombinant microorganism producing 7-aminoheptanoate can include an exogenous polypeptide having the activity of a ω-transaminase and an aldehyde dehydrogenase and produce pimelic acid. For example, a recombinant microorganism producing 7-aminoheptanoate can include an exogenous polypeptide having the activity of a ω-transaminase and one of the following exogenous polypeptides having the activity of: a 5-oxopentanoate dehydrogenase, a 6-oxohexanoate dehydrogenase, or a 7-oxoheptanoate dehydrogenase, and produce pimelic acid or the corresponding salt thereof.

For example, a recombinant microorganism producing 7-aminoheptanoate can include one or more of the following exogenous polypeptides having the activity of: an alcohol dehydrogenase and a ω-transaminase, and further produce 7-hydroxyheptanoate. For example, a recombinant microorganism producing 7-aminoheptanoate can include an exogenous polypeptide having the activity of an alcohol dehydrogenase and an exogenous ω-transaminase and produce 7-hydroxyheptanoate. For example, a recombinant microorganism producing 7-aminoheptanoate can include an exogenous polypeptide having the activity of a 6-hydroxyhexanoate dehydrogenase and an exogenous polypeptide having the activity of a ω-transaminase and produce 7-hydroxyheptanoate. For example, a recombinant microorganism producing 7-aminoheptanoate can include an exogenous polypeptide having the activity of a 5-hydroxypentanoate dehydrogenase and an exogenous polypeptide having the activity of a ω-transaminase and produce 7-hydroxyheptanoate. For example, a recombinant microorganism producing 7-aminoheptanoate can include an exogenous polypeptide having the activity of a 4-hydroxybutanoate dehydrogenase and an exogenous polypeptide having the activity of a ω-transaminase and produce 7-hydroxyheptanoate or the corresponding salt thereof.

For example, a recombinant microorganism producing 7-aminoheptanoate can include one or more of the following exogenous polypeptides having the enzymatic activity of: a carboxylate reductase, a ω-transaminase, a deacylase, an N-acetyl transferase, or an alcohol dehydrogenase, and produce heptamethylenediamine. For example, a recombinant microorganism producing 7-aminoheptanoate can include exogenous polypeptides having the activity of an exogenous carboxylate reductase and one or more transaminases (e.g., one ω-transaminase or two different transaminases) and produce heptamethylenediamine. For example, a recombinant microorganism producing 7-aminoheptanoate can include exogenous polypeptides having the activity of a carboxylate reductase, an alcohol dehydrogenase, and one or more transaminases (e.g., one ω-transaminase or two different transaminases), and produce heptamethylenediamine. For example, a recombinant microorganism producing 7-aminoheptanoate can include exogenous polypeptides having the activity of an N-acetyl transferase, a carboxylate reductase, a deacylase, and one or more exogenous transaminases (e.g., one ω-transaminase or two different transaminases) and produce heptamethylenediamine. For example, a recombinant microorganism producing 7-aminoheptanoate can include exogenous polypeptides having the activity of an alcohol dehydrogenase and one or more transaminases (e.g., one ω-transaminase, or two or three different transaminases) and produce heptamethylenediamine or the corresponding salt thereof.

For example, a recombinant microorganism producing 7-hydroxyheptanoate can include the following exogenous polypeptides having the activity of: a carboxylate reductase and an alcohol dehydrogenase, and further produce 1,7-heptanediol or the corresponding salt thereof.

In any of the recombinant microorganisms, the recombinant microorganism also can include one or more (e.g., one or two) of the following exogenous enzymes used to convert β-alanine to 5-amino-3-oxopentanoyl-CoA: a CoA transferase or a CoA ligase.

In any of the recombinant microorganisms, the recombinant microorganism also can include one or more (e.g., one, two, three, or four) of the following exogenous enzymes used to convert malonyl-CoA and L-aspartate to β-alanyl-[ACP]: a malonyl-CoA reductase, an aspartate α-decarboxylase, a β-alanine-pyruvate aminotransferase, a CoA-transferase and an [ACP]-acetyltransferase. The recombinant microorganism also can include one or more (e.g., one, two, three, or four) of the following exogenous enzymes used to convert malonyl-CoA and L-aspartate to β-alanyl-CoA: a malonyl-CoA reductase, an aspartate α-decarboxylase, a β-alanine-pyruvate aminotransferase and a CoA-transferase. For example, a recombinant microorganism can include an exogenous malonyl-CoA reductase, a β-alanine-pyruvate aminotransferase, a coA transferase and an [ACP]-acetyltransferase. For example, a recombinant microorganism can include an exogenous aspartate α-decarboxylase, a coA transferase and an [ACP]-acetyltransferase. For example, a recombinant microorganism can include an exogenous malonyl-CoA reductase, a β-alanine-pyruvate aminotransferase and a CoA-transferase. For example, a recombinant microorganism can include an exogenous aspartate α-decarboxylase and a coA transferase.

Within an engineered pathway, the enzymes can be from a single source, i.e., from one species or genera, or can be from multiple sources, i.e., different species or genera. Nucleic acids encoding the enzymes described herein have been identified from various organisms and are readily available in publicly available databases such as GenBank or EMBL.

Any of the enzymes described herein that can be used for production of one or more C7 building blocks can have at least 70% sequence identity (homology) (e.g., at least 75%, 80%, 85%, 90%, 91%, 92%, 93%, 94%, 95%, 96%, 97%, 98%, 99%, or 100%) to the amino acid sequence of the corresponding wild-type enzyme. It will be appreciated that the sequence identity can be determined on the basis of the mature enzyme (e.g., with any signal sequence removed) or on the basis of the immature enzyme (e.g., with any signal sequence included). It also will be appreciated that the initial methionine residue may or may not be present on any of the enzyme sequences described herein.

For example, a β-ketothiolase described herein can have at least 70% sequence identity (homology) (e.g., at least 75%, 80%, 85%, 90%, 91%, 92%, 93%, 94%, 95%, 96%, 97%, 98%, 99%, or 100%) to the amino acid sequence of a *Cupriavidus necator* (see GenBank Accession No.

AAC38322.1, SEQ ID NO: 1) or an *Escherichia coli* (see GenBank Accession No. AAC74479.1, SEQ ID NO: 13) β-ketothiolase. See FIG. 8A and FIG. 8D.

For example, a β-ketoacyl synthase described herein can have at least 70% sequence identity (homology) (e.g., at least 75%, 80%, 85%, 90%, 91%, 92%, 93%, 94%, 95%, 96%, 97%, 98%, 99%, or 100%) to the amino acid sequence of the protein encoded by the FabHB gene from *Bacillus subtilis* (see GenBank Accession No. CAA74523.1, SEQ ID NO: 14). See FIG. 8D.

For example, a carboxylate reductase described herein can have at least 70% sequence identity (homology) (e.g., at least 75%, 80%, 85%, 90%, 91%, 92%, 93%, 94%, 95%, 96%, 97%, 98%, 99%, or 100%) to the amino acid sequence of a *Mycobacterium marinum* (see Genbank Accession No. ACC40567.1, SEQ ID NO: 2), a *Mycobacterium smegmatis* (see Genbank Accession No. ABK71854.1, SEQ ID NO: 3), a *Segniliparus rugosus* (see Genbank Accession No. EFV11917.1, SEQ ID NO: 4), a *Mycobacterium massiliense* (see Genbank Accession No. EIV11143.1, SEQ ID NO: 5), a *Segniliparus rotundus* (see Genbank Accession No. ADG98140.1, SEQ ID NO: 6) or a *Mycobacterium smegmatis* carboxylate reductase (see Genbank Accession No. ABK75684.1, SEQ ID NO: 15). See FIG. 8A, FIG. 8B, FIG. 8C, and FIG. 8D.

For example, a ω-transaminase described herein can have at least 70% sequence identity (homology) (e.g., at least 75%, 80%, 85%, 90%, 91%, 92%, 93%, 94%, 95%, 96%, 97%, 98%, 99%, or 100%) to the amino acid sequence of a *Chromobacterium violaceum* (see Genbank Accession No. AAQ59697.1, SEQ ID NO: 7), a *Pseudomonas aeruginosa* (see Genbank Accession No. AAG08191.1, SEQ ID NO: 8), a *Pseudomonas syringae* (see Genbank Accession No. AAY39893.1, SEQ ID NO: 9), a *Rhodobacter sphaeroides* (see Genbank Accession No. ABA81135.1, SEQ ID NO: 10), an *Escherichia coli* (see Genbank Accession No. AAA57874.1, SEQ ID NO: 11), or a *Vibrio fluvialis* (see Genbank Accession No. AEA39183.1, SEQ ID NO: 12) ω-transaminase. Some of these ω-transaminases are diamine ω-transaminases. See FIG. 8C and FIG. 8D.

For example, a CoA-transferase described herein can have at least 70% sequence identity (homology) (e.g., at least 75%, 80%, 85%, 90%, 91%, 92%, 93%, 94%, 95%, 96%, 97%, 98%, 99%, or 100%) to the amino acid sequence of a *Clostridium aminobutyrium* (see GenBank Accession No. CAB60036.2, SEQ ID NO: 19). See FIG. 8E.

The percent identity (homology) between two amino acid sequences can be determined as follows. First, the amino acid sequences are aligned using the BLAST 2 Sequences (Bl2seq) program from the stand-alone version of BLASTZ containing BLASTP version 2.0.14. This stand-alone version of BLASTZ can be obtained from Fish & Richardson's web site (e.g., www.fr.com/blast/) or the U.S. government's National Center for Biotechnology Information web site (www.ncbi.nlm.nih.gov). Instructions explaining how to use the Bl2seq program can be found in the readme file accompanying BLASTZ. Bl2seq performs a comparison between two amino acid sequences using the BLASTP algorithm. To compare two amino acid sequences, the options of Bl2seq are set as follows: -i is set to a file containing the first amino acid sequence to be compared (e.g., C:\seq1.txt); -j is set to a file containing the second amino acid sequence to be compared (e.g., C:\seq2.txt); -p is set to blastp; -o is set to any desired file name (e.g., C:\output.txt); and all other options are left at their default setting. For example, the following command can be used to generate an output file containing a comparison between two amino acid sequences: C:\Bl2seq c:\seq1.txt -j c:\seq2.txt -p blastp -o c:\output.txt. If the two compared sequences share homology (identity), then the designated output file will present those regions of homology as aligned sequences. If the two compared sequences do not share homology (identity), then the designated output file will not present aligned sequences. Similar procedures can be following for nucleic acid sequences except that blastn is used.

Once aligned, the number of matches is determined by counting the number of positions where an identical amino acid residue is presented in both sequences. The percent identity (homology) is determined by dividing the number of matches by the length of the full-length polypeptide amino acid sequence followed by multiplying the resulting value by 100. It is noted that the percent identity (homology) value is rounded to the nearest tenth. For example, 78.11, 78.12, 78.13, and 78.14 is rounded down to 78.1, while 78.15, 78.16, 78.17, 78.18, and 78.19 is rounded up to 78.2. It also is noted that the length value will always be an integer.

It will be appreciated that a number of nucleic acids can encode a polypeptide having a particular amino acid sequence. The degeneracy of the genetic code is well known to the art; i.e., for many amino acids, there is more than one nucleotide triplet that serves as the codon for the amino acid. For example, codons in the coding sequence for a given enzyme can be modified such that optimal expression in a particular species (e.g., bacteria or fungus) is obtained, using appropriate codon bias tables for that species.

Functional fragments of any of the enzymes described herein can also be used in the methods of the document. The term "functional fragment" as used herein refers to a peptide fragment of a protein that has at least 25% (e.g., at least: 30%; 40%; 50%; 60%; 70%; 75%; 80%; 85%; 90%; 95%; 98%; 99%; 100%; or even greater than 100%) of the activity of the corresponding mature, full-length, wild-type protein. The functional fragment can generally, but not always, be comprised of a continuous region of the protein, wherein the region has functional activity.

This document also provides (i) functional variants of the enzymes used in the methods of the document and (ii) functional variants of the functional fragments described above. Functional variants of the enzymes and functional fragments can contain additions, deletions, or substitutions relative to the corresponding wild-type sequences. Enzymes with substitutions will generally have not more than 50 (e.g., not more than one, two, three, four, five, six, seven, eight, nine, ten, 12, 15, 20, 25, 30, 35, 40, 50 or 100) amino acid substitutions (e.g., conservative substitutions). This applies to any of the enzymes described herein and functional fragments. A conservative substitution is a substitution of one amino acid for another with similar characteristics. Conservative substitutions include substitutions within the following groups: valine, alanine and glycine; leucine, valine, and isoleucine; aspartic acid and glutamic acid; asparagine and glutamine; serine, cysteine, and threonine; lysine and arginine; and phenylalanine and tyrosine. The nonpolar hydrophobic amino acids include alanine, leucine, isoleucine, valine, proline, phenylalanine, tryptophan and methionine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Any substitution of one member of the above-mentioned polar, basic or acidic groups by another member of the same group can be deemed a conservative substitution. By contrast, a nonconservative substitution is a substitution of one amino acid for another with dissimilar characteristics.

Deletion variants can lack one, two, three, four, five, six, seven, eight, nine, ten, 11, 12, 13, 14, 15, 16, 17, 18, 19, 20 or 50 amino acid segments (of two or more amino acids) or non-contiguous single amino acids. Additions (addition variants) include fusion proteins containing: (a) any of the enzymes described herein or a fragment thereof; and (b) internal or terminal (C or N) irrelevant or heterologous amino acid sequences. In the context of such fusion proteins, the term "heterologous amino acid sequences" refers to an amino acid sequence other than (a). A heterologous sequence can be, for example a sequence used for purification of the recombinant protein (e.g., FLAG, polyhistidine (e.g., heptahistidine), hemagglutinin (HA), glutathione-S-transferase (GST), or maltosebinding protein (MBP)). Heterologous sequences also can be proteins useful as detectable markers, for example, luciferase, green fluorescent protein (GFP), or chloramphenicol acetyl transferase (CAT). In some embodiments, the fusion protein contains a signal sequence from another protein. In certain microorganisms (e.g., yeast cells), expression and/or secretion of the target protein can be increased through use of a heterologous signal sequence. In some embodiments, the fusion protein can contain a carrier (e.g., KLH) useful, e.g., in eliciting an immune response for antibody generation) or ER or Golgi apparatus retention signals. Heterologous sequences can be of varying length and in some cases can be a longer sequences than the full-length target proteins to which the heterologous sequences are attached.

Engineered microorganisms can naturally express none or some (e.g., one or more, two or more, three or more, four or more, five or more, or six or more) of the enzymes of the pathways described herein. Thus, a pathway within an engineered microorganism can include all exogenous enzymes, or can include both endogenous and exogenous enzymes. Endogenous genes of the engineered microorganisms also can be disrupted to prevent the formation of undesirable metabolites or prevent the loss of intermediates in the pathway through other enzymes acting on such intermediates. Engineered microorganisms can be referred to as recombinant microorganisms or recombinant cells. As described herein recombinant microorganisms can include nucleic acids encoding one or more of a β-ketoacyl synthase, a β-ketothiolase, a dehydrogenase, a decarboxylase, a reductase, a hydratase, a thioesterase, a CoA-transferase, an acylase, an N-acetyltransferase and a ω-transaminase as described herein.

In addition, the production of C7 building blocks can be performed in vitro using the isolated enzymes described herein, using a lysate (e.g., a cell lysate) from a microorganism as a source of the enzymes, or using a plurality of lysates from different microorganisms as the source of the enzymes.

The reactions of the pathways described herein can be performed in one or more microorganism strains (a) naturally expressing one or more relevant enzymes, (b) genetically engineered to express one or more relevant enzymes, or (c) naturally expressing one or more relevant enzymes and genetically engineered to express one or more relevant enzymes. Alternatively, relevant enzymes can be isolated, purified or extracted from of the above types of microorganism cells and used in a purified or semi-purified form. Moreover, such extracts include lysates (e.g. cell lysates) that can be used as sources of relevant enzymes. In the methods provided by the document, all the steps can be performed in microorganism cells, all the steps can be performed using extracted enzymes, or some of the steps can be performed in cells and others can be performed using extracted enzymes.

Enzymes

Enzymes Generating 7-aminoheptanoyl-[ACP]

As depicted in FIG. 1, 7-aminoheptanoyl-[ACP] or a corresponding salt thereof can be biosynthesized from malonyl-CoA or L-aspartate through the intermediate 5-amino-3-oxopentanoyl-[ACP], which can be produced from β-alanyl-[ACP] using a polypeptide having the activity of a β-ketoacyl synthase. In some embodiments, a β-ketoacyl synthase may be classified under EC 2.3.1.41, such as the gene product of fabB, under EC 2.3.1.179 such as the gene product of fabF or under EC 2.3.1.180 such as the gene product of fabH.

β-alanyl-[ACP] can be enzymatically produced from β-alanine using polypeptides having the activity of a CoA transferase and an [ACP]-acetyltransferase. In some embodiments, a CoA-transferase may be classified under EC 2.8.3.- and an [ACP]-acetyltransferase may be the gene product of fluA.

β-alanine itself can be enzymatically produced from malonyl-CoA using polypeptides having the activity of a malonyl-CoA reductase and a β-alanine-pyruvate aminotransferase or from L-aspartate using an aspartate α-decarboxylase. In some embodiments, a malonyl-CoA reductase may be classified under EC 1.2.1.75 and a β-alanine-pyruvate aminotransferase may be classified under EC 2.6.1.18. In some embodiments, an α-aspartate decarboxylase may be classified under EC 4.1.1.11.

The intermediate 5-amino-3-oxopentanoyl-[ACP] can be converted to 7-aminoheptanoyl-[ACP] using polypeptides having the activity of a 3-oxoacyl-[ACP] reductase, a 3-hydroxyacyl-[ACP] dehydratase, an enoyl-[ACP] reductase and a β-ketoacyl synthase. In some embodiments, a 3-oxoacyl-[ACP] reductase can be classified under EC 1.1.1.100, such as the gene product of fabG (Budde et al., *J. Bacteriol.*, 2010, 192(20):5319-5328; Nomura et al., *Appl. Environ. Microbiol.*, 2005, 71(8):4297-4306). In some embodiments, a 3-hydroxyacyl-[ACP] dehydratase can be classified under EC 4.2.1.59, such as the gene product of fabZ. In some embodiments, an enoyl-[ACP] reductase can be classified under EC 1.3.1.10, such as the gene product of fabI. In some embodiments, a β-ketoacyl synthase may be classified under EC 2.3.1.41, such as the gene product of fabB or under EC 2.3.1.179 such as the gene product of fabF.

Enzymes Generating 7-Aminoheptanoyl-CoA

Figure 2:
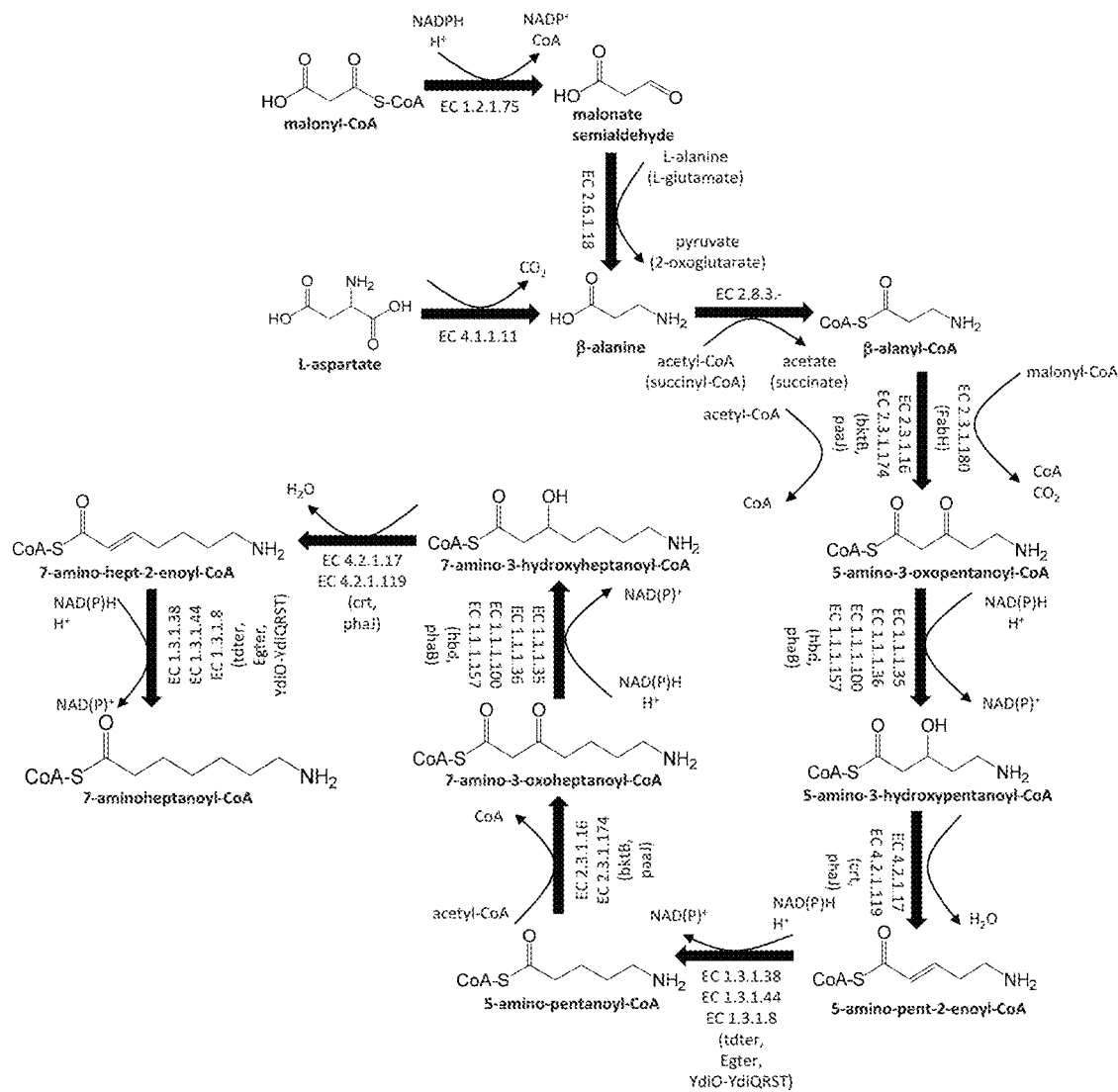
FIG. 2 is a schematic of exemplary biochemical pathways leading to 7-aminoheptanoyl-CoA using malonyl-CoA and L-aspartate as central metabolites.

As depicted in FIG. 2, 7-aminoheptanoyl-CoA can be biosynthesized from malonyl-CoA or L-aspartate through the intermediate 5-amino-3-oxopentanoyl-CoA, which can be produced from β-alanyl-CoA using polypeptides having the activity of a β-ketoacyl synthase or a β-ketothiolase. In some embodiments, a β-ketothiolase may be classified under EC 2.3.1.16, such as the gene product of bktB or under EC 2.3.1.174 such as the gene product of paaJ. In some embodiments, a β-ketoacyl synthase may be classified under EC 2.3.1.180 such as the gene product of fabH.

β-alanyl-CoA can be enzymatically produced from β-alanine using a polypeptide having the activity of a CoA transferase. In some embodiments, a CoA transferase may be classified under EC 2.8.3.-.

β-alanine itself can be enzymatically produced from malonyl-CoA using polypeptides having the activity of a malonyl-CoA-reductase and a β-alanine-pyruvate aminotransferase or from L-aspartate using a polypeptide having the activity of an aspartate α-decarboxylase. In some embodiments, a malonyl-CoA-reductase may be classified under EC 1.2.1.75 and a β-alanine-pyruvate aminotransferase may be classified under EC 2.6.1.18. In some embodiments, an α-aspartate decarboxylase may be classified under EC 4.1.1.11.

The intermediate 5-amino-3-oxopentanoyl-CoA can be converted to 7-aminoheptanoyl-CoA using polypeptides having the activity of a 3-hydroxyacyl-CoA dehydrogenase, an enoyl-CoA hydratase, a trans-2-enoyl-CoA reductase and a β-ketothiolase. In some embodiments, a 3-hydroxyacyl-CoA dehydrogenase may be classified, for example, under EC 1.1.1.- such as EC 1.1.1.35 (e.g., the gene product of fadB), EC 1.1.1.36 (e.g., the gene product of phaB), or EC 1.1.1.157 (e.g., the gene product of hbd). In some embodiments, an enoyl-CoA hydratase may be classified under EC 4.2.1.17 such as the gene product of crt or under EC 4.2.1.119 such as the gene product of phaJ. In some embodiments, a trans-2-enoyl-CoA reductase may be classified, for example, under EC 1.3.1.38 or EC 1.3.1.44, such as the gene product of ter (Nishimaki et al., *J. Biochem.*, 1984, 95:1315-1321; Shen et al., 2011, supra) or tdter (Bond-Watts et al., *Biochemistry*, 2012, 51:6827-6837) or EC 1.3.1.8 (Inui et al., *Eur. J. Biochem.*, 1984, 142, 121-126). In some embodiments, a β-ketothiolase may be classified under EC 2.3.1.16 such as the gene product of bktB or under EC 2.3.1.174 such as the gene product of paaJ.

Enzymes Generating 7-Aminoheptanoate

Figure 3:
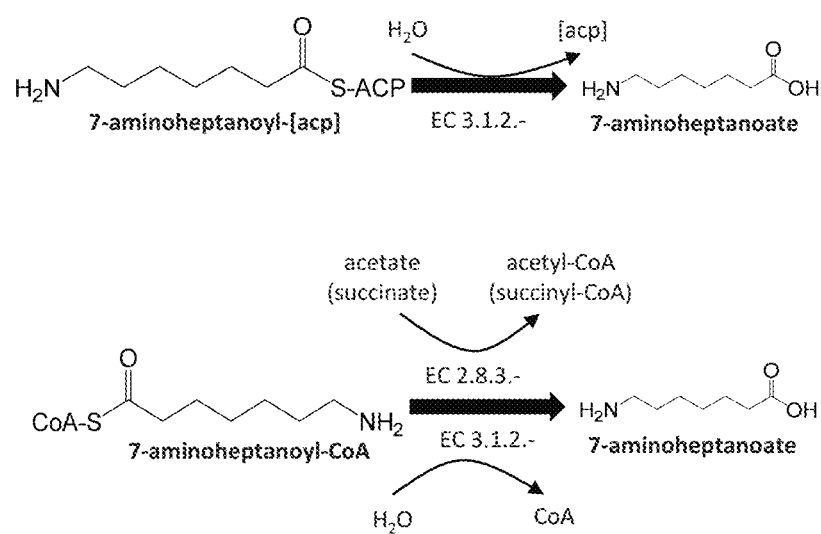
FIG. 3 is a schematic of an exemplary biochemical pathway leading to 7-aminoheptanoate using either 7-aminoheptanoyl-[ACP] or 7-aminoheptanoyl-CoA as a central precursor.

As depicted in FIG. 3, 7-aminoheptanoyl-[ACP] is converted to 7-aminoheptanoate using a polypeptide having the activity of a thioesterase and 7-aminoheptanoyl-CoA is converted to 7-aminoheptanoate using polypeptides having the activity of a thioesterase or a CoA-transferase.

In some embodiments, a thioesterase may be classified under EC 3.1.2.-, resulting in the production of 7-aminoheptanoate. The thioesterase can be the gene product of YciA or Acot13 (Cantu et al., *Protein Science*, 2010, 19, 1281-1295; Zhuang et al., *Biochemistry*, 2008, 47(9):2789-2796; Naggert et al., *J. Biol. Chem.*, 1991, 266(17):11044-11050). In some embodiments, a CoA-transferase may be classified under, for example, EC 2.8.3.- such as the gene product of cat2 from *Clostridium kluyveri*, abfT from *Clostridium aminobutyricum* or the 4-hydroxybuanoate CoA-transferase from *Clostridium viride*.

Figure 4:
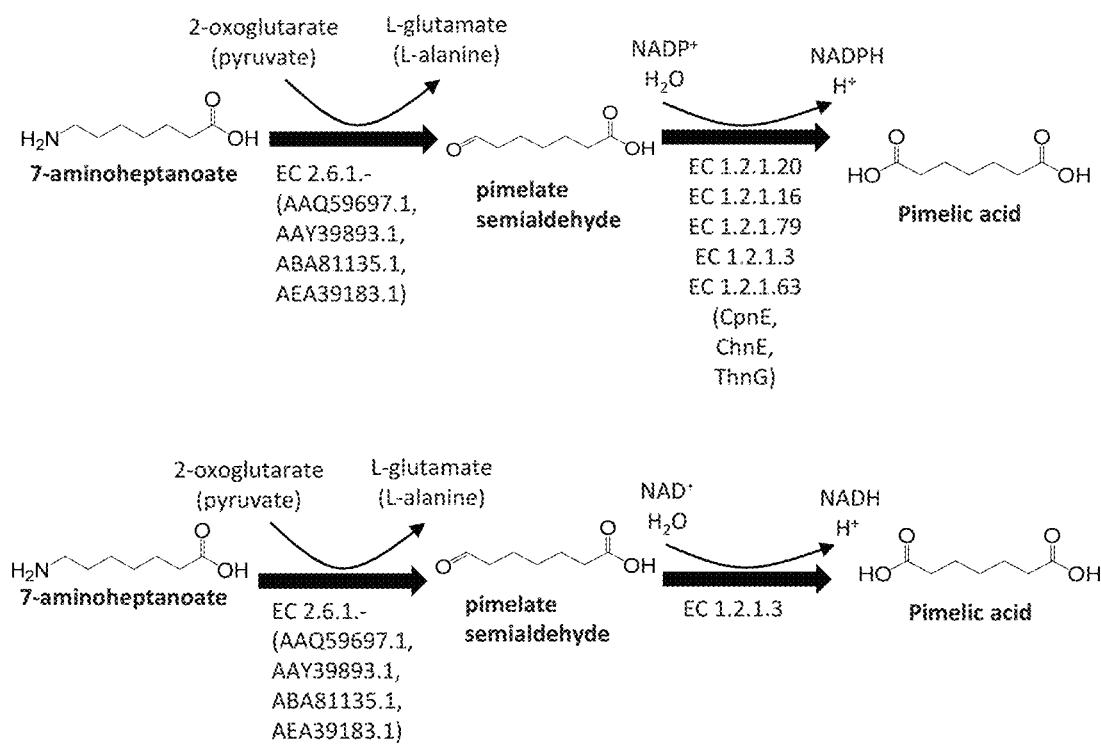
FIG. 4 is a schematic of exemplary biochemical pathways leading to pimelic acid using 7-aminoheptanoate as a central precursor.

Enzymes Generating the Terminal Carboxyl Groups in the Biosynthesis of Pimelic Acid As depicted in FIG. 4, 7-aminoheptanoate can be enzymatically converted to pimelic acid. The terminal carboxyl group leading to the production of pimelic acid can be enzymatically formed using polypeptides having the activity of an aldehyde dehydrogenase, a 5-oxopentanoate dehydrogenase, a 6-oxohexanoate dehydrogenase, or a 7-oxoheptanoate dehydrogenase.

In some embodiments, the second terminal carboxyl group leading to the synthesis of pimelic acid can be enzymatically formed in pimelate semialdehyde by an aldehyde dehydrogenase classified under EC 1.2.1.3 (Guerrillot & Vandecasteele, *Eur. J. Biochem.*, 1977, 81, 185-192). See, FIG. 4.

In some embodiments, the second terminal carboxyl group leading to the synthesis of pimelic acid is enzymatically formed in pimelate semialdehyde by an aldehyde dehydrogenase classified under EC 1.2.1.- such as a 5-oxopentanoate dehydrogenase classified, for example, under EC 1.2.1.20, such as the gene product of CpnE, a 6-oxohexanoate dehydrogenase classified, for example, under EC 1.2.1.63 such as the gene product of ChnE from *Acinetobacter* sp., or a 7-oxoheptanoate dehydrogenase such as the gene product of ThnG from *Sphingomonas macrogolitabida* (Iwaki et al., *Appl. Environ. Microbiol.*, 1999, 65(11), 5158-5162; Lopez-Sanchez et al., *Appl. Environ. Microbiol.*, 2010, 76(1), 110-118)). See, FIG. 2.

Figure 5A:
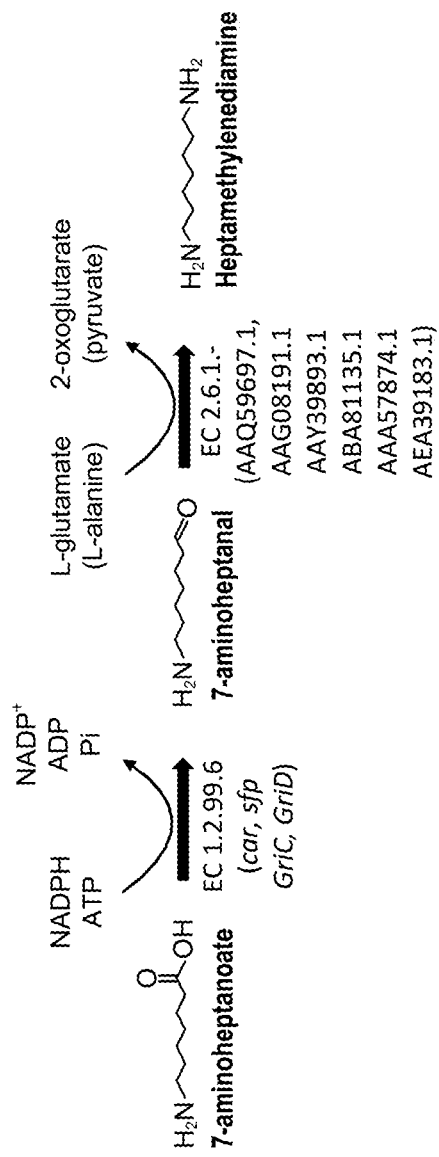
FIG. 5A is a schematic of an exemplary biochemical pathway leading to heptamethylenediamine using 7-aminoheptanoate as a central precursor.
Figure 5B:
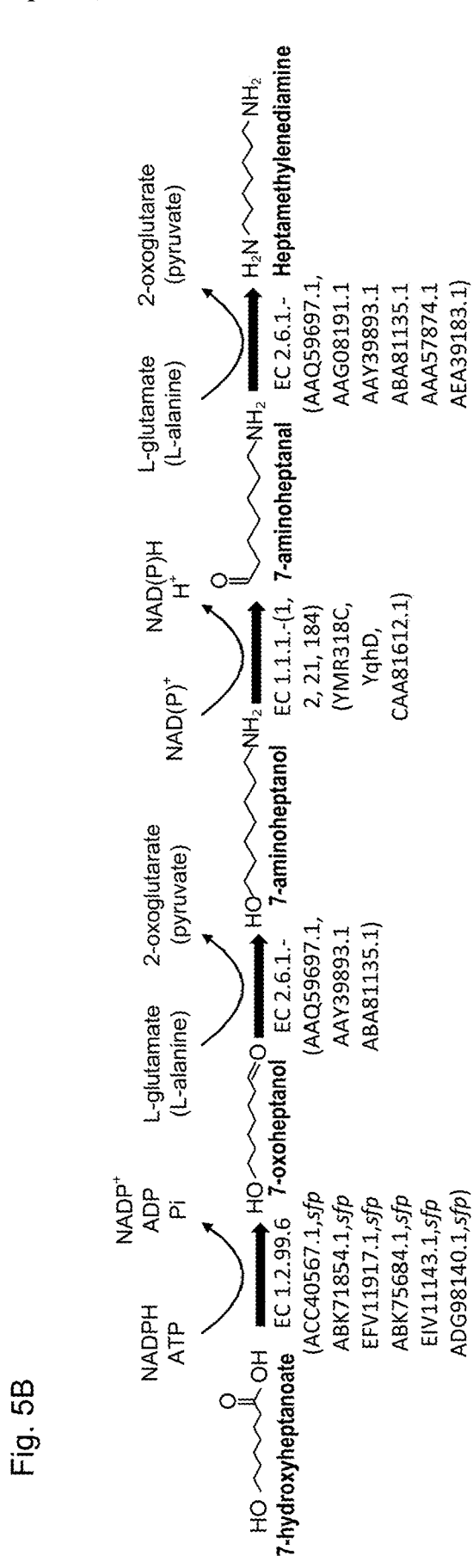
FIG. 5B is a schematic of an exemplary biochemical pathway leading to heptamethylenediamine using 7-hydroxyheptanoate as a central precursor.
Figure 5C:
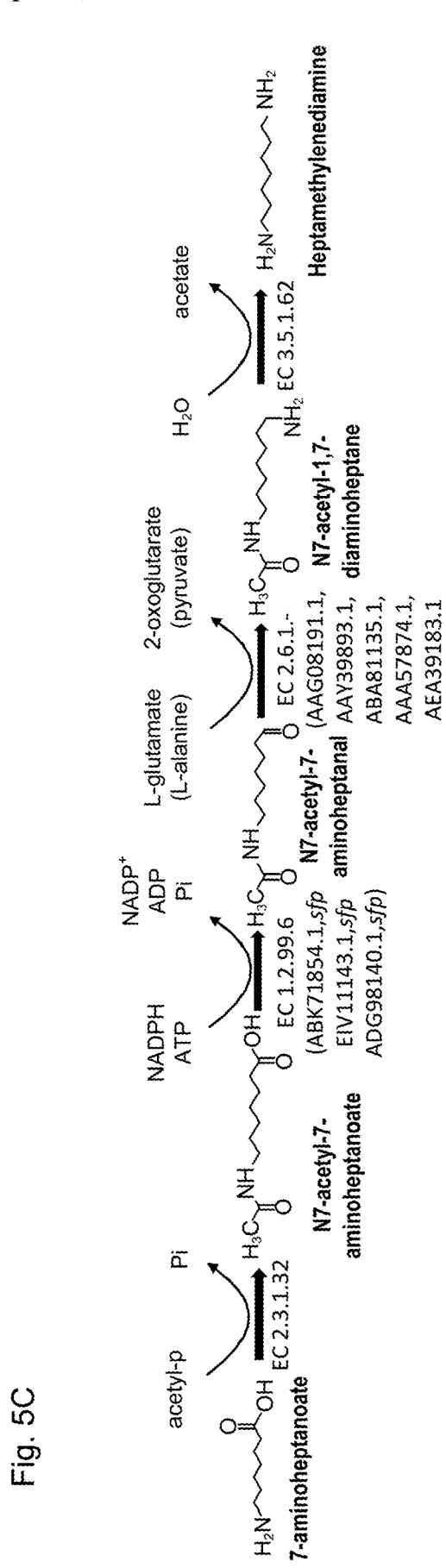
FIG. 5C is a schematic of an exemplary biochemical pathway leading to heptamethylenediamine using 7-aminoheptanoate as a central precursor.
Figure 5D:
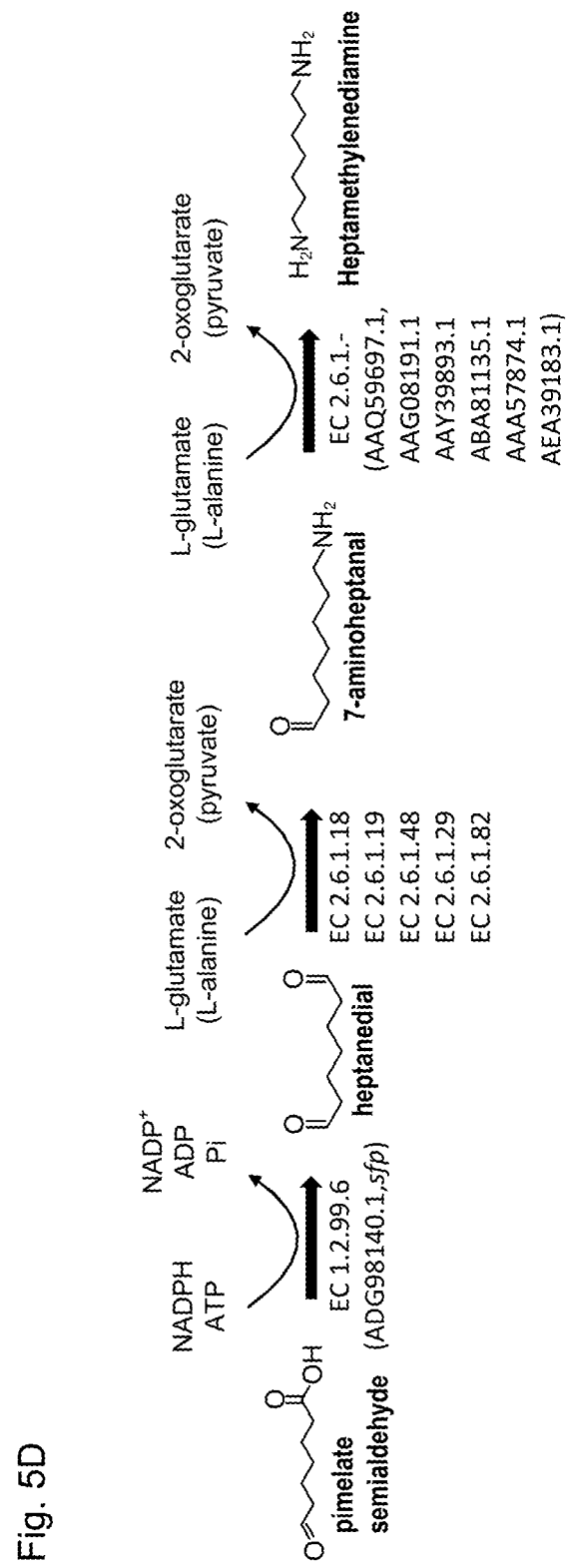
FIG. 5D is a schematic of an exemplary biochemical pathway leading to heptamethylenediamine using pimelate semialdehyde as a central precursor.
Figure 5E:
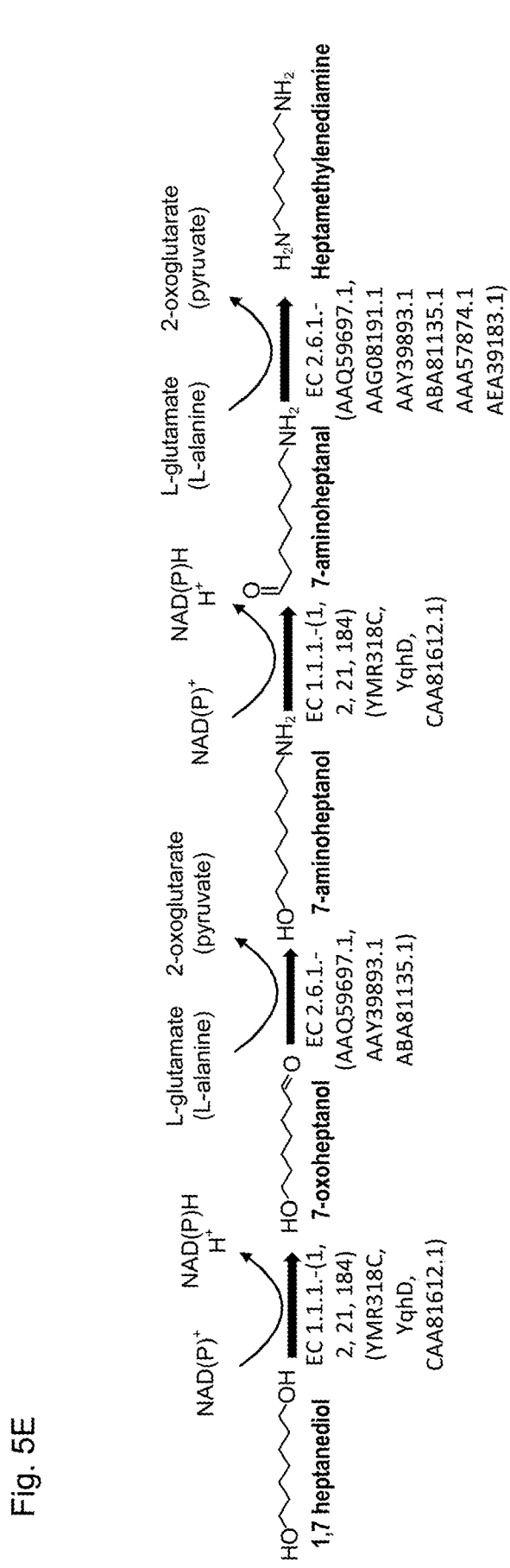
FIG. 5E is a schematic of an exemplary biochemical pathway leading to heptamethylenediamine using 1,7 heptanediol as a central precursor.

Enzymes Generating the Terminal Amine Groups in the Biosynthesis of Heptamethylenediamine As depicted in FIG. 5A and FIG. 5C, terminal amine groups can be enzymatically formed or removed using polypeptides having the activity of a ω-transaminase or a deacylase.

In some embodiments, a terminal amine group leading to the synthesis of 7-aminoheptanoic acid is enzymatically formed in pimelate semialdehyde by a polypeptide having the activity of a ω-transaminase classified, for example, under EC 2.6.1.-, e.g., EC 2.6.1.18, EC 2.6.1.19, EC 2.6.1.29, EC 2.6.1.48, or EC 2.6.1.82 such as that obtained from *Chromobacterium violaceum* (Genbank Accession No. AAQ59697.1, SEQ ID NO: 7), *Pseudomonas aeruginosa* (Genbank Accession No. AAG08191.1, SEQ ID NO: 8), *Pseudomonas syringae* (Genbank Accession No. AAY39893.1, SEQ ID NO: 9), *Rhodobacter sphaeroides* (Genbank Accession No. ABA81135.1, SEQ ID NO: 10), *Vibrio fluvialis* (Genbank Accession No. AEA39183.1, SEQ ID NO: 12), *Streptomyces griseus*, or *Clostridium viride*. See FIG. 8C and FIG. 8D.

An additional ω-transaminase that can be used in the methods and microorganisms described herein is from *Escherichia coli* (Genbank Accession No. AAA57874.1, SEQ ID NO: 11). Some of the ω-transaminases classified, for example, under EC 2.6.1.29 or EC 2.6.1.82 are diamine ω-transaminases (e.g., SEQ ID NO: 11).

The reversible ω-transaminase from *Chromobacterium violaceum* (Genbank Accession No. AAQ59697.1, SEQ ID NO: 7) has demonstrated analogous activity accepting 7-aminoheptanoic acid as amino donor, thus forming the first terminal amine group in pimelate semialdehyde (Kaulmann et al., *Enzyme and Microbial Technology*, 2007, 41, 628-637).

The reversible 4-aminobubyrate: 2-oxoadipate transaminase from *Streptomyces griseus* has demonstrated activity for the conversion of 7-aminoheptanoate to pimelate semialdehyde (Yonaha et al., *Eur. J. Biochem.*, 1985, 146, 101-106).

The reversible 5-aminovalerate transaminase from *Clostridium viride* has demonstrated activity for the conversion of 7-aminoheptanoate to pimelate semialdehyde (Barker et al., *J. Biol. Chem.*, 1987, 262(19), 8994-9003).

In some embodiments, the second terminal amine group leading to the synthesis of heptamethylenediamine is enzymatically formed in 7-aminoheptanal by a diamine transaminase classified, for example, under EC 2.6.1.29 or classified, for example, under EC 2.6.1.82, such as the gene product of YgjG from *E. coli* (Genbank Accession No. AAA57874.1, SEQ ID NO: 12). The ω-transaminases set forth in SEQ ID NOs:7-10 and 11 also can be used to produce heptamethylenediamine. See, FIG. 8C and FIG. 8D.

The gene product of ygjG accepts a broad range of diamine carbon chain length substrates, such as putrescine, cadaverine and spermidine (Samsonova et al., *BMC Microbiology*, 2003, 3:2).

The diamine transaminase from *E. coli* strain B has demonstrated activity for 1,7 diaminoheptane (Kim, *The Journal of Chemistry*, 1964, 239(3), 783-786).

In some embodiments, the second terminal amine group leading to the synthesis of heptamethylenediamine is enzymatically formed in N7-acetyl-1,7-diaminoheptane by a polypeptide having the activity of a deacylase classified, for example, under EC 3.5.1.62.

Figure 7:
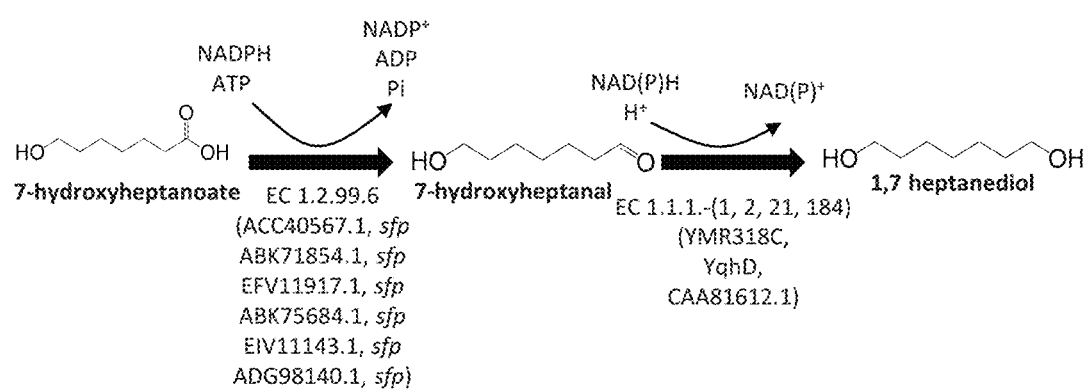
FIG. 7 is a schematic of an exemplary biochemical pathway leading to 1,7-heptanediol using 7-hydroxyheptanoate as a central precursor.

Enzymes Generating the Terminal Hydroxyl Groups in the Biosynthesis of 1,7 Heptanediol As depicted in FIG. 7, the terminal hydroxyl group can be enzymatically formed using a polypeptide having the activity of an alcohol dehydrogenase. For example, the second terminal hydroxyl group leading to the synthesis of 1,7 heptanediol can be enzymatically formed in 7-hydroxyheptanal by an alcohol dehydrogenase classified under EC 1.1.1.- (e.g., EC 1.1.1.1, 1.1.1.2, 1.1.1.21, or 1.1.1.184) such as the gene product of YMR318C or YqhD (Liu et al., *Microbiology*, 2009, 155, 2078-2085; Larroy et al., 2002, *Biochem J.*, 361(Pt 1), 163-172; Jarboe, 2011, Appl. Microbiol. Biotechnol., 89(2), 249-257) or the protein having GenBank Accession No. CAA81612.1.

Enzymes Generating 5-Amino-3-Oxopentanoyl-CoA

As depicted in FIG. 2, 5-amino-3-oxopentanoyl-CoA or a salt thereof can be biosynthesized from malonyl-CoA or L-aspartate through β-alanine, which can be produced from β-alanyl-CoA using a polypeptide having the activity of a β-ketoacyl synthase, a β-ketothiolase, or a CoA-transferase. In some embodiments, a β-ketothiolase may be classified under EC 2.3.1.16, such as the gene product of bktB or under EC 2.3.1.174 such as the gene product of paaJ. In some embodiments, a β-ketoacyl synthase may be classified under EC 2.3.1.180 such as the gene product of fabH, under EC 2.3.1.179 such as the gene product of fabF or under EC 2.3.1.41 such as the gene product of fabB. In some embodiments, a CoA-transferase may be classified under EC 2.8.3.- such as the gene product of abfT.

Biochemical Pathways

Pathways to 7-Aminoheptanoate

In some embodiments, 5-amino-3-oxopentanoyl-[ACP] and 5-amino-3-oxopentanoyl-CoA or corresponding salts thereof are synthesized from the central metabolite, malonyl-CoA, by conversion of malonyl-CoA to malonate semialdehyde by a polypeptide having the activity of a malonyl CoA reductase classified, for example, under EC 1.2.1.75; followed by conversion of malonate semialdehyde to β-alanine by a polypeptide having the activity of a β-alanine-pyruvate aminotransferase classified, for example, under EC 2.6.1.18; followed by conversion of β-alanine to β-alanyl-CoA by a polypeptide having the activity of a CoA transferase classified under, for example, EC 2.8.3.-. In some embodiments in which β-alanyl-[ACP] is used to synthesise 5-amino-3-oxopentanoyl-[ACP], β-alanyl-CoA is converted to β-alanyl-[ACP] by a polypeptide having the activity of an [ACP]-acetyltransferase, such as that encoded by the fluA gene. See FIG. 1 and FIG. 2.

In some embodiments, β-alanyl-[ACP] and β-alanyl-CoA are synthesized from the central metabolite, L-aspartate, by conversion of L-aspartate to β-alanine by a polypeptide having the activity of an aspartate α-decarboxylase classified, for example, under EC 4.1.1.11; followed by conversion of β-alanine to β-alanyl-CoA by a polypeptide having the activity of a CoA transferase, classified under, for example, EC 2.8.3.-.

In some embodiments in which β-alanyl-[ACP] is used to synthesise 5-amino-3-oxopentanoyl-[ACP], β-alanyl-CoA is converted to β-alanyl-[ACP] by a polypeptide having the activity of an [ACP]-acetyltransferase encoded, for example, by the fluA gene.

Where β-alanyl-[ACP] is used to synthesise 5-amino-3-oxopentanoyl-[ACP], as shown in FIG. 1, β-alanyl-[ACP] is converted to 5-amino-3-oxopentanoyl-[ACP] by a polypeptide having the activity of a β-ketoacyl synthase classified, for example, under EC 2.3.1.41 such as the gene product of fabB or under EC 2.3.1.179 such as the gene product of fabF or under EC 2.3.1.180 such as the gene product of fabH; followed by conversion of 5-amino-3-oxopentanoyl-[ACP] to 5-amino-3-hydroxypentanoyl-[ACP] by a polypeptide having the activity of a 3-oxoacyl-[ACP]reductase classified, for example, under EC 1.1.1.100 such as the gene product of fabG; followed by conversion of 5-amino-3-hydroxypentanoyl-[ACP] to 5-amino-pent-2-enoyl-[ACP] by a polypeptide having the activity of a 3-hydroxyacyl-[ACP] dehydratase classified, for example, under EC 4.2.1.59 such as the gene product of fabZ; followed by conversion of 5-amino-pent-2-enoyl-[ACP] to 5-amino-pentanoyl-[ACP] by a polypeptide having the activity of an enoyl-[ACP] reductase classified, for example, under EC 1.3.1.10 such as the gene product of fabI; followed by conversion of 5-amino-pentanoyl-[ACP] to 7-amino-3-oxo-heptanoyl-[ACP] by a polypeptide having the activity of a β-ketoacyl synthase classified, for example, under EC 2.3.1.41 such as the gene product of fabB or under EC 2.3.1.179 such as the gene product of fabF; followed by conversion of 7-amino-3-oxoheptanoyl-[ACP] to 7-amino-3-hydroxyheptanoyl-[ACP] by a polypeptide having the activity of a 3-oxoacyl-[ACP] reductase classified, for example, under EC 1.1.1.100 such as the gene product of fabG; followed by conversion of 7-amino-3-hydroxyheptanoyl-[ACP] to 7-amino-hept-2-enoyl-[ACP] by a polypeptide having the activity of a 3-hydroxyacyl-[ACP] dehydratase classified, for example, under EC 4.2.1.59 such as the gene product of fabZ; followed by conversion of 7-amino-hept-2-enoyl-[ACP] to 7-aminoheptanoyl-[ACP] by a polypeptide having the activity of an enoyl-[ACP] reductase classified, for example, under EC 1.3.1.10 such as the gene product of fabI. See FIG. 1.

7-aminoheptanoyl-[ACP] is then converted to 7-amino-heptanoate or a corresponding salt thereof by a polypeptide having the activity of a thioesterase classified, for example, under EC 3.1.2.-. See FIG. 3.

Where β-alanyl-CoA is used to synthesise 5-amino-3-oxopentanoyl-CoA, as shown in FIG. 2, β-alanyl-CoA is converted to 5-amino-3-oxopentanoyl-CoA by a polypeptide having the activity of a β-ketoacyl synthase classified, for example, under EC 2.3.1.180 such as the gene product of fabH or by a polypeptide having the activity of a β-ketothiolase classified, for example, under EC 2.3.1.16 such as the gene product of bktB or under EC 2.3.1.174 such as the gene product of paaJ, followed by conversion of 5-amino-3-oxopentanoyl-CoA to 5-amino-3-hydroxypentanoyl-CoA by a polypeptide having the activity of a 3-hydroxyacyl-CoA dehydrogenase classified, for example, under EC 1.1.1.- such as EC 1.1.1.35 (e.g., the gene product of fadB), EC 1.1.1.36 (e.g., the gene product of phaB), or EC 1.1.1.157 (e.g., the gene product of hbd); followed by conversion of 5-amino-3-hydroxypentanoyl-CoA to 5-amino-pent-2-enoyl-CoA using a polypeptide having the activity of an enoyl-CoA hydratase classified under, for example, EC 4.2.1.17 such as the gene product of crt or under EC 4.2.1.119 such as the gene product of phaJ; followed by conversion of 5-amino-pent-2-enoyl-CoA to 5-amino-pentanoyl-CoA by a polypeptide having the activity of a trans-2-enoyl-CoA reductase classified under EC 1.3.1.38 or EC 1.3.1.44, such as the gene product of ter (Nishimaki et al., *J. Biochem.*, 1984, 95:1315-1321; Shen et al., 2011, supra) or tdter (Bond-Watts et al., *Biochemistry*, 2012, 51:6827-6837) or EC 1.3.1.8 (Inui et al., *Eur. J. Biochem.*, 1984, 142, 121-126); followed by conversion of 5-amino-pentanoyl-CoA to 7-amino-3-oxoheptanoyl-CoA by a polypeptide having the activity of a β-ketothiolase classified under, for example, EC 2.3.1.16 such as the gene product of bktB or under EC 2.3.1.174 such as the gene product of paaJ; followed by conversion of 7-amino-3-oxoheptanoyl-CoA to 7-amino-3-hydroxyheptanoyl-CoA by a polypeptide having the activity of a 3-hydroxyacyl-CoA dehydrogenase classified, for example, under EC 1.1.1.- such as EC 1.1.1.35 (e.g., the gene product of fadB), EC 1.1.1.36 (e.g., the gene product of phaB), or EC 1.1.1.157 (e.g., the gene product of hbd); followed by conversion of 7-amino-3-hydroxyheptanoyl-CoA to 7-amino-hept-2-enoyl-CoA by a polypeptide having the activity of an enoyl-CoA-hydratase classified under, for example, EC 4.2.1.17 such as the gene product of crt or under EC 4.2.1.119 such as the gene product of phaJ; followed by conversion of 7-amino-hept-2-enoyl-CoA to 7-aminoheptanoyl-CoA by a polypeptide having the activity of a trans-2-enoyl-CoA-reductase classified under EC 1.3.1.38 or EC 1.3.1.44, such as the gene product of ter (Nishimaki et al., *J. Biochem.*, 1984, 95:1315-1321; Shen et al., 2011, supra) or tdter (Bond-Watts et al., *Biochemistry*, 2012, 51:6827-6837) or EC 1.3.1.8 (Inui et al., *Eur. J. Biochem.*, 1984, 142, 121-126). See FIG. 0.2.

7-aminoheptanoyl-CoA is then converted to 7-aminoheptanoate or a corresponding salt thereof by a polypeptide having the activity of a thioesterase classified, for example, under EC 3.1.2.- or a polypeptide having the activity of a CoA-transferase classified, for example, under EC 2.8.3.-. See FIG. 3.

Pathways Using 7-Aminoheptanoate as Central Precursor to Pimelic Acid

In some embodiments, pimelic acid is synthesized from 7-aminoheptanoate (or corresponding salts thereof), by conversion of 7-aminoheptanoate to pimelate semialdehyde by a polypeptide having the activity of a ω-transaminase classified, for example, under EC 2.6.1.-, e.g., EC 2.6.1.18, EC 2.6.1.19, EC 2.6.1.29, EC 2.6.1.48, or EC 2.6.1.82 such as that obtained from *Chromobacterium violaceum* (Genbank Accession No. AAQ59697.1, SEQ ID NO: 7), *Pseudomonas aeruginosa* (Genbank Accession No. AAG08191.1, SEQ ID NO: 8), *Pseudomonas syringae* (Genbank Accession No. AAY39893.1, SEQ ID NO: 9), *Rhodobacter sphaeroides* (Genbank Accession No. ABA81135.1, SEQ ID NO: 10), *Vibrio fluvialis* (Genbank Accession No. AEA39183.1, SEQ ID NO: 12), *Streptomyces griseus*, or *Clostridium viride*. See, FIG. 4.

Pimelate semialdehyde is then converted to pimelic acid by a polypeptide having the activity of a dehydrogenase classified, for example, under EC 1.2.1.- such as a 7-oxoheptanoate dehydrogenase (e.g., the gene product of ThnG), a 6-oxohexanoate dehydrogenase (e.g., the gene product of ChnE), a glutarate semialdehyde dehydrogenase classified, for example, under EC 1.2.1.20, a 5-oxopentanoate dehydrogenase such as the gene product of CpnE, or a polypeptide having the activity of an aldehyde dehydrogenase classified under EC 1.2.1.3. See FIG. 4.

Pathway Using 7-Aminoheptanoate as Central Precursor to 7-Hydroxyheptanoate

In some embodiments, 7-hydroxyheptanoate is synthesized from the central precursor, 7-aminoheptanoate, (or corresponding salts thereof), by conversion of 7-aminoheptanoate to pimelate semialdehyde by a polypeptide having the activity of an alcohol dehydrogenase classified, for example, under EC 1.1.1.2 such as the gene product of YMR318C, a 6-hydroxyhexanoate dehydrogenase classified, for example, under EC 1.1.1.258, a 5-hydroxypentanoate dehydrogenase classified, for example, under EC 1.1.1.- such as the gene product of cpnD, or a 4-hydroxybutanoate dehydrogenase classified, for example, under EC 1.1.1.- such as the gene product of gabD; followed by conversion of pimelate semialdehyde to 7-hydroxyheptanoate by a polypeptide having the activity of a ω-transaminase classified, for example, under EC 2.6.1.-, e.g., EC 2.6.1.18, EC 2.6.1.19, EC 2.6.1.29, EC 2.6.1.48, or EC 2.6.1.82 such as that obtained from *Chromobacterium violaceum* (Genbank Accession No. AAQ59697.1, SEQ ID NO: 7), *Pseudomonas aeruginosa* (Genbank Accession No. AAG08191.1, SEQ ID NO: 8), *Pseudomonas syringae* (Genbank Accession No. AAY39893.1, SEQ ID NO: 9), *Rhodobacter sphaeroides* (Genbank Accession No. ABA81135.1, SEQ ID NO: 10), *Vibrio fluvialis* (Genbank Accession No. AEA39183.1, SEQ ID NO: 12), *Streptomyces griseus*, or *Clostridium viride*. See, FIG. 6.

Pathway Using 7-Aminoheptanoate, 7-Hydroxyheptanoate, Pimelate Semialdehyde, or 1,7-Heptanediol as a Central Precursor to Heptamethylenediamine In some embodiments, heptamethylenediamine is synthesized from the central precursor, 7-aminoheptanoate, by conversion of 7-aminoheptanoate to 7-aminoheptanal by a polypeptide having the activity of a carboxylate reductase classified, for example, under EC 1.2.99.6 such as the gene product of car in combination with a phosphopantetheine transferase enhancer (e.g., encoded by a sfp gene from *Bacillus subtilis* or npt gene from *Nocardia*) or the gene products of GriC and GriD from *Streptomyces griseus* (Suzuki et al., *J. Antibiot.*, 2007, 60(6), 380-387); followed by conversion of 7-aminoheptanal to heptamethylenediamine by a polypeptide having the activity of a ω-transaminase such as a ω-transaminase in EC 2.6.1.-, (e.g., EC 2.6.1.18, EC 2.6.1.19, EC 2.6.1.48, EC 2.6.1.82 such as SEQ ID NOs:7-12). The carboxylate reductase can be obtained, for example, from *Mycobacterium marinum* (Genbank Accession No. ACC40567.1, SEQ ID NO: 2), *Mycobacterium smegmatis* (Genbank Accession No. ABK71854.1, SEQ ID NO: 3), *Segniliparus rugosus* (Genbank Accession No. EFV11917.1, SEQ ID NO: 4), *Mycobacterium massiliense* (Genbank Accession No. EIV11143.1, SEQ ID NO: 5), *Segniliparus rotundus* (Genbank Accession No. ADG98140.1, SEQ ID NO: 6) or *Mycobacterium smegmatis* (Genbank Accession No. ABK75684.1, SEQ ID NO: 15). See FIG. 5A-E.

The carboxylate reductase encoded by the gene product of car and enhancer npt or sfp has broad substrate specificity, including terminal difunctional C4 and C5 carboxylic acids (Venkitasubramanian et al., *Enzyme and Microbial Technology*, 2008, 42, 130-137).

In some embodiments, heptamethylenediamine is synthesized from the central precursor, 7-hydroxyheptanoate (which can be produced as described in FIGS. 1, 2, 3 and 6), by conversion of 7-hydroxyheptanoate to 7-hydroxyheptanal by a polypeptide having the activity of a carboxylate reductase classified, for example, under EC 1.2.99.6 such as the gene product of car (see above) in combination with a phosphopantetheine transferase enhancer (e.g., encoded by a sfp gene from *Bacillus subtilis* or npt gene from *Nocardia*) or the gene product of GriC & GriD (Suzuki et al., 2007, supra); followed by conversion of 7-aminoheptanal to 7-aminoheptanol by a polypeptide having the activity of a ω-transaminase classified, for example, under EC 2.6.1.18, EC 2.6.1.19, EC 2.6.1.29, EC 2.6.1.48, or EC 2.6.1.82 such as SEQ ID NOs:7-12, see above; followed by conversion to 7-aminoheptanal by a polypeptide having the activity of an alcohol dehydrogenase classified, for example, under EC 1.1.1.- (e.g., EC 1.1.1.1, EC 1.1.1.2, EC 1.1.1.21, or EC 1.1.1.184) such as the gene product of YMR318C or YqhD (Liu et al., *Microbiology*, 2009, 155, 2078-2085; Larroy et al., 2002, *Biochem J.*, 361(Pt 1), 163-172; Jarboe, 2011, *Appl. Microbiol. Biotechnol.*, 89(2), 249-257) or the protein having GenBank Accession No. CAA81612.1; followed by conversion to heptamethylenediamine by a polypeptide having the activity of a ω-transaminase classified, for example, under EC 2.6.1.18, EC 2.6.1.19, EC 2.6.1.29, EC 2.6.1.48, or EC 2.6.1.82 such as SEQ ID NOs:7-12, see above. See FIG. 5B.

In some embodiments, heptamethylenediamine is synthesized from the central precursor, 7-aminoheptanoate, by conversion of 7-aminoheptanoate to N7-acetyl-7-aminoheptanoate by a polypeptide having the activity of an N-acetyltransferase such as a lysine N-acetyltransferase classified, for example, under EC 2.3.1.32; followed by conversion to N7-acetyl-7-aminoheptanal by a polypeptide having the activity of a carboxylate reductase classified, for example, under EC 1.2.99.6 such as the gene product of car (see above, e.g., SEQ ID NO: 4, 5, or 6) in combination with a phosphopantetheine transferase enhancer (e.g., encoded by a sfp gene from *Bacillus subtilis* or npt gene from *Nocardia*) or the gene product of GriC & GriD; followed by conversion to N7-acetyl-1,7-diaminoheptane by a ω-transaminase classified, for example, under EC 2.6.1.18, EC 2.6.1.19, EC 2.6.1.29, EC 2.6.1.48, or EC 2.6.1.82 such as SEQ ID NOs:7-12, see above; followed by conversion to heptamethylenediamine by a polypeptide having the activity of a deacylase classified, for example, under EC 3.5.1.62. In some embodiments, the second terminal amine group leading to the synthesis of heptamethylenediamine is enzymatically formed by a deacetylase classified, for example, under EC 3.5.1.62 such as an acetylputrescine deacetylase. The acetylputrescine deacetylase from *Micrococcus luteus* K-11 accepts a broad range of carbon chain length substrates, such as acetylputrescine, acetylcadaverine and N8 acetylspermidine (see, for example, Suzuki et al., 1986, BBA—General Subjects, 882(1):140-142). See, FIG. 5C.

In some embodiments, heptamethylenediamine is synthesized from the central precursor, pimelate semialdehyde, by conversion of pimelate semialdehyde to heptanedial by a carboxylate reductase classified, for example, under EC 1.2.99.6 such as the gene product of car (see above, e.g., SEQ ID NO:6) in combination with a phosphopantetheine transferase enhancer (e.g., encoded by a sfp gene from *Bacillus subtilis* or npt gene from *Nocardia*) or the gene product of GriC & GriD; followed by conversion to 7-aminoheptanal by a ω-transaminase classified, for example, under EC 2.6.1.18, EC 2.6.1.19, EC 2.6.1.29, EC 2.6.1.48, or EC 2.6.1.82; followed by conversion to heptamethylenediamine by a ω-transaminase classified, for example, under EC 2.6.1.18, EC 2.6.1.19, EC 2.6.1.29, EC 2.6.1.48, or EC 2.6.1.82 such as SEQ ID NOs:7-12. See FIG. 5D.

In some embodiments, heptamethylenediamine is synthesized from 1,7-heptanediol by conversion of 1,7-heptanediol to 7-hydroxyheptanal using a polypeptide having the activity of an alcohol dehydrogenase classified, for example, under EC 1.1.1.- (e.g., EC 1.1.1.1, EC 1.1.1.2, EC 1.1.1.21, or EC 1.1.1.184) such as the gene product of YMR318C or YqhD or the protein having GenBank Accession No. CAA81612.1; followed by conversion to 7-aminoheptanol by a polypeptide having the activity of a ω-transaminase classified, for example, under EC 2.6.1.18, EC 2.6.1.19, EC 2.6.1.29, EC 2.6.1.48, or EC 2.6.1.82 such as SEQ ID NOs:7-12, followed by conversion to 7-aminoheptanal by a polypeptide having the activity of an alcohol dehydrogenase classified, for example, under EC 1.1.1.- (e.g., EC 1.1.1.1, EC 1.1.1.2, EC 1.1.1.21, or EC 1.1.1.184) such as the gene product of YMR318C or YqhD or the protein having GenBank Accession No. CAA81612.1, followed by conversion to heptamethylenediamine by a polypeptide having the activity of a ω-transaminase classified, for example, under EC 2.6.1.18, EC 2.6.1.19, EC 2.6.1.29, EC 2.6.1.48, or EC 2.6.1.82 such as SEQ ID NOs:7-12. See FIG. 5E.

Pathways Using 7-Hydroxyheptanoate as Central Precursor to 1,7-Heptanediol

In some embodiments, 1,7 heptanediol is synthesized from the central precursor, 7-hydroxyheptanoate, by conversion of 7-hydroxyheptanoate to 7-hydroxyheptanal by a polypeptide having the activity of a carboxylate reductase classified, for example, under EC 1.2.99.6 such as the gene product of car (see above, e.g., SEQ ID NO: 2, 3, 4, 5, 6 or 15) in combination with a phosphopantetheine transferase enhancer (e.g., encoded by a sfp gene from *Bacillus subtilis* or npt gene from *Nocardia*) or the gene products of GriC and GriD from *Streptomyces griseus* (Suzuki et al., J. Antibiot., 2007, 60(6), 380-387); followed by conversion of 7-hydroxyheptanal to 1,7 heptanediol by a polypeptide having the activity of an alcohol dehydrogenase (classified, for example, under EC 1.1.1.- such as EC 1.1.1.1, EC 1.1.1.2, EC 1.1.1.21, or EC 1.1.1.184) such as the gene product of YMR318C or YqhD (from *E. coli*, GenBank Accession No. AAA69178.1) (see, e.g., Liu et al., *Microbiology*, 2009, 155, 2078-2085; Larroy et al., 2002, Biochem J., 361(Pt 1), 163-172; or Jarboe, 2011, Appl. Microbiol. Biotechnol., 89(2), 249-257) or the protein having GenBank Accession No. CAA81612.1 (from *Geobacillus stearothermophilus*). See, FIG. 7.

Cultivation Strategy

In some embodiments, one or more C7 building blocks are biosynthesized in a recombinant microorganism using anaerobic, aerobic or micro-aerobic cultivation conditions. In some embodiments, the cultivation strategy entails nutrient limitation such as nitrogen, phosphate or oxygen limitation.

In some embodiments, a cell retention strategy using, for example, ceramic hollow fiber membranes can be employed to achieve and maintain a high cell density during either fed-batch or continuous fermentation.

In some embodiments, the principal carbon source fed to the fermentation in the synthesis of one or more C7 building blocks can derive from biological or non-biological feedstocks.

In some embodiments, the biological feedstock can be or can derive from, monosaccharides, disaccharides, lignocellulose, hemicellulose, cellulose, lignin, levulinic acid and formic acid, triglycerides, glycerol, fatty acids, agricultural waste, condensed distillers' solubles, or municipal waste.

The efficient catabolism of crude glycerol stemming from the production of biodiesel has been demonstrated in several microorganisms such as *Escherichia coli, Cupriavidus necator, Pseudomonas oleavorans, Pseudomonas putida* and *Yarrowia lypolytica* (Lee et al., *Appl. Biochem. Biotechnol.*, 2012, 166:1801-1813; Yang et al., *Biotechnology for Biofuels*, 2012, 5:13; Meijnen et al., *Appl. Microbiol. Biotechnol.*, 2011, 90:885-893).

The efficient catabolism of lignocellulosic-derived levulinic acid has been demonstrated in several organisms such as *Cupriavidus* necator and *Pseudomonas putida* in the synthesis of 3-hydroxyvalerate via the precursor propanoyl-CoA (Jaremko and Yu, 2011, supra; Martin and Prather, *J. Biotechnol.*, 2009, 139:61-67).

The efficient catabolism of lignin-derived aromatic compounds such as benzoate analogues has been demonstrated in several microorganisms such as *Pseudomonas putida, Cupriavidus* necator (Bugg et al., *Current Opinion in Bio-* technology, 2011, 22, 394-400; Perez-Pantoja et al., *FEMS Microbiol. Rev.,* 2008, 32, 736-794).

The efficient utilization of agricultural waste, such as olive mill waste water has been demonstrated in several microorganisms, including *Yarrowia lypolytica* (Papanikolaou et al., *Bioresour. Technol.,* 2008, 99(7):2419-2428).

The efficient utilization of fermentable sugars such as monosaccharides and disaccharides derived from cellulosic, hemicellulosic, cane and beet molasses, cassava, corn and other agricultural sources has been demonstrated for several microorganism such as *Escherichia coli, Corynebacterium glutamicum* and *Lactobacillus delbrueckii* and *Lactococcus lactis* (see, e.g., Hermann et al, *J. Biotechnol.,* 2003, 104: 155-172; Wee et al., *Food Technol. Biotechnol.,* 2006, 44(2):163-172; Ohashi et al., *J. Bioscience and Bioengineering,* 1999, 87(5):647-654).

The efficient utilization of furfural, derived from a variety of agricultural lignocellulosic sources, has been demonstrated for *Cupriavidus* necator (Li et al., *Biodegradation,* 2011, 22:1215-1225).

In some embodiments, the non-biological feedstock can be or can derive from natural gas, syngas, $CO_2/H_2$, methanol, ethanol, benzoate, non-volatile residue (NVR) or a caustic wash waste stream from cycloheptane oxidation processes, or terephthalic acid/isophthalic acid mixture waste streams.

The efficient catabolism of methanol has been demonstrated for the methylotrophic yeast *Pichia pastoris.*

The efficient catabolism of ethanol has been demonstrated for *Clostridium kluyveri* (Seedorf et al., *Proc. Natl. Acad. Sci. USA,* 2008, 105(6) 2128-2133).

The efficient catabolism of $CO_2$ and $H_2$, which may be derived from natural gas and other chemical and petrochemical sources, has been demonstrated for *Cupriavidus* necator (Prybylski et al., *Energy, Sustainability and Society,* 2012, 2:11).

The efficient catabolism of syngas has been demonstrated for numerous microorganisms, such as *Clostridium ljungdahlii* and *Clostridium autoethanogenum* (Köpke et al., *Applied and Environmental Microbiology,* 2011, 77(15): 5467-5475).

The efficient catabolism of the non-volatile residue waste stream from cycloheptane processes has been demonstrated for numerous microorganisms, such as *Delftia acidovorans* and *Cupriavidus* necator (Ramsay et al., *Applied and Environmental Microbiology,* 1986, 52(1):152-156).

In some embodiments, the microorganism is a prokaryote. For example, the prokaryote can be a bacterium from the genus *Escherichia* such as *Escherichia coli;* from the genus *Clostridia* such as *Clostridium ljungdahlii, Clostridium autoethanogenum* or *Clostridium kluyveri;* from the genus *Corynebacteria* such as *Corynebacterium glutamicum;* from the genus *Cupriavidus* such as *Cupriavidus* necator or *Cupriavidus metallidurans;* from the genus *Pseudomonas* such as *Pseudomonas fluorescens, Pseudomonas putida* or *Pseudomonas oleavorans;* from the genus *Delftia* such as *Delftia acidovorans;* from the genus *Bacillus* such as *Bacillus subtillis;* from the genus *Lactobacillus* such as *Lactobacillus delbrueckii;* or from the genus *Lactococcus* such as *Lactococcus lactis.* Such prokaryotes also can be a source of genes to construct recombinant cells described herein that are capable of producing one or more C7 building blocks.

In some embodiments, the microorganism is a eukaryote. For example, the eukaryote can be a filamentous fungus, e.g., one from the genus *Aspergillus* such as *Aspergillus niger.* Alternatively, the eukaryote can be a yeast, e.g., one from the genus *Saccharomyces* such as *Saccharomyces cerevisiae;* from the genus *Pichia* such as *Pichia pastoris;* or from the genus *Yarrowia* such as *Yarrowia lipolytica;* from the genus *Issatchenkia* such as *Issathenkia orientalis;* from the genus *Debaryomyces* such as *Debaryomyces hansenii;* from the genus *Arxula* such as *Arxula adenoinivorans;* or from the genus *Kluyveromyces* such as *Kluyveromyces lactis.* Such eukaryotes also can be a source of genes to construct recombinant cells described herein that are capable of producing one or more C7 building blocks.

Metabolic Engineering

The present document provides methods involving less than all the steps described for all the above pathways. Such methods can involve, for example, one, two, three, four, five, six, seven, eight, nine, ten, eleven, twelve or more of such steps. Where less than all the steps are included in such a method, the first, and in some embodiments the only, step can be any one of the steps listed.

Furthermore, recombinant microorganisms described herein can include any combination of the above enzymes such that one or more of the steps, e.g., one, two, three, four, five, six, seven, eight, nine, ten, or more of such steps, can be performed within a recombinant microorganism. This document provides recombinant cells of any of the genera and species listed and genetically engineered to express one or more (e.g., two, three, four, five, six, seven, eight, nine, 10, 11, 12 or more) recombinant forms of any of the enzymes recited in the document. Thus, for example, the recombinant cells can contain exogenous nucleic acids encoding enzymes catalyzing one or more of the steps of any of the pathways described herein.

In addition, this document recognizes that where enzymes have been described as accepting CoA-activated substrates, analogous enzyme activities associated with [acp]-bound substrates exist that are not necessarily in the same enzyme class.

Also, this document recognizes that where enzymes have been described accepting (R)-enantiomers of substrate, analogous enzyme activities associated with (S)-enantiomer substrates exist that are not necessarily in the same enzyme class.

This document also recognizes that where an enzyme is shown to accept a particular co-factor, such as NADPH, or co-substrate, such as acetyl-CoA, many enzymes are promiscuous in terms of accepting a number of different co-factors or co-substrates in catalyzing a particular enzyme activity. Also, this document recognizes that where enzymes have high specificity for e.g., a particular co-factor such as NADH, an enzyme with similar or identical activity that has high specificity for the co-factor NADPH may be in a different enzyme class.

In some embodiments, the enzymes in the pathways outlined herein are the result of enzyme engineering via non-direct or rational enzyme design approaches with aims of improving activity, improving specificity, reducing feedback inhibition, reducing repression, improving enzyme solubility, changing stereo-specificity, or changing ω-factor specificity.

In some embodiments, the enzymes in the pathways outlined here can be gene dosed, i.e., overexpressed, into the resulting genetically modified organism via episomal or chromosomal integration approaches.

In some embodiments, genome-scale system biology techniques such as Flux Balance Analysis can be utilized to devise genome scale attenuation or knockout strategies for directing carbon flux to a C7 building block.

Attenuation strategies include, but are not limited to; the use of transposons, homologous recombination (double cross-over approach), mutagenesis, enzyme inhibitors and RNAi interference.

In some embodiments, fluxomic, metabolomic and transcriptomal data can be utilized to inform or support genome-scale system biology techniques, thereby devising genome scale attenuation or knockout strategies in directing carbon flux to a C7 building block.

In some embodiments, the microorganism's tolerance to high concentrations of a C7 building block can be improved through continuous cultivation in a selective environment.

In some embodiments, the microorganism's endogenous biochemical network can be attenuated or augmented to (1) ensure the intracellular availability of acetyl-CoA and β-alanine, (2) create an NADH or NADPH imbalance that may only be balanced via the formation of one or more C7 building blocks, (3) prevent degradation of central metabolites, central precursors leading to and including one or more C7 building blocks and/or (4) ensure efficient efflux from the cell.

In some embodiments requiring intracellular availability of acetyl-CoA for C7 building block synthesis, endogenous enzymes catalyzing the hydrolysis of acetyl-CoA such as short-chain length thioesterases can be attenuated in the microorganism.

In some embodiments requiring the intracellular availability of acetyl-CoA for C7 building block synthesis, an endogenous phosphotransacetylase generating acetate such as pta can be attenuated (Shen et al., *Appl. Environ. Microbiol.*, 2011, 77(9):2905-2915).

In some embodiments requiring the intracellular availability of acetyl-CoA for C7 building block synthesis, an endogenous gene in an acetate synthesis pathway encoding an acetate kinase, such as ack, can be attenuated.

In some embodiments requiring the intracellular availability of acetyl-CoA and NADH for C7 building block synthesis, an endogenous gene encoding an enzyme that catalyzes the degradation of pyruvate to lactate such as lactate dehydrogenase encoded by ldhA can be attenuated (Shen et al., 2011, supra).

In some embodiments, enzymes that catalyze anapleurotic reactions such as PEP carboxylase and/or pyruvate carboxylase can be overexpressed in the microorganism.

In some embodiments requiring the intracellular availability of acetyl-CoA and NADH for C7 building block synthesis, endogenous genes encoding enzymes, such as menaquinol-fumarate oxidoreductase, that catalyze the degradation of phophoenolpyruvate to succinate such as frdBC can be attenuated (see, e.g., Shen et al., 2011, supra).

In some embodiments requiring the intracellular availability of acetyl-CoA and NADH for C7 building block synthesis, an endogenous gene encoding an enzyme that catalyzes the degradation of acetyl-CoA to ethanol such as the alcohol dehydrogenase encoded by adhE can be attenuated (Shen et al., 2011, supra).

In some embodiments, where pathways require excess NADH co-factor for C7 building block synthesis, a recombinant formate dehydrogenase gene can be overexpressed in the microorganism (Shen et al., 2011, supra).

In some embodiments, where pathways require excess NADH co-factor for C7 building block synthesis, a recombinant NADH-consuming transhydrogenase can be attenuated.

In some embodiments, an endogenous gene encoding an enzyme that catalyzes the degradation of pyruvate to ethanol such as pyruvate decarboxylase can be attenuated.

In some embodiments requiring the intracellular availability of acetyl-CoA for C7 building block synthesis, a recombinant acetyl-CoA synthetase such as the gene product of acs can be overexpressed in the microorganism (Satoh et al., *J. Bioscience and Bioengineering*, 2003, 95(4):335-341).

In some embodiments, carbon flux can be directed into the pentose phosphate cycle to increase the supply of NADPH by attenuating an endogenous glucose-6-phosphate isomerase (EC 5.3.1.9).

In some embodiments, carbon flux can be redirected into the pentose phosphate cycle to increase the supply of NADPH by overexpression a 6-phosphogluconate dehydrogenase and/or a transketolase (Lee et al., 2003, *Biotechnology Progress*, 19(5), 1444-1449).

In some embodiments, where pathways require excess NADPH co-factor in the synthesis of a C7 building block, a gene such as UdhA encoding a puridine nucleotide transhydrogenase can be overexpressed in the microorganism (Brigham et al., *Advanced Biofuels and Bioproducts*, 2012, Chapter 39, 1065-1090).

In some embodiments, where pathways require excess NADPH co-factor in the synthesis of a C7 Building Block, a recombinant glyceraldehyde-3-phosphate-dehydrogenase gene such as GapN can be overexpressed in the microorganisms (Brigham et al., 2012, supra).

In some embodiments, where pathways require excess NADPH co-factor in the synthesis of a C7 building block, a recombinant malic enzyme gene such as maeA or maeB can be overexpressed in the microorganisms (Brigham et al., 2012, supra).

In some embodiments, where pathways require excess NADPH co-factor in the synthesis of a C7 building block, a recombinant glucose-6-phosphate dehydrogenase gene such as zwf can be overexpressed in the microorganisms (Lim et al., *J. Bioscience and Bioengineering*, 2002, 93(6), 543-549).

In some embodiments, where pathways require excess NADPH co-factor in the synthesis of a C7 building block, a recombinant fructose 1,6 diphosphatase gene such as fbp can be overexpressed in the microorganisms (Becker et al., *J. Biotechnol.*, 2007, 132:99-109).

In some embodiments, where pathways require excess NADPH co-factor in the synthesis of a C7 building block, endogenous triose phosphate isomerase (EC 5.3.1.1) can be attenuated.

In some embodiments, where pathways require excess NADPH co-factor in the synthesis of a C7 building block, a recombinant glucose dehydrogenase such as the gene product of gdh can be overexpressed in the microorganism (Satoh et al., *J. Bioscience and Bioengineering*, 2003, 95(4): 335-341).

In some embodiments, endogenous enzymes facilitating the conversion of NADPH to NADH can be attenuated, such as the NADH generation cycle that may be generated via inter-conversion of glutamate dehydrogenases classified under EC 1.4.1.2 (NADH-specific) and EC 1.4.1.4 (NADPH-specific).

In some embodiments, an endogenous glutamate dehydrogenase (EC 1.4.1.3) that utilizes both NADH and NADPH as co-factors can be attenuated.

In some embodiments, a membrane-bound cytochrome P450 such as CYP4F3B can be solubilized by only expressing the cytosolic domain and not the N-terminal region that anchors the P450 to the endoplasmic reticulum (Scheller et al., *J. Biol. Chem.*, 1994, 269(17): 12779-12783).

In some embodiments, an enoyl-CoA reductase can be solubilized via expression as a fusion protein with a small soluble protein, for example, the maltose binding protein (Gloerich et al., *FEBS Letters*, 2006, 580, 2092-2096).

In some embodiments using microorganisms that naturally accumulate polyhydroxyalkanoates, the endogenous polymer synthase enzymes can be attenuated in the microorganism.

In some embodiments, a L-alanine dehydrogenase can be overexpressed in the microorganism to regenerate L-alanine from pyruvate as an amino donor for ω-transaminase reactions.

In some embodiments, a L-glutamate dehydrogenase, a L-glutamine synthetase, or a alpha-aminotransaminase can be overexpressed in the microorganism to regenerate L-glutamate from 2-oxoglutarate as an amino donor for ω-transaminase reactions.

In some embodiments, enzymes such as a pimeloyl-CoA dehydrogenase classified under, EC 1.3.1.62; an acyl-CoA dehydrogenase classified, for example, under EC 1.3.8.7, EC 1.3.8.1, or EC 1.3.99.-; and/or a butyryl-CoA dehydrogenase classified, for example, under EC 1.3.8.6 that degrade central metabolites and central precursors leading to and including C7 building blocks can be attenuated.

In some embodiments, endogenous enzymes activating C7 building blocks via Coenzyme A esterification such as CoA-ligases (e.g., an adipyl-CoA synthetase) classified under, for example, EC 6.2.1.- can be attenuated.

In some embodiments, the efflux of a C7 building block across the cell membrane to the extracellular media can be enhanced or amplified by genetically engineering structural modifications to the cell membrane or increasing any associated transporter activity for a C7 building block.

The efflux of heptamethylenediamine can be enhanced or amplified by overexpressing broad substrate range multidrug transporters such as Blt from *Bacillus subtilis* (Woolridge et al., 1997, 1 *Biol. Chem.*, 272(14):8864-8866); AcrB and AcrD from *Escherichia coli* (Elkins & Nikaido, 2002, *J Bacteriol.*, 184(23), 6490-6499), NorA from *Staphylococcus aereus* (Ng et al., 1994, *Antimicrob Agents Chemother*, 38(6), 1345-1355), or Bmr from *Bacillus subtilis* (Neyfakh, 1992, *Antimicrob Agents Chemother*, 36(2), 484-485).

The efflux of 7-aminoheptanoate and heptamethylenediamine can be enhanced or amplified by overexpressing the solute transporters such as the lysE transporter from *Corynebacterium glutamicum* (Bellmann et al., 2001, *Microbiology*, 147, 1765-1774).

The efflux of pimelic acid can be enhanced or amplified by overexpressing a dicarboxylate transporter such as the SucE transporter from *Corynebacterium glutamicum* (Huhn et al., *Appl. Microbiol. & Biotech.*, 89(2), 327-335).

Producing C7 Building Blocks Using a Recombinant Microorganism

Typically, one or more C7 building blocks can be produced by providing a microorganism and culturing the provided microorganism with a culture medium containing a suitable carbon source as described above. In general, the culture media and/or culture conditions can be such that the microorganisms grow to an adequate density and produce a C7 building block efficiently. For large-scale production processes, any method can be used such as those described elsewhere (Manual of Industrial Microbiology and Biotechnology, 2$^{nd}$ Edition, Editors: A. L. Demain and J. E. Davies, ASM Press; and Principles of Fermentation Technology, P. F. Stanbury and A. Whitaker, Pergamon). Briefly, a large tank (e.g., a 100 gallon, 200 gallon, 500 gallon, or more tank) containing an appropriate culture medium is inoculated with a particular microorganism. After inoculation, the microorganism is incubated to allow biomass to be produced. Once a desired biomass is reached, the broth containing the microorganisms can be transferred to a second tank. This second tank can be any size. For example, the second tank can be larger, smaller, or the same size as the first tank. Typically, the second tank is larger than the first such that additional culture medium can be added to the broth from the first tank. In addition, the culture medium within this second tank can be the same as, or different from, that used in the first tank.

Once transferred, the microorganisms can be incubated to allow for the production of a C7 building block. Once produced, any method can be used to isolate C7 building blocks. For example, C7 building blocks can be recovered selectively from the fermentation broth via adsorption processes. In the case of pimelic acid and 7-aminoheptanoic acid, the resulting eluate can be further concentrated via evaporation, crystallized via evaporative and/or cooling crystallization, and the crystals recovered via centrifugation. In the case of heptamethylenediamine and 1,7-heptanediol, distillation may be employed to achieve the desired product purity.

The invention will be further described in the following examples, which do not limit the scope of the invention described in the claims.

EXAMPLES

Example 1

Enzyme Activity of ω-Transaminase Using Pimelate Semialdehyde as Substrate and Forming 7-Aminoheptanoate A nucleotide sequence encoding an N-terminal His-tag was added to the nucleic acid sequences from *Chromobacterium violaceum*, *Pseudomonas syringae*, *Rhodobacter sphaeroides*, and *Vibrio fluvialis* encoding the ω-transaminases of SEQ ID NOs: 7, 9, 10 and 12, respectively (see FIG. 8C and FIG. 8D) such that N-terminal HIS tagged ω-transaminases could be produced. Each of the resulting modified genes was cloned into a pET21a expression vector under control of the T7 promoter and each expression vector was transformed into a BL21[DE3] *E. coli* strain. The resulting recombinant *E. coli* strains were cultivated at 37° C. in a 250 mL shake flask culture containing 50 mL LB media and antibiotic selection pressure, with shaking at 230 rpm. Each culture was induced overnight at 16° C. using 1 mM IPTG.

The pellet from each induced shake flask culture was harvested via centrifugation. Each pellet was resuspended and lysed via sonication. The cell debris was separated from the supernatant via centrifugation and the cell free extract was used immediately in enzyme activity assays.

Enzyme activity assays in the reverse direction (i.e., 7-aminoheptanoate to pimelate semialdehyde) were performed in a buffer composed of a final concentration of 50 mM HEPES buffer (pH=7.5), 10 mM 7-aminoheptanoate, 10 mM pyruvate and 100 μM pyridoxyl 5' phosphate. Each enzyme activity assay reaction was initiated by adding cell free extract of the ω-transaminase gene product or the empty vector control to the assay buffer containing the 7-aminoheptanoate and incubated at 25° C. for 4 h, with shaking at 250 rpm. The formation of L-alanine from pyruvate was quantified via RP-HPLC.

Figure 14:
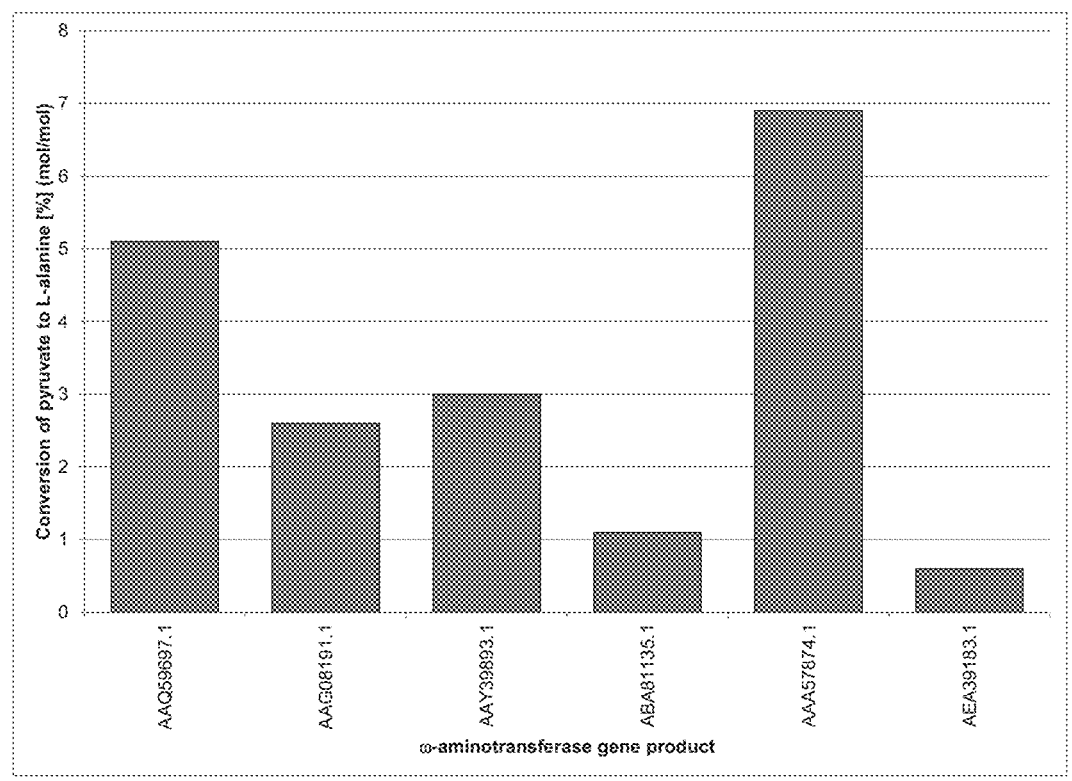
FIG. 14 is a bar graph summarizing the percent conversion of pyruvate to L-alanine (mol/mol) as a measure of the ω-transaminase activity of the enzyme only controls (no substrate).
Figure 15:
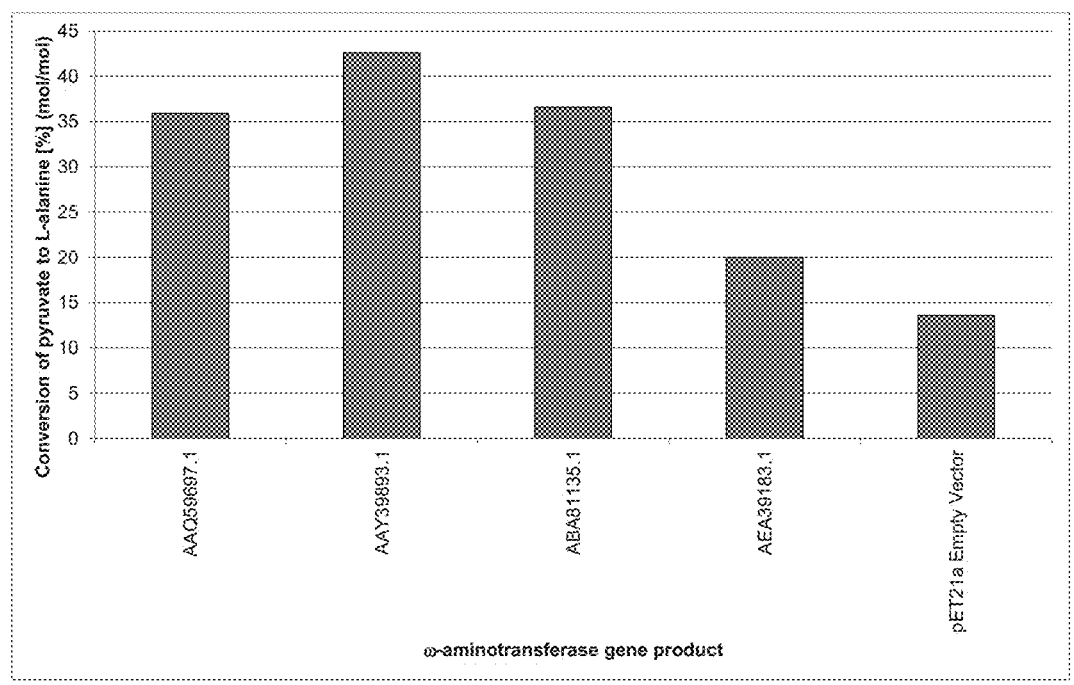
FIG. 15 is a bar graph of the percent conversion after 4 hours of pyruvate to L-alanine (mol/mol) as a measure of the ω-transaminase activity of four ω-transaminase preparations for converting 7-aminoheptanoate to pimelate semialdehyde relative to the empty vector control.

Each enzyme only control without 7-aminoheptanoate demonstrated low base line conversion of pyruvate to L-alanine. See FIG. 14. The gene product of SEQ ID NO 7, SEQ ID NO 9, SEQ ID NO 10 and SEQ ID NO 12 accepted 7-aminoheptanote as substrate as confirmed against the empty vector control. See FIG. 15.

Enzyme activity in the forward direction (i.e., pimelate semialdehyde to 7-aminoheptanoate) was confirmed for the transaminases of SEQ ID NO 9, SEQ ID NO 10 and SEQ ID NO 12. Enzyme activity assays were performed in a buffer composed of a final concentration of 50 mM HEPES buffer (pH=7.5), 10 mM pimelate semialdehyde, 10 mM L-alanine and 100 µM pyridoxyl 5' phosphate. Each enzyme activity assay reaction was initiated by adding a cell free extract of the ω-transaminase gene product or the empty vector control to the assay buffer containing the pimelate semialdehyde and incubated at 25° C. for 4 h, with shaking at 250 rpm. The formation of pyruvate was quantified via RP-HPLC.

Figure 16:
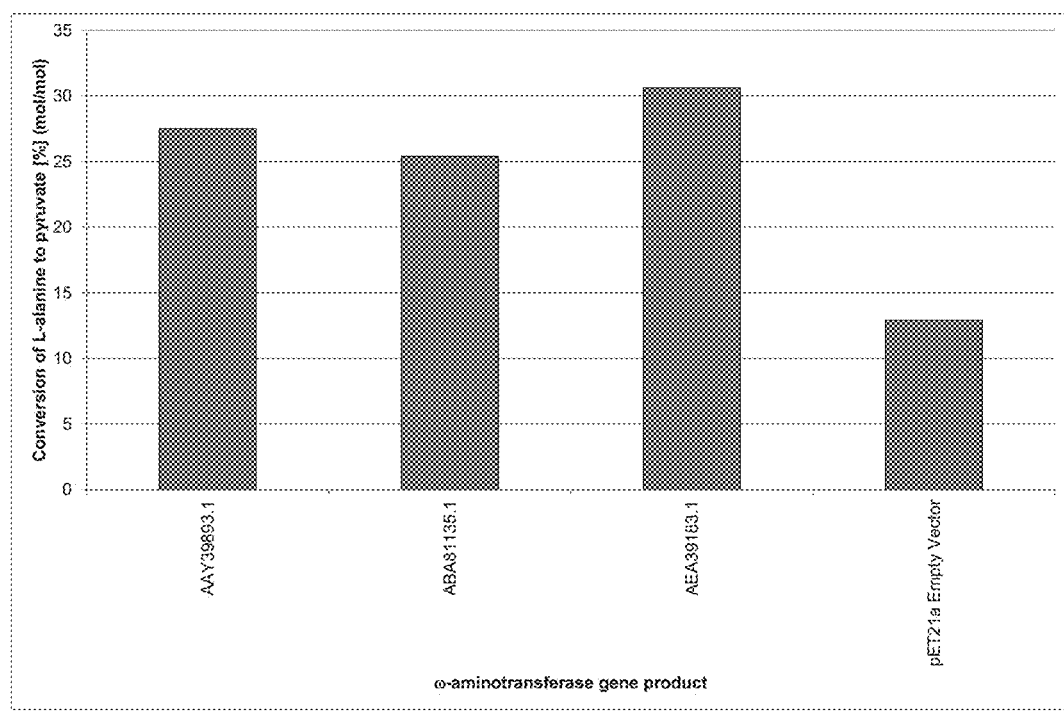
FIG. 16 is a bar graph of the percent conversion after 4 hours of L-alanine to pyruvate (mol/mol) as a measure of the ω-transaminase activity of three ω-transaminase preparations for converting pimelate semialdehyde to 7-aminoheptanoate relative to the empty vector control.

The gene product of SEQ ID NO 9, SEQ ID NO 10 and SEQ ID NO 12 accepted pimelate semialdehyde as substrate as confirmed against the empty vector control. See FIG. 16. The reversibility of the ω-transaminase activity was confirmed, demonstrating that the ω-transaminases of SEQ ID NO: 7, SEQ ID NO: 9, SEQ ID NO: 10, and SEQ ID NO: 12 accepted pimelate semialdehyde as substrate and synthesized 7-aminoheptanoate as a reaction product.

Example 2

Enzyme Activity of Carboxylate Reductase Using Pimelate as Substrate and Forming Pimelate Semialdehyde A nucleotide sequence encoding a HIS-tag was added to the nucleic acid sequences from *Segniliparus rugosus* and *Segniliparus rotundus* that encode the carboxylate reductases of SEQ ID NOs: 4 (EFV11917.1) and 6 (ADG98140.1), respectively (see FIG. 8B and FIG. 8C), such that N-terminal HIS tagged carboxylate reductases could be produced. Each of the modified genes was cloned into a pET Duet expression vector along with a sfp gene encoding a HIS-tagged phosphopantetheine transferase from *Bacillus subtilis*, both under the T7 promoter. Each expression vector was transformed into a BL21[DE3] *E. coli* strain and the resulting recombinant *E. coli* strains were cultivated at 37° C. in a 250 mL shake flask culture containing 50 mL LB media and antibiotic selection pressure, with shaking at 230 rpm. Each culture was induced overnight at 37° C. using an auto-induction media.

The pellet from each induced shake flask culture was harvested via centrifugation. Each pellet was resuspended and lysed via sonication, and the cell debris was separated from the supernatant via centrifugation. The carboxylate reductases and phosphopantetheine transferases were purified from the supernatant using Ni-affinity chromatography, diluted 10-fold into 50 mM HEPES buffer (pH=7.5), and concentrated via ultrafiltration.

Figure 9:
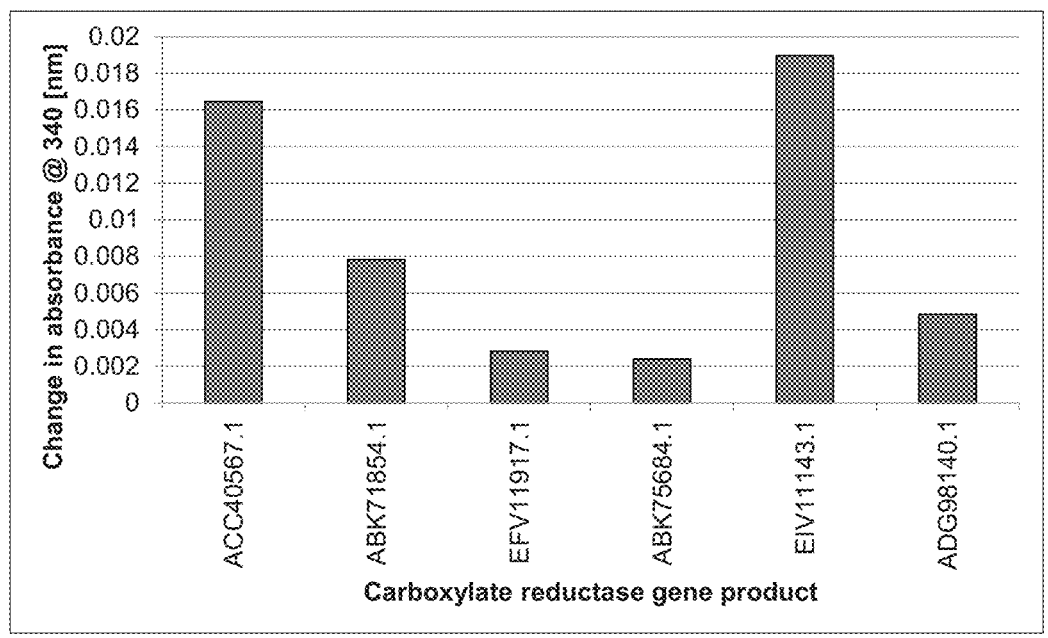
FIG. 9 is a bar graph summarizing the change in absorbance at 340 nm after 20 minutes, which is a measure of the consumption of NADPH and activity of six carboxylate reductase preparations in enzyme only controls (no substrate).

Enzyme activity assays (i.e., from pimelate to pimelate semialdehyde) were performed in triplicate in a buffer composed of a final concentration of 50 mM HEPES buffer (pH=7.5), 2 mM pimelate, 10 mM MgCl$_2$, 1 mM ATP and 1 mM NADPH. Each enzyme activity assay reaction was initiated by adding purified carboxylate reductase and phosphopantetheine transferase gene products or the empty vector control to the assay buffer containing the pimelate and then incubated at room temperature for 20 min. The consumption of NADPH was monitored by absorbance at 340 nm. Each enzyme only control without pimelate demonstrated low base line consumption of NADPH. See bars for EFV11917.1 and ADG98140.1 in FIG. 9.

Figure 10:
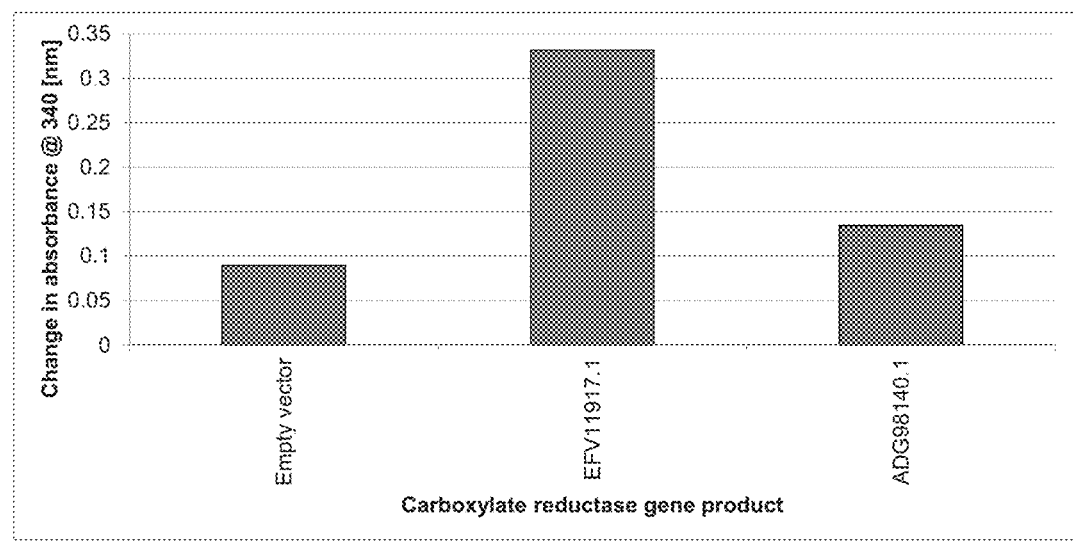
FIG. 10 is a bar graph of the change in absorbance at 340 nm after 20 minutes, which is a measure of the consumption of NADPH and the activity of two carboxylate reductase preparations for converting pimelate to pimelate semialdehyde relative to the empty vector control.

The gene products of SEQ ID NO: 4 (EFV11917.1) and SEQ ID NO: 6 (ADG98140.1), enhanced by the gene product of sfp, accepted pimelate as substrate, as confirmed against the empty vector control (see FIG. 10), and synthesized pimelate semialdehyde.

Example 3

Enzyme Activity of Carboxylate Reductase Using 7-Hydroxyheptanoate as Substrate and Forming 7-Hydroxyheptanal A nucleotide sequence encoding a His-tag was added to the nucleic acids from *Mycobacterium marinum*, *Mycobacterium smegmatis*, *Segnihparus rugosus*, *Mycobacterium smegmatis*, *Mycobacterium massiliense*, and *Segnihparus rotundus* that encode the carboxylate reductases of SEQ ID NOs: 2-6 and 15, respectively (GenBank Accession Nos. ACC40567.1, ABK71854.1, EFV11917.1, EIV11143.1, ADG98140.1, and ABK75684.1, respectively) (see FIG. 8A, FIG. 8B, FIG. 8C, and FIG. 8D) such that N-terminal HIS tagged carboxylate reductases could be produced. Each of the modified genes was cloned into a pET Duet expression vector alongside a sfp gene encoding a His-tagged phosphopantetheine transferase from *Bacillus subtilis*, both under control of the T7 promoter. Each expression vector was transformed into a BL21[DE3] *E. coli* strain along with the expression vectors from Example 3. Each resulting recombinant *E. coli* strain was cultivated at 37° C. in a 250 mL shake flask culture containing 50 mL LB media and antibiotic selection pressure, with shaking at 230 rpm. Each culture was induced overnight at 37° C. using an auto-induction media.

The pellet from each induced shake flask culture was harvested via centrifugation. Each pellet was resuspended and lysed via sonication. The cell debris was separated from the supernatant via centrifugation. The carboxylate reductases and phosphopantetheine transferase were purified from the supernatant using Ni-affinity chromatography, diluted 10-fold into 50 mM HEPES buffer (pH=7.5) and concentrated via ultrafiltration.

Enzyme activity (i.e., 7-hydroxyheptanoate to 7-hydroxyheptanal) assays were performed in triplicate in a buffer composed of a final concentration of 50 mM HEPES buffer (pH=7.5), 2 mM 7-hydroxyheptanal, 10 mM MgCl$_2$, 1 mM ATP, and 1 mM NADPH. Each enzyme activity assay reaction was initiated by adding purified carboxylate reductase and phosphopantetheine transferase or the empty vector control to the assay buffer containing the 7-hydroxyheptanoate and then incubated at room temperature for 20 min. The consumption of NADPH was monitored by absorbance at 340 nm. Each enzyme only control without 7-hydroxyheptanoate demonstrated low base line consumption of NADPH. See FIG. 9.

Figure 11:
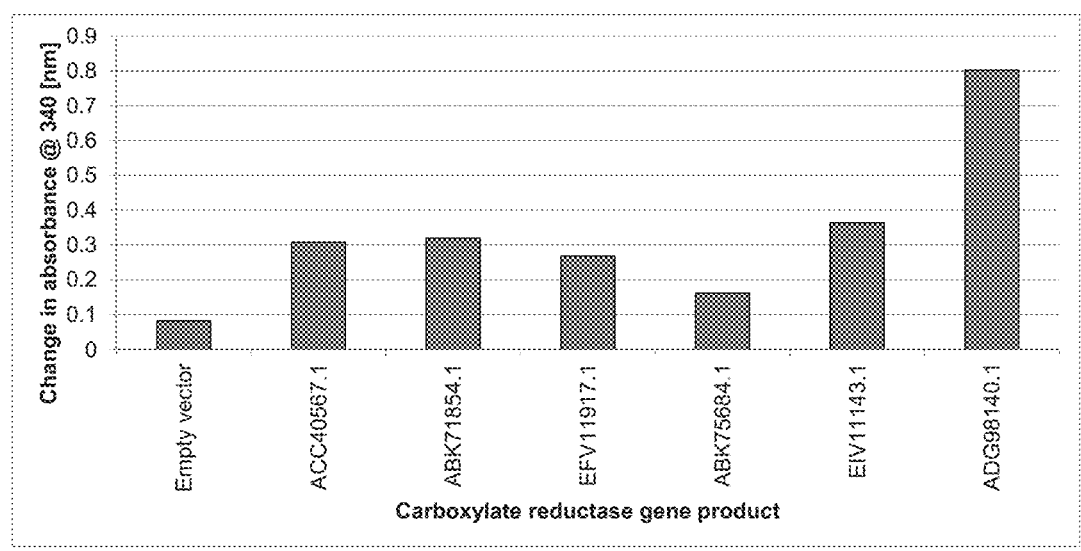
FIG. 11 is a bar graph of the change in absorbance at 340 nm after 20 minutes, which is a measure of the consumption of NADPH and the activity of six carboxylate reductase preparations for converting 7-hydroxyheptanoate to 7-hydroxyheptanal relative to the empty vector control.

The gene products of SEQ ID NO 2-6 and 15, enhanced by the gene product of sfp accepted 7-hydroxyheptanoate as substrate as confirmed against the empty vector control (see FIG. 11), and synthesized 7-hydroxyheptanal.

Example 4

Enzyme Activity of ω-Transaminase for 7-Aminoheptanol, Forming 7-Oxoheptanol

A nucleotide sequence encoding an N-terminal His-tag was added to the *Chromobacterium violaceum*, *Pseudomonas syringae* and *Rhodobacter sphaeroides* nucleic acids encoding the ω-transaminases of SEQ ID NOs: 7, 9 and 10, respectively (see FIG. 8C) such that N-terminal HIS tagged ω-transaminases could be produced. The modified genes were cloned into a pET21a expression vector under the T7 promoter. Each expression vector was transformed into a BL21[DE3] *E. coli* strain. Each resulting recombinant *E. coli* strain were cultivated at 37° C. in a 250 mL shake flask culture containing 50 mL LB media and antibiotic selection pressure, with shaking at 230 rpm. Each culture was induced overnight at 16° C. using 1 mM IPTG.

The pellet from each induced shake flask culture was harvested via centrifugation. Each pellet was resuspended and lysed via sonication. The cell debris was separated from the supernatant via centrifugation and the cell free extract was used immediately in enzyme activity assays.

Enzyme activity assays in the reverse direction (i.e., 7-aminoheptanol to 7-oxoheptanol) were performed in a buffer composed of a final concentration of 50 mM HEPES buffer (pH=7.5), 10 mM 7-aminoheptanol, 10 mM pyruvate, and 100 pyridoxyl 5' phosphate. Each enzyme activity assay reaction was initiated by adding cell free extract of the ω-transaminase gene product or the empty vector control to the assay buffer containing the 7-aminoheptanol and then incubated at 25° C. for 4 h, with shaking at 250 rpm. The formation of L-alanine was quantified via RP-HPLC.

Each enzyme only control without 7-aminoheptanol had low base line conversion of pyruvate to L-alanine. See FIG. 14.

Figure 19:
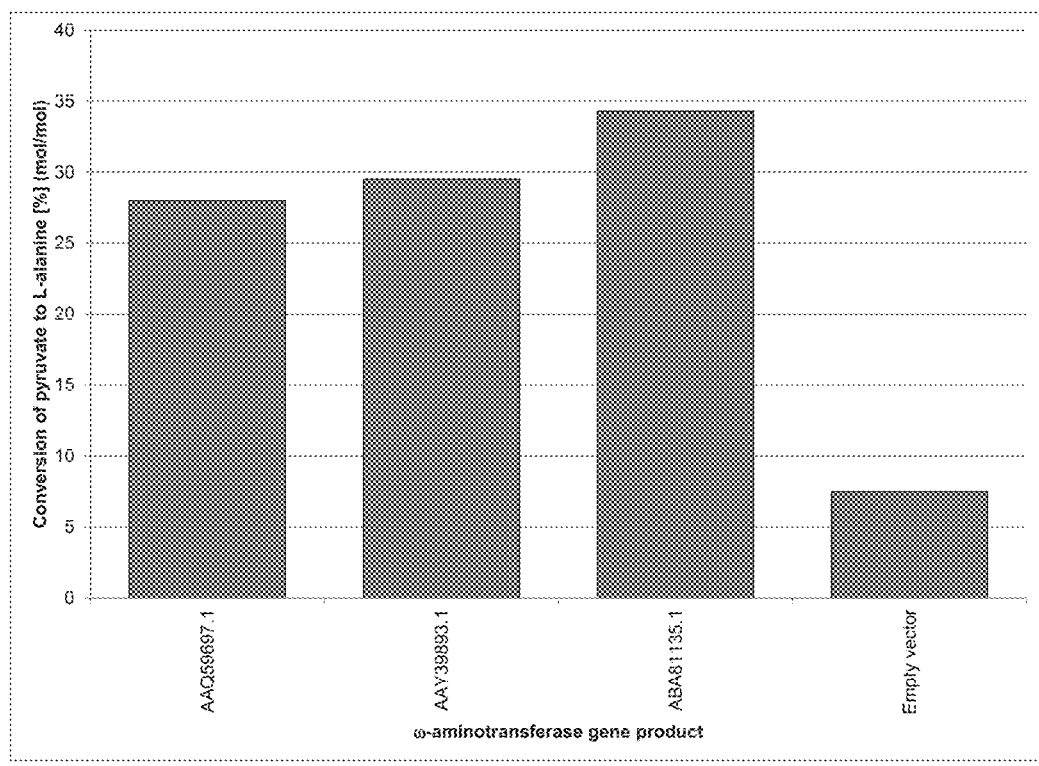
FIG. 19 is a bar graph of the percent conversion after 4 hours of pyruvate to L-alanine (mol/mol) as a measure of the ω-transaminase activity of three ω-transaminase preparations for converting 7-aminoheptanol to 7-oxoheptanol relative to the empty vector control.

The gene products of SEQ ID NOs: 7, 9 & 10 accepted 7-aminoheptanol as substrate as confirmed against the empty vector control (see FIG. 19) and synthesized 7-oxoheptanol as reaction product. Given the reversibility of the ω-transaminase activity (see Example 1), it can be concluded that the gene products of SEQ ID Nos: 7, 9 & 10 accept 7-oxoheptanol as substrate and form 7-aminoheptanol.

Example 5

Enzyme Activity of ω-Transaminase Using Heptamethylenediamine as Substrate and Forming 7-Aminoheptanal A nucleotide sequence encoding an N-terminal His-tag was added to the *Chromobacterium violaceum*, *Pseudomonas aeruginosa*, *Pseudomonas syringae*, *Rhodobacter sphaeroides*, *Escherichia coli*, and *Vibrio fluvialis* nucleic acids encoding the ω-transaminases of SEQ ID NOs: 7-12, respectively (see FIG. 8C and FIG. 8D) such that N-terminal HIS tagged ω-transaminases could be produced. The modified genes were cloned into a pET21a expression vector under the T7 promoter. Each expression vector was transformed into a BL21[DE3] *E. coli* strain. Each resulting recombinant *E. coli* strain were cultivated at 37° C. in a 250 mL shake flask culture containing 50 mL LB media and antibiotic selection pressure, with shaking at 230 rpm. Each culture was induced overnight at 16° C. using 1 mM IPTG.

The pellet from each induced shake flask culture was harvested via centrifugation. Each pellet was resuspended and lysed via sonication. The cell debris was separated from the supernatant via centrifugation and the cell free extract was used immediately in enzyme activity assays.

Enzyme activity assays in the reverse direction (i.e., heptamethylenediamine to 7-aminoheptanal) were performed in a buffer composed of a final concentration of 50 mM HEPES buffer (pH=7.5), 10 mM heptamethylenediamine, 10 mM pyruvate, and 100 pyridoxyl 5' phosphate. Each enzyme activity assay reaction was initiated by adding cell free extract of the ω-transaminase gene product or the empty vector control to the assay buffer containing the heptamethylenediamine and then incubated at 25° C. for 4 h, with shaking at 250 rpm. The formation of L-alanine was quantified via RP-HPLC.

Each enzyme only control without heptamethylenediamine had low base line conversion of pyruvate to L-alanine. See FIG. 14.

Figure 17:
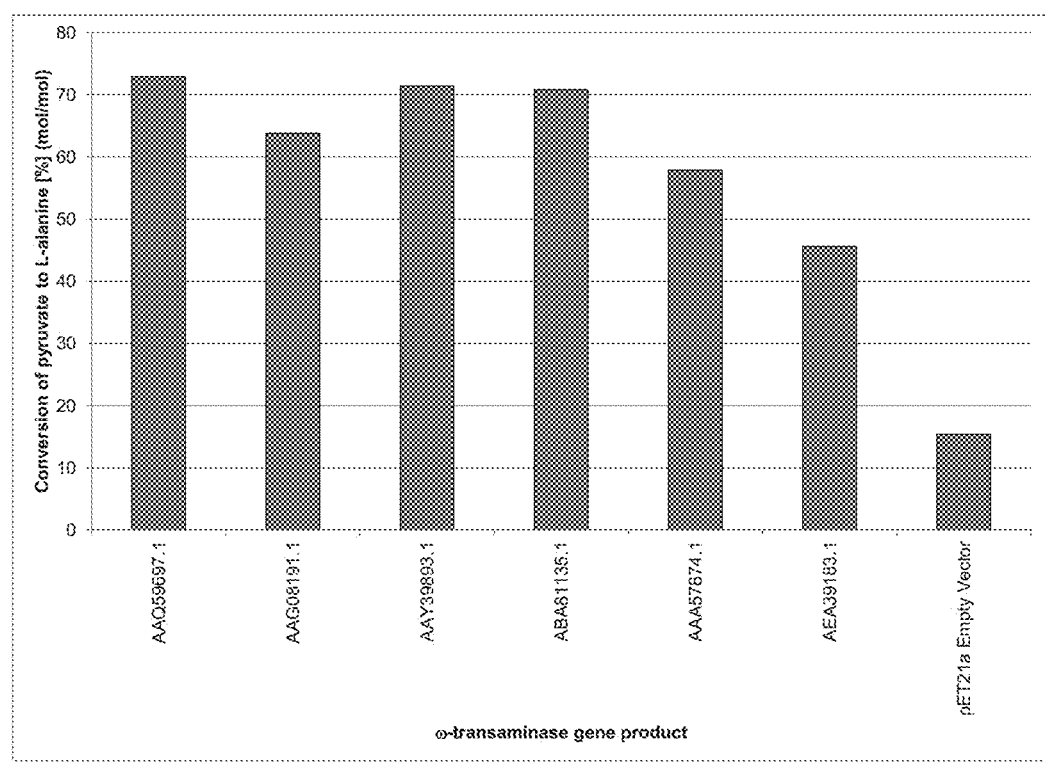
FIG. 17 is a bar graph of the percent conversion after 4 hours of pyruvate to L-alanine (mol/mol) as a measure of the ω-transaminase activity of six ω-transaminase preparations for converting heptamethylenediamine to 7-aminoheptanal relative to the empty vector control.

The gene products of SEQ ID NOs: 7-12 accepted heptamethylenediamine as substrate as confirmed against the empty vector control (see FIG. 17) and synthesized 7-aminoheptanal as reaction product. Given the reversibility of the ω-transaminase activity (see Example 1), it can be concluded that the gene products of SEQ ID NOs: 7-12 accept 7-aminoheptanal as substrate and form heptamethylenediamine.

Example 6

Enzyme Activity of Carboxylate Reductase for N7-Acetyl-7-Aminoheptanoate, Forming N7-Acetyl-7-Aminoheptanal The activity of each of the N-terminal His-tagged carboxylate reductases of SEQ ID NOs: 3, 5, and 6 (see Examples 2 and 3, and FIG. 8A, FIG. 8B, and FIG. 8C) for converting N7-acetyl-7-aminoheptanoate to N7-acetyl-7-aminoheptanal was assayed in triplicate in a buffer composed of a final concentration of 50 mM HEPES buffer (pH=7.5), 2 mM N7-acetyl-7-aminoheptanoate, 10 mM $MgCl_2$, 1 mM ATP, and 1 mM NADPH. The assays were initiated by adding purified carboxylate reductase and phosphopantetheine transferase or the empty vector control to the assay buffer containing the N7-acetyl-7-aminoheptanoate then incubated at room temperature for 20 min. The consumption of NADPH was monitored by absorbance at 340 nm. Each enzyme only control without N7-acetyl-7-aminoheptanoate demonstrated low base line consumption of NADPH. See FIG. 9.

Figure 12:
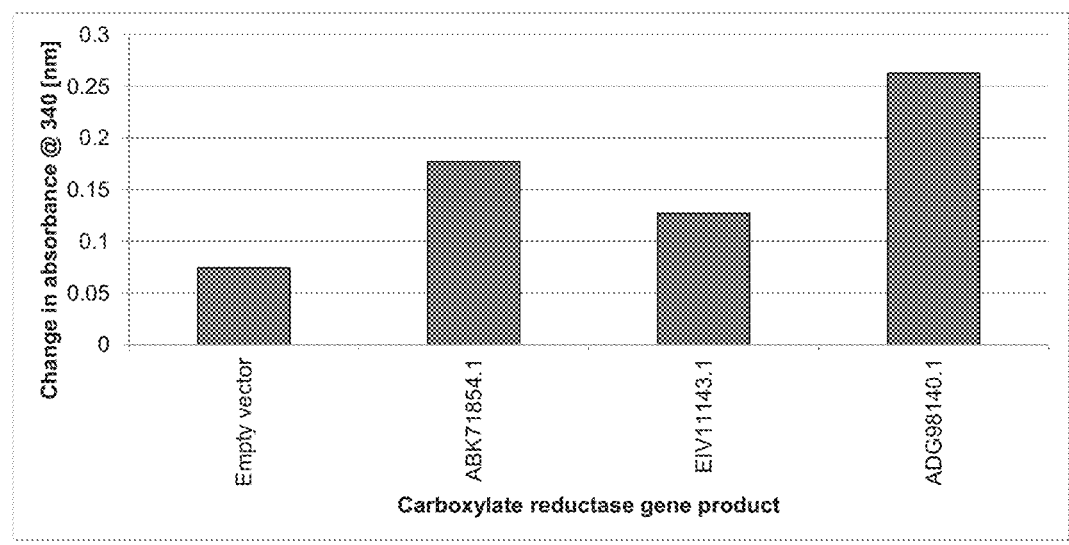
FIG. 12 is a bar graph of the change in absorbance at 340 nm after 20 minutes, which is a measure of the consumption of NADPH and the activity of three carboxylate reductase preparations for converting N7-acetyl-7-aminoheptanoate to N7-acetyl-7-aminoheptanal relative to the empty vector control.

The gene products of SEQ ID NO 3, 5, and 6, enhanced by the gene product of sfp, accepted N7-acetyl-7-aminoheptanoate as substrate as confirmed against the empty vector control (see FIG. 12), and synthesized N7-acetyl-7-aminoheptanal.

Example 7

Enzyme Activity of ω-Transaminase Using N7-Acetyl-1,7-Diaminoheptane, and Forming N7-Acetyl-7-Aminoheptanal The activity of the N-terminal His-tagged ω-transaminases of SEQ ID NOs: 7-12 (see Example 5, and FIG. 8C and FIG. 8D) for converting N7-acetyl-1,7-diaminoheptane to N7-acetyl-7-aminoheptanal was assayed using a buffer composed of a final concentration of 50 mM HEPES buffer (pH=7.5), 10 mM N7-acetyl-1,7-diaminoheptane, 10 mM pyruvate and 100 µM pyridoxyl 5' phosphate. Each enzyme activity assay reaction was initiated by adding a cell free extract of the ω-transaminase or the empty vector control to the assay buffer containing the N7-acetyl-1,7-diaminoheptane then incubated at 25° C. for 4 h, with shaking at 250 rpm. The formation of L-alanine was quantified via RP-HPLC.

Each enzyme only control without N7-acetyl-1,7-diaminoheptane demonstrated low base line conversion of pyruvate to L-alanine. See FIG. 14.

Figure 18:
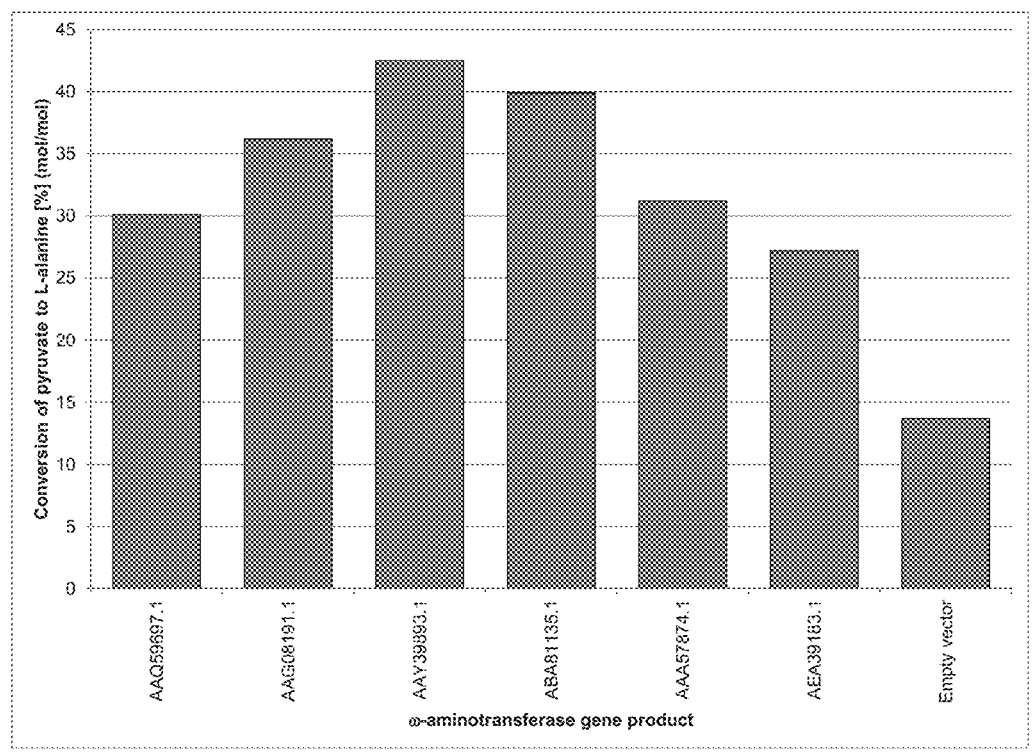
FIG. 18 is a bar graph of the percent conversion after 4 hours of pyruvate to L-alanine (mol/mol) as a measure of the ω-transaminase activity of six ω-transaminase preparations for converting N7-acetyl-1,7-diaminoheptane to N7-acetyl-7-aminoheptanal relative to the empty vector control.

The gene product of SEQ ID NOs: 7-12 accepted N7-acetyl-1,7-diaminoheptane as substrate as confirmed against the empty vector control (see FIG. 18) and synthesized N7-acetyl-7-aminoheptanal as reaction product.

Given the reversibility of the ω-transaminase activity (see Example 1), the gene products of SEQ ID NOs: 7-12 accept N7-acetyl-7-aminoheptanal as substrate forming N7-acetyl-1,7-diaminoheptane.

Example 8

Enzyme Activity of Carboxylate Reductase Using Pimelate Semialdehyde as Substrate and Forming Heptanedial The N-terminal His-tagged carboxylate reductase of SEQ ID NO: 6 (see Example 3 and FIG. 8C) was assayed using pimelate semialdehyde as substrate. The enzyme activity assay was performed in triplicate in a buffer composed of a final concentration of 50 mM HEPES buffer (pH=7.5), 2 mM pimelate semialdehyde, 10 mM $MgCl_2$, 1 mM ATP and 1 mM NADPH. The enzyme activity assay reaction was initiated by adding purified carboxylate reductase and phosphopantetheine transferase or the empty vector control to the assay buffer containing the pimelate semialdehyde and then incubated at room temperature for 20 min. The consumption of NADPH was monitored by absorbance at 340 nm. The enzyme only control without pimelate semialdehyde demonstrated low base line consumption of NADPH. See FIG. 9.

Figure 13:
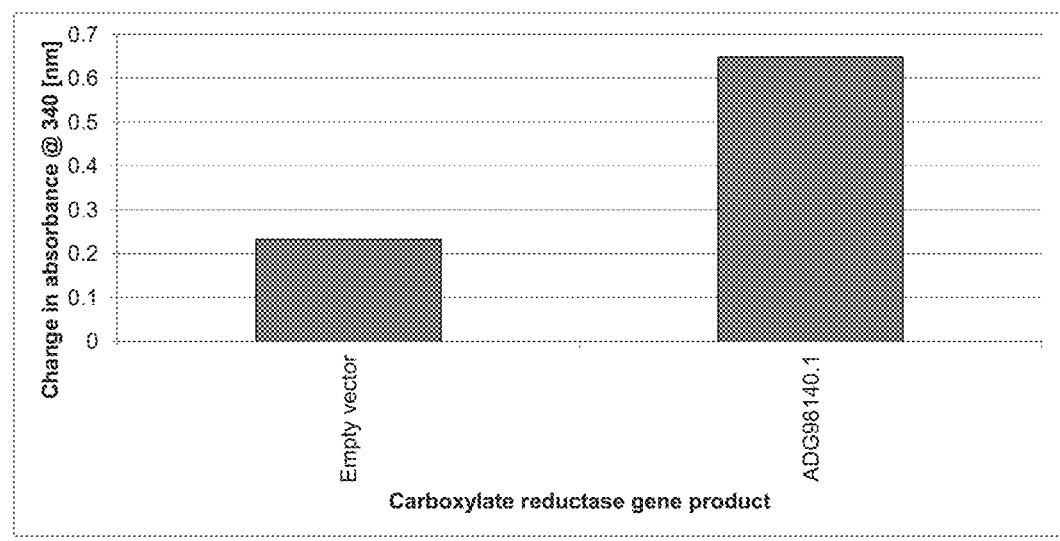
FIG. 13 is a bar graph of the change in absorbance at 340 nm after 20 minutes, which is a measure of the consumption of NADPH and activity of a carboxylate reductase preparation for converting pimelate semialdehyde to heptanedial relative to the empty vector control.

The gene product of SEQ ID N: 6, enhanced by the gene product of sfp, accepted pimelate semialdehyde as substrate as confirmed against the empty vector control (see FIG. 13) and synthesized heptanedial.

Example 9

Enzyme Activity of 4-Hydroxybutyrate-CoA Transferase Using β-Alanine as Substrate and Forming Using β-Alanyl-CoA and 5-Amino-3-Oxopentanoyl-CoA A nucleotide sequence encoding a His-tag was added to the nucleic acid sequences from *Cupriavidus necator*, *Clostridium propionicum*, *Clostridium aminobutyricum*, *Citrobacter* sp. A1, *Acetobacter aceti*, and *E. coli* K12 encoding, in sequential order, the β-ketothiolase, priopionate CoA-transferase, 4-hydroxybutyrate-CoA transferase, acetyl-CoA hydrolase, succinyl-CoA: acetate CoA-transferase, and thiolase of SEQ ID NOs: 16, 17, 18, 19, 20, and 21, respectively (see FIG. 7) for production of His-tagged versions of each protein. Each of the resulting modified genes was cloned into a pET21a expression vector under control of the T7 promoter and each expression vector was transformed into a BL21[DE3] *E. coli* strain. The resulting recombinant *E. coli* strains were cultivated at 37° C. in a 500 mL shake flask culture containing 100 mL LB media and antibiotic selection pressure, with shaking at 230 rpm. Each culture was induced overnight at 20° C. using 0.5 mM IPTG.

The pellet from each induced shake flask culture was harvested via centrifugation. Each pellet was resuspended and lysed via sonication, and the cell debris was separated from the supernatant via centrifugation and passage through a 0.45 µm filter. Each of the His-tagged proteins was purified from the supernatant by Ni-affinity chromatography, diluted 10-fold into 50 mM HEPES buffer (pH=7.5), and concentrated by centrifugal filtration with a cut-off of 10 kD.

Figure 20:
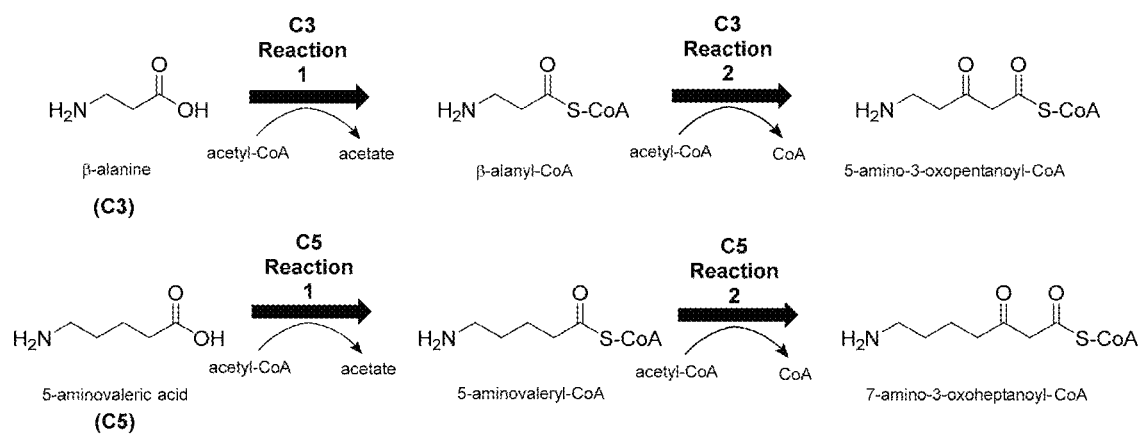
FIG. 20 is a schematic of the exemplary enzymatic reactions performed with 4-hydroxybutyrate-CoA transferase using either β-alanine (C3) or 5-aminovaleric acid (C5) as substrates for the formation of 5-amino-3-oxopentanoyl-CoA and 7-amino-3-oxoheptanoyl-CoA, respectively.
Figure 21:
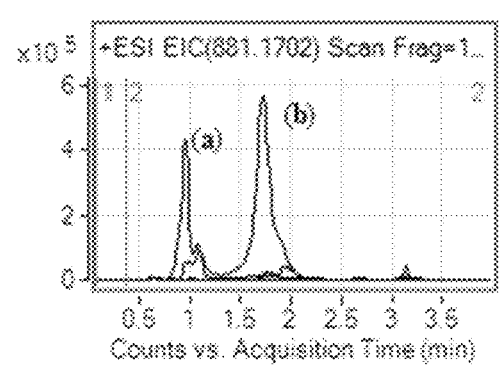
FIG. 21 is a LC-MS chromatogram of distinct peaks of chemical abundance separated by retention times as a measure of enzyme activity of 4-hydroxybutyrate-CoA transferase for converting β-alanine into β-alanine-CoA (a) and 5-amino-3-oxopentanoyl-CoA (b) products. Extracted chromatograms for [M+H] values 839.1596 (a) and 881.1702 (b).

Enzyme assays were monitored for two reaction steps for each substrate, β-alanine (C3) and 5-aminovaleric acid (C5): reaction 1 and reaction 2 (see FIG. 20 for reaction schematic). Each enzyme activity assay was performed in a buffer composed of a final concentration of 25 mM HEPES buffer (pH=7.5), 50 mM β-alanine (C3) or 50 mM 5-aminovaleric acid (C5), and 2 mM acetyl CoA. Each enzyme activity assay was initiated by adding His-tag purified enzymes or the empty vector control to the assay buffer containing either the 50 mM β-alanine or 50 mM 5-aminovaleric acid and incubated at 37° C. for 2 h. The formation of β-alanyl-CoA and 5-amino-3-oxopentanoyl-CoA was monitored by LC-MS to identify products by expected masses at distinct retention times.

Figure 22:
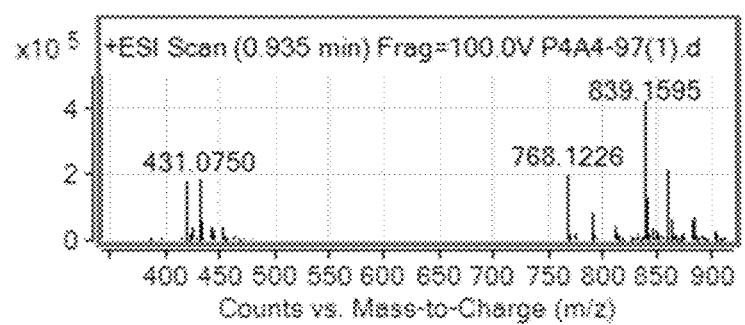
FIG. 22 is a LC-MS ESI mass spectrum performed in positive mode that identifies the product of peak (a) (see chromatogram of FIG. 21) as β-alanine-CoA by comparison of the observed and expected masses for the $[M+H]^+$ and $[M+2H]^{2+}$ species. Expected $[M+H]^+$ for products (a): 839.1596 (1 charge) & $[M+2H]^{2+}$: 420.0834 (2 charges).
Figure 23:
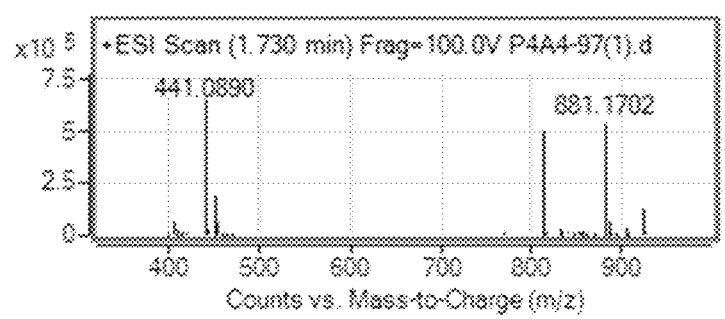
FIG. 23 is a LC-MS ESI mass spectrum performed in positive mode that identifies the product of peak (b) (see chromatogram of FIG. 21) as 5-amino-3-oxopentanoyl-CoA by comparison of the observed and expected masses for the $[M+H]^+$ and $[M+2H]^{2+}$ species. Expected $[M+H]^+$ for products (b): 881.1702 (1 charge) & $[M+2H]^{2+}$: 411.0887 (2 charges).

The 4-hydroxybutyrate-CoA transferase gene product of SEQ ID NO: 18 accepted β-alanine as substrate and formed β-alanyl-CoA and 5-amino-3-oxopentanoyl-CoA as products, which was confirmed against the empty vector control. See row for EC 2.8.3- in Table 1, and peaks confirming product identity by expected mass in FIG. 22 (β-alanyl-CoA: ESI-MS expected $[M+H]^+=839.1596$ and $[M+2H]^{+2}=420.0834$; found 839.1595 and 431.0750) and FIG. 23 (5-amino-3-oxopentanoyl-CoA: ESI-MS expected $[M+H]^+=881.1702$ and $[M+2H]^{+2}=441.0887$; found 881.1702 and 441.0890).

Table 1 below presents the results of the enzyme assays. The enzymes are listed by EC number, gene encoding the enzyme, and name. The enzyme assays were performed as described above with a β-alanine (C3) and 5-aminovaleric acid (C5) substrates in a sequence of two reactions (see FIG. 20). Assays were monitored by LC-MS, and observed product (indicated by a check mark) and no product observed (indicated by x), are reported for the 4-hydroxybuterate-CoA transferase.

|  |  |  | C3 | | C5 | |
| --- | --- | --- | --- | --- | --- | --- |
| E.C. | Gene | Name | Product Reaction 1 | Product Reaction 2 | Product Reaction 1 | Product Reaction 2 |
| 2.3.1.16/ 2.3.1.9 | Q0KBP1 | BktB | x | x | x | x |
| 2.8.3.8 | Q9L3F7 | 237 | x | x | x | x |
| 2.8.3- | Q9RM86 | 244 | ✓ | ✓ | x | x |
| 2.8.3.10 | J1G510 | 337 | x | x | x | x |
| 2.8.3.18 | B3EY95 | 344 | x | x | x | x |
| 2.3.1.174 | P0C7L2 | PaaJ | x | x | x | x |

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of producing 5-amino-3-oxopentanoyl-[ACP] or 5-amino-3-oxopentanoyl-CoA or corresponding salts thereof, said method comprising enzymatically converting β-alanyl-[ACP] or β-alanyl-CoA respectively to 5-amino-3-oxopentanoyl-[ACP] or 5-amino-3-oxopentanoyl-CoA or corresponding salts thereof, using a polypeptide having the activity of a β-ketoacyl synthase or a β-ketothiolase classified under EC. 2.3.1.- and/or a CoA transferase classified under EC 2.8.3-.

2. The method of claim 1, wherein said polypeptide having the activity of a β-ketoacyl synthase is classified under EC 2.3.1.41, EC 2.3.1.179 or EC 2.3.1.180 and wherein said polypeptide having the activity of a β-ketothiolase is classified under EC 2.3.1.16 or EC 2.3.1.174.

3. The method of claim 1, wherein said polypeptide having the activity of a β-ketothiolase has at least 70% sequence identity to the amino acid sequence set forth in SEQ ID NOs: 1 or 13 and said polypeptide having the activity of a β-ketoacyl synthase has at least 70% sequence identity to the amino acid sequence set forth in SEQ ID NO: 14 and said polypeptide having the activity of a CoA transferase has at least 70% sequence identity to the amino acid sequence set forth in SEQ ID NO: 19.

4. The method of claim 3, wherein said polypeptide having the activity of a β-ketothiolase has at least 70% sequence identity to the amino acid sequence set forth in SEQ ID NOs: 1 or 13 and is capable of converting β-alanyl-CoA to 5-amino-3-oxopentanoyl-CoA and said polypeptide having the activity of a β-ketoacyl synthase has at least 70% sequence identity to the amino acid sequence set forth in SEQ ID NO: 14 and is capable of converting β-alanyl-CoA and β-alanyl-[ACP] to 5-amino-3-oxopentanoyl-CoA and 5-amino-3-oxopentanoyl-[ACP] respectively and said polypeptide having the activity of a CoA transferase has at least 70% sequence identity to the amino acid sequence set forth in SEQ ID NO: 19 and is capable of converting β-alanyl-CoA to 5-amino-3-oxopentanoyl-CoA.

5. The method of claim 1, further comprising enzymatically converting 5-amino-3-oxopentanoyl-[ACP] or 5-amino-3-oxopentanoyl-CoA or the corresponding salts thereof to 7-aminoheptanoate or the salt thereof using polypeptides having the enzymatic activities of a 3-oxoacyl-[ACP] reductase or a 3-hydroxyacyl-CoA dehydrogenase, a 3-hydroxyacyl-[ACP] dehydratase or an enoyl-CoA hydratase, an enoyl-[ACP] reductase or a trans-2-enoyl-CoA reductase, a β-ketoacyl synthase or a β-ketothiolase and a thioesterase or a CoA transferase.

6. A method for biosynthesizing 7-aminoheptanoate, said method comprising enzymatically synthesizing 5-amino-3-oxopentanoyl-[ACP] or 5-amino-3-oxopentanoyl-CoA or the salts thereof from β-alanyl-[ACP] or β-alanyl-CoA using a polypeptide having the activity of a β-ketoacyl synthase or a β-ketothiolase classified under EC. 2.3.1.- and/or a CoA transferase classified under EC 2.8.3-, and enzymatically converting 5-amino-3-oxopentanoyl-[ACP] or 5-amino-3-oxopentanoyl-CoA or the salts thereof to 7-aminoheptanoate.

7. The method of claim 6, wherein 5-amino-3-oxopentanoyl-[ACP] is converted to 5-amino-3-hydroxypentanoyl-[ACP] using a polypeptide having the activity of 3-oxoacyl-[ACP] reductase and 5-amino-3-oxopentanoyl-CoA is converted to 5-amino-3-hydroxypentanoyl-CoA using a polypeptide having the activity of a 3-hydroxyacyl-CoA dehydrogenase; 5-amino-3-hydroxypentanoyl-[ACP] is converted to 5-amino-pent-2-enoyl-[ACP] using a polypeptide having the activity of a 3-hydroxyacyl-[ACP] dehydratase and 5-amino-3-hydroxypentanoyl-CoA is converted to 5-amino-pent-2-enoyl-CoA using a polypeptide having the activity of an enoyl-CoA hydratase; 5-amino-pent-2-enoyl-[ACP] is converted to 5-amino-pentanoyl-[ACP] using a polypeptide having the activity of an enoyl-[ACP] reductase and 5-amino-pent-2-enoyl-CoA is converted to 5-amino-pentanoyl-CoA using a polypeptide having the activity of a trans-2-enoyl-CoA-reductase; 5-amino-pentanoyl-[ACP] is converted to 7-amino-3-oxoheptanoyl-[ACP] using a polypeptide having the activity of a β-ketoacyl synthase and 5-amino-pentanoyl-CoA is converted to 7-amino-3-oxoheptanoyl-CoA using a polypeptide having the activity of a β-ketothiolase; 7-amino-3-oxoheptanoyl-[ACP] is converted to 7-amino-3-hydroxyheptanoyl-[ACP] using a polypeptide having the activity of a 3-oxoacyl-[ACP]reductase and 7-amino-3-oxoheptanoyl-CoA is converted to 7-amino-3-hydroxyheptanoyl-CoA using a polypeptide having the activity of a 3-hydroxyacyl-CoA-dehydrogenase; 7-amino-3-hydroxyheptanoyl-[ACP] is converted to 7-amino-hept-2-enoyl-[ACP] using a polypeptide having the activity of a 3-hydroxyacyl-[ACP] dehydratase and 7-amino-3-hydroxyheptanoyl-CoA is converted to 7-amino-hept-2-enoyl-CoA using a polypeptide having the activity of an enoyl-CoA hydratase; 7-amino-hept-2-enoyl-[ACP] is converted to 7-aminoheptanoyl-[ACP] using a polypeptide having the activity of an enoyl-[ACP] reductase and 7-amino-hept-2-enoyl-CoA is converted to 7-aminoheptanoyl-CoA using a polypeptide having the activity of a trans-2-enoyl-CoA reductase; and 7-aminoheptanoyl-[ACP] is converted to 7-aminoheptanoate using a polypeptide having the activity of a thioesterase and 7-aminoheptanoyl-CoA is converted to 7-aminoheptanoate using a polypeptide having the activity of a thioesterase or a CoA transferase.

8. The method of claim 5, said method further comprising enzymatically converting 7-aminoheptanoate to pimelic acid, 7-hydroxyheptanoate, heptamethylenediamine or 1,7-heptanediol or corresponding salts thereof in one or more steps.

9. The method of claim 8, wherein 7-aminoheptanoate is converted to pimelic acid using one or more polypeptides having the enzymatic activity of a ω-transaminase a 7-oxoheptanoate dehydrogenase, a 6-oxohexanoate dehydrogenase, a 5-oxopentanoate dehydrogenase, or an aldehyde dehydrogenase.

10. The method of claim 8, wherein 7-aminoheptanoate is converted to 7-hydroxyheptanoate using one or more polypeptides having the enzymatic activity of an alcohol dehydrogenase, a 6-hydroxyhexanoate dehydrogenase, a 5-hydroxypentanoate dehydrogenase, a 4-hydroxybutanoate dehydrogenase, and a ω-transaminase.

11. The method of claim 8, wherein 7-aminoheptanoate is converted to heptamethylenediamine using polypeptides having the enzymatic activity of a carboxylate reductase and one or more ω-transaminases.

12. The method of claim 8, wherein 7-aminoheptanoate is converted to heptamethylenediamine using polypeptides having the enzymatic activity of a carboxylate reductase, a ω-transaminase and an alcohol dehydrogenase.

13. The method of claim 8, wherein 7-aminoheptanoate is converted to heptamethylenediamine using polypeptides having the enzymatic activity of an N-acetyltransferase, a carboxylate reductase, a ω-transaminase, and a deacylase.

14. The method of claim 8, wherein 7-aminoheptanoate is converted to heptamethylenediamine using polypeptides having the enzymatic activity of one or more alcohol dehydrogenases and one or more ω-transaminases.

15. The method of claim 8, wherein 7-hydroxyheptanoate is converted to 1,7-heptanediol using a polypeptide having the enzymatic activity of a carboxylate reductase and a polypeptide having the enzymatic activity of an alcohol dehydrogenase.

16. The method of claim 1, wherein said β-alanyl-[ACP] or said β-alanyl-CoA is enzymatically produced from malonyl-CoA or L-aspartate.

17. The method of claim 16, wherein β-alanyl-[ACP] or said β-alanyl-CoA is enzymatically produced from malonyl-CoA or L-aspartate using one or more polypeptides having the enzymatic activity of a malonyl-CoA-reductase, a β-alanine-pyruvate aminotransferase, an α-aspartate decarboxylase, a CoA transferase and an [ACP]-acetyltransferase.

18. The method of claim 1, wherein said method is performed in a recombinant microorganism.

19. The method of claim 18, wherein said microorganism is subjected to a cultivation strategy under aerobic, anaerobic or, micro-aerobic cultivation conditions.

20. The method of claim 18, wherein said microorganism is cultured under conditions of nutrient limitation.

21. The method of claim 18, wherein the principal carbon source fed to the fermentation derives from a biological feedstock.

22. The method of claim 18, wherein the principal carbon source fed to the fermentation derives from a non-biological feedstock.

23. The method of claim 18, wherein the microorganism is a prokaryote.

24. The method of claim 18, wherein the microorganism is a eukaryote.

25. The method of claim 18, wherein the microorganism's tolerance to high concentrations of a C7 building block is improved relative to a wild type organism.

26. The method of claim 18, wherein said microorganism comprises an attenuation to one or more of the following enzymes: polyhydroxyalkanoate synthase, an acetyl-CoA thioesterase, a phosphotransacetylase forming acetate, an acetate kinase, a lactate dehydrogenase, a menaquinol-fumarate oxidoreductase, an alcohol dehydrogenase forming ethanol, a triose phosphate isomerase, a pyruvate decarboxylase, a glucose-6-phosphate isomerase, NADH-consuming transhydrogenase, an NADH-specific glutamate dehydrogenase, a NADH/NADPH-utilizing glutamate dehydrogenase, a pimeloyl-CoA dehydrogenase; an acyl-CoA dehydrogenase accepting C7 building blocks and central precursors as substrates; a butaryl-CoA dehydrogenase; or an adipyl-CoA synthetase.

27. The method of claim 18, wherein said microorganism overexpresses one or more genes encoding: an acetyl-CoA synthetase, a 6-phosphogluconate dehydrogenase; a transketolase; a puridine nucleotide transhydrogenase; a glyceraldehyde-3P-dehydrogenase; a malic enzyme; a glucose-6-phosphate dehydrogenase; a glucose dehydrogenase; a fructose 1,6 diphosphatase; a L-alanine dehydrogenase; a L-glutamate dehydrogenase; a formate dehydrogenase; a L-glutamine synthetase; a diamine transporter; a dicarboxylate transporter; and/or a multidrug transporter.

28. A non-naturally occurring biochemical network comprising β-alanyl-[ACP] or β-alanyl-CoA, an exogenous nucleic acid encoding a polypeptide having the activity of a β-ketothiolase or a β-ketoacyl synthase classified under EC. 2.3.1, and a 5-amino-3-oxopentanoyl-[ACP] or 5-amino-3-oxopentanoyl-CoA respectively.

29. A non-naturally occurring biochemical network comprising at least one exogenous nucleic acid encoding a polypeptide having the enzymatic activity of (i) a β-ketoacyl synthase and/or a β-ketothiolase, (ii) a thioesterase or a CoA transferase, and one or more of (iii) a 3-hydroxyacyl-CoA dehydrogenase or a 3-oxoacyl-[ACP] reductase, (iv) an enoyl-CoA hydratase or 3-hydroxyacyl-[ACP] dehydratase, and (v) a trans-2-enoyl-CoA reductase or enoyl-[ACP] reductase, said microorganism producing 7-aminoheptanoate or the corresponding salt thereof.

30. A method of producing 5-amino-3-oxopentanoyl-CoA or a salt thereof, said method comprising enzymatically converting β-alanine to 5-amino-3-oxopentanoyl-CoA or a salt thereof using a polypeptide having the activity of a β-ketoacyl synthase or a β-ketothiolase classified under EC. 2.3.1.-, further comprising enzymatically converting β-alanine or the salt thereof to 5-amino-3-oxopentanoyl-CoA using polypeptides having the enzymatic activities of a β-ketothiolase, CoA transferase, acetyl-CoA hydrolase, succinyl-CoA: acetate CoA-transferase, and thiolase.

31. The method of claim 30, wherein said CoA-transferase is classified under EC 2.8.3.-.

* * * * *